US008486893B2

(12) United States Patent
Mi et al.

(10) Patent No.: US 8,486,893 B2
(45) Date of Patent: *Jul. 16, 2013

(54) TREATMENT OF CONDITIONS INVOLVING DEMYELINATION

(75) Inventors: Sha Mi, Belmont, MA (US); R. Blake Pepinsky, Arlington, MA (US); John McCoy, Reading, MA (US)

(73) Assignee: Biogen Idec MA Inc., Cambridge, MA (US)

(*) Notice: Subject to any disclaimer, the term of this patent is extended or adjusted under 35 U.S.C. 154(b) by 332 days.

This patent is subject to a terminal disclaimer.

(21) Appl. No.: 11/165,576

(22) Filed: Jun. 24, 2005

(65) Prior Publication Data

US 2006/0009388 A1    Jan. 12, 2006

Related U.S. Application Data

(60) Provisional application No. 60/680,475, filed on May 13, 2005, provisional application No. 60/628,435, filed on Nov. 15, 2004, provisional application No. 60/617,297, filed on Oct. 7, 2004, provisional application No. 60/582,966, filed on Jun. 24, 2004.

(51) Int. Cl.
*A61K 39/395*    (2006.01)
*C07K 14/435*    (2006.01)
*C07K 16/28*    (2006.01)
*C07K 16/34*    (2006.01)
*C12P 21/08*    (2006.01)

(52) U.S. Cl.
USPC ............... 514/17.9; 530/389.6; 424/130.1; 424/133.1; 424/135.1; 424/139.1; 435/69.6

(58) Field of Classification Search
None
See application file for complete search history.

(56) References Cited

U.S. PATENT DOCUMENTS

| | | | |
|---|---|---|---|
| 4,399,216 A | 8/1983 | Axel et al. |
| 4,444,887 A | 4/1984 | Hoffman |
| 4,510,245 A | 4/1985 | Cousens et al. |
| 4,634,665 A | 1/1987 | Axel et al. |
| 4,694,778 A | 9/1987 | Learn et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 4,968,615 A | 11/1990 | Koszinowski et al. |
| 5,122,464 A | 6/1992 | Wilson et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,252,714 A | 10/1993 | Harris et al. |
| 5,258,498 A | 11/1993 | Huston et al. |
| 5,314,995 A | 5/1994 | Fell, Jr. et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,130 A | 6/1995 | Capon et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,565,335 A | 10/1996 | Capon et al. |
| 5,569,825 A | 10/1996 | Lonberg et al. |
| 5,571,698 A | 11/1996 | Ladner et al. |
| 5,574,009 A | 11/1996 | Cohen et al. |
| 5,580,717 A | 12/1996 | Dower et al. |
| 5,585,089 A | 12/1996 | Queen et al. |
| 5,589,369 A | 12/1996 | Seidman et al. |
| 5,625,126 A | 4/1997 | Lonberg et al. |
| 5,633,425 A | 5/1997 | Lonberg et al. |
| 5,658,570 A | 8/1997 | Newman et al. |
| 5,658,727 A | 8/1997 | Barbas et al. |
| 5,661,016 A | 8/1997 | Lonberg et al. |
| 5,693,761 A | 12/1997 | Queen et al. |
| 5,693,762 A | 12/1997 | Queen et al. |
| 5,693,780 A | 12/1997 | Newman et al. |
| 5,698,426 A | 12/1997 | Huse |
| 5,733,743 A | 3/1998 | Johnson et al. |
| 5,750,753 A | 5/1998 | Kimae et al. |
| 5,756,096 A | 5/1998 | Newman et al. |
| 5,780,225 A | 7/1998 | Wigler et al. |
| 5,807,715 A | 9/1998 | Morrison et al. |
| 5,811,524 A | 9/1998 | Brams et al. |
| 5,814,318 A | 9/1998 | Lonberg et al. |
| 5,821,047 A | 10/1998 | Garrard et al. |
| 5,837,821 A | 11/1998 | Wu |

(Continued)

FOREIGN PATENT DOCUMENTS

EP    0 154 316 B2    9/1985
EP    0 239 400 B2    9/1987

(Continued)

OTHER PUBLICATIONS

Daugherty et al. Advanced Drug Delivery Reviews, 58:686-706 (2006).*
Li et al. Society for Neuroscience Meeting Abstracts, Program 678.3, Oct. 2003.*
Inoue et al., "Inhibition of the leucine-rich repeat protein LINGO-1 enhances survival, structure, and function of dopaminergic neurons in Parkinson's disease models", Proceedings of the National Academy of Sciences, USA, 104(36): 14430-14435, Sep. 4, 2007.*
Torkildsen et al. Acta Neurol Scand Suppl, 188:72-76, 2008.*
Li et al. Journal of Neuroscience, 24(46):10511-10520, 2004.*
Baumann, N., et al., "Biology of Oligodendrocyte and Myelin in the Mammalian Central Nervous System," *J. Physiol. Rev.* 81:871-927 (2001).
Carim-Todd, L., et al., "LRRN6A/LERN1 (leucine-rich repeat neuronal protein 1), a novel gene with enriched expression in limbic system and neocortex," *Eur. J. Neurosci.* 18:3167-3183, Federation of European Neuroscience Societies (2003).

(Continued)

*Primary Examiner* — Daniel E Kolker
*Assistant Examiner* — Stacey N MacFarlane
(74) *Attorney, Agent, or Firm* — Sterne, Kessler, Goldstein & Fox PLLC

(57) ABSTRACT

The invention provides methods of treating diseases, disorsers or injuries involving demyelination and dysmyelination, including multiple sclerosis, by the administration of an Sp35 antagonist.

20 Claims, 21 Drawing Sheets

U.S. PATENT DOCUMENTS

| | | | |
|---|---|---|---|
| 5,892,019 | A | 4/1999 | Schlom et al. |
| 5,939,598 | A | 8/1999 | Kucherlapati et al. |
| 5,969,108 | A | 10/1999 | McCafferty et al. |
| 6,075,181 | A | 6/2000 | Kucherlapati et al. |
| 6,150,584 | A | 11/2000 | Kucherlapati et al. |
| 6,159,730 | A | 12/2000 | Reff |
| 6,180,370 | B1 | 1/2001 | Queen et al. |
| 6,190,887 | B1 | 2/2001 | Boyce et al. |
| 6,338,953 | B1 | 1/2002 | Boyce et al. |
| 6,413,777 | B1 | 7/2002 | Reff et al. |
| 6,420,140 | B1 | 7/2002 | Hori et al. |
| 6,458,592 | B1 | 10/2002 | Jakobovits et al. |
| 6,686,451 | B1 | 2/2004 | Desnoyers et al. |
| 6,696,290 | B2 | 2/2004 | Fitzpatrick et al. |
| 6,974,689 | B1 | 12/2005 | Ashkenazi et al. |
| 7,223,558 | B2 | 5/2007 | Wu et al. |
| 7,785,829 | B2 | 8/2010 | Mi et al. |
| 8,058,406 | B2 | 11/2011 | Mi et al. |
| 8,128,926 | B2 | 3/2012 | Mi et al. |
| 8,153,580 | B2 | 4/2012 | Mi et al. |
| 2002/0123057 | A1 | 9/2002 | Zauderer et al. |
| 2002/0182671 | A1 | 12/2002 | Lal et al. |
| 2003/0195163 | A1 | 10/2003 | Wu et al. |
| 2004/0067490 | A1 | 4/2004 | Zhong et al. |
| 2004/0253605 | A1 | 12/2004 | McCarthy et al. |
| 2005/0123990 | A1 | 6/2005 | Lal et al. |
| 2005/0214288 | A1 | 9/2005 | Bell et al. |
| 2005/0215770 | A1 | 9/2005 | Bell et al. |
| 2006/0009288 | A1 | 1/2006 | deVos et al. |
| 2006/0009388 | A1 | 1/2006 | Mi et al. |
| 2009/0017039 | A1 | 1/2009 | Mi et al. |
| 2009/0175872 | A1 | 7/2009 | Mi et al. |
| 2009/0246189 | A1 | 10/2009 | Mi et al. |
| 2010/0074907 | A1 | 3/2010 | Mi et al. |
| 2010/0297121 | A1 | 11/2010 | Mi |
| 2011/0311542 | A1 | 12/2011 | Mi et al. |
| 2012/0014960 | A1 | 1/2012 | Mi et al. |

FOREIGN PATENT DOCUMENTS

| | | |
|---|---|---|
| EP | 0 323 997 B1 | 7/1989 |
| EP | 0 338 841 B1 | 10/1989 |
| EP | 0 368 684 B1 | 5/1990 |
| EP | 0 396 387 B1 | 11/1990 |
| EP | 0 401 384 A1 | 12/1990 |
| EP | 0 256 055 B1 | 8/1991 |
| EP | 0 519 596 B1 | 12/1992 |
| EP | 0 592 106 B1 | 4/1994 |
| EP | 1 074 617 A2 | 2/2001 |
| EP | 0 058 481 | 5/2003 |
| EP | 1 574 520 | 9/2005 |
| WO | WO 86/05807 A1 | 10/1986 |
| WO | WO 88/09810 A1 | 12/1988 |
| WO | WO 89/01036 A1 | 2/1989 |
| WO | WO 89/10134 A1 | 11/1989 |
| WO | WO 89/12624 A2 | 12/1989 |
| WO | WO 90/02809 A1 | 3/1990 |
| WO | WO 90/11364 A1 | 10/1990 |
| WO | WO 91/09967 A1 | 7/1991 |
| WO | WO 91/10737 A1 | 7/1991 |
| WO | WO 91/10741 A1 | 7/1991 |
| WO | WO 91/14438 A1 | 10/1991 |
| WO | WO 92/01047 A1 | 1/1992 |
| WO | WO 92/08495 A1 | 5/1992 |
| WO | WO 92/18619 A1 | 10/1992 |
| WO | WO 92/22324 A1 | 12/1992 |
| WO | WO 93/11236 A1 | 6/1993 |
| WO | WO 94/09817 A1 | 5/1994 |
| WO | WO 95/15982 A2 | 6/1995 |
| WO | WO 95/20401 A1 | 8/1995 |
| WO | WO 96/33735 A1 | 10/1996 |
| WO | WO 98/16654 A1 | 4/1998 |
| WO | WO 98/24893 A2 | 6/1998 |
| WO | WO 98/46645 A2 | 10/1998 |
| WO | WO 98/50433 | 11/1998 |
| WO | WO 98/52976 A1 | 11/1998 |
| WO | WO 99/06427 A1 | 2/1999 |
| WO | WO 99/14328 A2 | 3/1999 |
| WO | WO 00/15796 A2 | 3/2000 |
| WO | WO 00/34317 A2 | 6/2000 |
| WO | WO 01/04311 A1 | 1/2001 |
| WO | WO 01/12662 A2 | 2/2001 |
| WO | WO 01/40466 A2 | 6/2001 |
| WO | WO 01/55333 A2 | 8/2001 |
| WO | WO 01/57262 A1 | 8/2001 |
| WO | WO 02/01047 A1 | 1/2002 |
| WO | WO 02/14368 A2 | 2/2002 |
| WO | WO 02/29058 A2 | 4/2002 |
| WO | WO 02/060955 A2 | 8/2002 |
| WO | WO 02/068579 A2 | 9/2002 |
| WO | WO 02/096948 A2 | 12/2002 |
| WO | WO 03/023008 A2 | 3/2003 |
| WO | WO 03/031462 A1 | 4/2003 |
| WO | WO 03/035833 A2 | 5/2003 |
| WO | WO 03/083047 A2 | 10/2003 |
| WO | WO 2004/085648 A2 | 10/2004 |
| WO | WO 2005/079566 A2 | 9/2005 |
| WO | WO 96/34096 A1 | 10/2006 |

OTHER PUBLICATIONS

Chang, A., et al., "Premyelinating Oligodendrocytes in Chronic Lesions of Multiple Sclerosis," *N. Engl. J. Med.* 346:165-173 (2002).

Chen, Y., et at, "AMIGO and friends: An emerging family of brain-enriched, neuronal growth modulating, type 1 transmembrane proteins with leucine-rich repeats (LRR) and cell adhesion molecule motifs," *Brain Res. Rev.* 51:265-74 (2006).

Cohen, S., et al., "Nonchromosomal Antibiotic Resistance in Bacteria: Genetic Transformation of *Escherichia coli* by R-Factor DNA," *Proc. Natl. Acad. Sci. USA* 69:2110-2114 (1972).

Huang, J., et al., Glial Membranes at the Node of Ranvier Prevent Neurite Outgrowth, *Science* 310:1813-7 (2005).

Li, W., et al., "Neutralization of Myelin-Associated NOGO-A by a NOGO Receptor-FC Fusion Protein," *Society for Neuroscience* Abstracts ABS3332 (2002).

Mi, S., et al., "A Novel CNS-Specific Protein Promotes Axonal Elongation by Modulating RHOA Signaling," *Society for Neuroscience* Abstracts, Abstract No. 891.5 (2003).

Mi, S., et al., "LINGO-1 is a component of the Nogo-66 receptor/p75 signaling complex," *Nat. Neurosci.* 7:221-8 (2004).

Mi, S., et al., "LINGO-1 negatively regulates myelination by oligodendrocytes," *Nat. Neurosci.* 8:745-51 (2005).

Okafuji, T., et al., "Expression patter of LINGO-1 in the developing nervous system of the chick embryo," *Gene Expr. Patterns* 6:57-62 (2005).

Park, J.B., et al., A TNF Receptor Family Member, TROY, is a Coreceptor with Nogo Receptro in Mediating the Inhibitory Activity of Myelin Inhibitors, *Neuron* 3:345-51 (2005).

Park, J.B., et al., A TNF Receptor Family Member, TROY, is a Coreceptor with Nogo Receptro in Mediating the Inhibitory Activity of Myelin Inhibitors, Erratum in *Neuron* 3:815 (2005).

Rubinson, D.A., et al., "A lentivirus-based system to functionally silence genes in primary mammalian cells, stem cells and transgenic mice by RNA interference," *Nat. Genet.* 33:401-406 (2003).

Shao, Z., et al., "TAJ/TROY, an Orphan TNF Receptor Family Member, Binds Nogo-66 Receptor 1 and Regulates Axonal Regeneration," *Neuron* 45:353-9 (2005).

Trifunovski, A. et al. "Neuronal activity-induced regulation of LINGO-1," *Neuroreport* 15:2397-2400 (2004).

Yu, W., et al., "Segregation of Nogo66 receptors into lipid rafts in rat brain and inhibition of Nogo66 signaling by cholesterol depetion," *FEBS Lett.* 577:87-92 (2004).

NCBI Entrez, Accession No. BC011057, Strausberg, R.L., et al. (first available Jul. 30, 2001; last updated Jul. 15, 2006).

NCBI Entrez, Accession No. BC068558, Strausberg, R.L., et al. (first available Apr. 6, 2004; last updated Jul. 21, 2005).

NCBI Entrez, Accession No. NM_152570, Clark, H.F., et al. (first available Sep. 6, 2002; last updated Dec. 25, 2005).

NCBI Entrez, Accession No. NM_032808, Carim-Todd, L., et al. (first available May 31, 2001; last updated Sep. 17, 2006).

NCBI Entrez, Accession No. DR000281, Birkett, C., et al. (first available May 17, 2005; last updated May 17, 2005) -,1.

NCBI Entrez, Accession No. AY324320, Carim-Todd, L., et al. (first available May 4, 2004; last updated May 4, 2004).

NCBI Entrez, Accession No. AY324322, Carim-Todd, L., et al. (first available May 4, 2004; last updated May 4, 2004).

NCBI Entrez, Accession No. AY324323, Carim-Todd, L., et al. (first available May 4, 2004; last updated May 4, 2004).

Adams, G.P., and Weiner, L.M., "Monoclonal antibody therapy of cancer," *Nat. Biotechol.* 23:1147-1157, Nature America Publishing (Sep. 2005).

Chang, A., et al., "Premyelinating Oligodendrocytes in Chronic Lesions of Multiple Sclerosis," *N. Engl. J. Med.* 346:165-173, Massachusetts Medical Society (2002).

Estaquier, J., et al., "Fas-mediated apoptosis of CD4+ and CD8+ T cells from human immunodeficiency virus-infected persons: differential in vitro preventive effect of cytokines and protease antagonists," *Blood* 87:4959-4966, The American Society of Hematology (1996).

Liang, X., et al., "Signaling from Integrins to Fyn to Rho Family GTPases Regulates Morphologic Differentiation of Oligodendrocytes," *J. Neurosci.* 24:7140-7149, Society of Neuroscience (Aug. 2004).

Rader, R.A., "TNF Receptor-IgG Fc, rDNA," in *Biopharmaceutical Products in the U.S. and European Markets*, 5th ed., pp. 610-619, BioPlan Associates, Inc (Jul. 2006).

Reichert, J.M., et al., "Monoclonal antibody successes in the clinic," *Nat. Biotech.* 23:1073-1078, Nature America Publishing (Sep. 2005).

Rosado, E., et al., "Transforming growth factor-β1 regulation of growth zone chondrocytes is mediated by multiple interacting pathways," *Biochim. Biophys. Acta* 1590:1-15, Elsevier (2002).

Supplementary European Search Report for European Application No. EP 05 76 4255, The Hauge, Netherlands, dated Nov. 5, 2009.

Brittis, P.A., et al., Nogo Domains and a Nogo Receptor: Implications for Axon Regeneration, *Neuron* 30:11-14 Cell Press (2001).

Chen, M.S., et al., "Nogo-A is a Myelin-Associated Neurite Outgrowth Inhibitor and an Antigen for Monoclonal Antibody IN-1," *Nature* 403:434-439, Macmillan Magazines Ltd. (2000).

Domeniconi M., et al., "Myelin-Associated Glycoprotein Interacts with the Nogo66 Receptor to Inhibit Neurite Outgrowth," *Neuron* 35:283-290, Cell Press (2002).

Fournier, A.E., et al., "Identification of a Receptor Mediating Nogo-66 Inhibition of Axonal Regeneration," *Nature* 409:341-346, Nature Publishing Group (2001).

Fu, Q.-L., et al., "Blocking LINGO-1 Function Promotes Retinal Ganglion Cell Survival Following Ocular Hypertension and Optic Nerve Transection," *Invest. Ophthal. Vis. Sci.* 49:975-985, Association for Research in Vision and Ophthalmology (Mar. 2008).

Grandpré, T., et al., "Identification of the Nogo Inhibitor of Axon Regeneration as a Reticulon Protein," *Nature* 403:439-444, Macmillan Magazines Ltd. (2000).

Grimpe, B., et al., "The Critical Role of Basement Membrane-Independent Laminin γ1 Chain During Axon Regeneration in the CNS," *J. Neurosci.* 22:3144-3160, Society for Neuroscience (2002).

Jones, L.L., et al., "NG2 Is a Major Chondroitin Sulfate Proteoglycan Produced after Spinal Cord Injury and Is Expressed by Macrophages and Oligodendrocyte Progenitors," *J. Neurosci.* 22:2792-2803, Society for Neuroscience (2002).

Kasper, C., et al, "Structural Basis of Cell—Cell Adhesion by NCAM," *Nat. Struct. Biol.* 7:389-393, Nature America Inc. (2000).

McKerracher, L., et al., "Identification of Myelin-Associated Glycoprotein as a Major Myelin-Derived Inhibitor of Neurite Growth," *Neuron* 13:805-811, Cell Press (1994).

Mi, S., et al., "LINGO-1 antagonist promotes spinal cord remyelination and axonal integrity in MOG-induced experimental autoimmune encephalomyelitis," *Nat. Med.* 13:1228-1233, Nature Publishing Group (Oct. 2007).

Mikol D.D. et al., "A Phosphatidylinositol-Linked Peanut Agglutinin-Binding Glycoprotein in Central Nervous System Myelin and on Oligodendrocytes," *J. Cell. Biol.* 106:1273-1279, The Rockefeller University Press (1988).

Mukhopadhyay, G., et al., "A Novel Role for Myelin-Associated Glycoprotein as an Inhibitor of Axonal Regeneration," *Neuron* 13:757-767, Cell Press (1994).

Rutishauser, U. et al., "Cell Adhesion Molecules in Vertebrate Neural Develeopment," *Physiol. Rev.* 68:819-857, American Physiological Society (1988).

Wang, K.C., et al., "Oligodendrocyte-Myelin Glycoprotein is a Nogo Receptor Ligand That Inhibits Neurite Outgrowth," *Nature* 417:941-944, Nature Publishing Group (2002).

Chard, D.T., et al., "Progressive grey matter atrophy in clinically early relapsing-remitting multiple sclerosis," *Multiple Sclerosis* 10:387-391, Arnold, England (2004).

Fisniku, L.K., et al., "Gray Matter Atrophy Is Related to Long-Term Disability in Multiple Sclerosis," *Annals of Neurology* 64(3):247-254, American Neurological Association by Wiley-Liss, Inc., United States (2008).

Pepinsky, R.B., et al., "Exposure Levels of Anti-LINGO-1 Li81 Antibody in the Central Nervous System and Dose-Efficacy Relationships in Rat Spinal Cord Remyelination Models after Systemic Administration," *J. Pharmacol. Exp. Ther.* 339(2):519-529, American Society for Pharmacology and Experimental Therapeutics, United States (2011).

Co-pending U.S. Appl. No. 13/356,413, inventors Mi et al., filed Jan. 23, 2012 (Not Published).

* cited by examiner

FIG. 1A

```
GGAGAGACATGCGATTGGTGACCGAGCCGAGCGGACCGAAGGCGCGCCCGA
GATGCAGGTGAGCAAGAGGATGCTGGCGGGGGGCGTGAGGAGCATGCCCAG
CCCCCTCCTGGCCTGCTGGCAGCCCATCCTCCTGCTGGTGCTGGGCTCAGTGC
TGTCAGGCTCGGCCACGGGCTGCCCGCCCCGCTGCGAGTGCTCCGCCCAGGA
CCGCGCTGTGCTGTGCCACCGCAAGCGCTTTGTGGCAGTCCCCGAGGGCATC
CCCACCGAGACGCGCCTGCTGGACCTAGGCAAGAACCGCATCAAAACGCTCA
ACCAGGACGAGTTCGCCAGCTTCCCGCACCTGGAGGAGCTGGAGCTAACGA
GAACATCGTGAGCGCCGTGGAGCCCGGCGCCTTCAACAACCTCTTCAACCTC
CGGACGCTGGGTCTCCGCAGCAACCGCCTGAAGCTCATCCCGCTAGGCGTCT
TCACTGGCCTCAGCAACCTGACCAAGCTGGACATCAGCGAGAACAAGATTGT
TATCCTACTGGACTACATGTTTCAGGACCTGTACAACCTCAAGTCACTGGAGG
TTGGCGACAATGACCTCGTCTACATCTCTCACCGCGCCTTCAGCGGCCTCAAC
AGCCTGGAGCAGCTGACGCTGGAGAAATGCAACCTGACCTCCATCCCCACCG
AGGCGCTGTCCCACCTGCACGGCCTCATCGTCCTGAGGCTCCGGCACCTCAA
CATCAATGCCATCCGGGACTACTCCTTCAAGAGGCTCTACCGACTCAAGGTCT
TGGAGATCTCCCACTGGCCCTACTTGGACACCATGACACCCAACTGCCTCTAC
GGCCTCAACCTGACGTCCCTGTCCATCACACACTGCAATCTGACCGCTGTGCC
CTACCTGGCCGTCCGCCACCTAGTCTATCTCCGCTTCCTCAACCTCTCCTACA
ACCCCATCAGCACCATTGAGGGCTCCATGTTGCATGAGCTGCTCCGGCTGCA
GGAGATCCAGCTGGTGGGCGGGCAGCTGGCCGTGGTGGAGCCCTATGCCTTC
CGCGGCCTCAACTACCTGCGCGTGCTCAATGTCTCTGGCAACCAGCTGACCA
CACTGGAGGAATCAGTCTTCCACTCGGTGGGCAACCTGGAGACACTCATCCT
GGACTCCAACCCGCTGGCCTGCGACTGTCGGCTCCTGTGGGTGTTCCGGCGCC
GCTGGCGGCTCAACTTCAACCGGCAGCAGCCCACGTGCGCCACGCCCGAGTT
TGTCCAGGGCAAGGAGTTCAAGGACTTCCCTGATGTGCTACTGCCCAACTACT
TCACCTGCCGCCGCGCCCGCATCCGGGACCGCAAGGCCCAGCAGGTGTTTGT
GGACGAGGGCCACACGGTGCAGTTTGTGTGCCGGGCCGATGGCGACCCGCCG
CCCGCCATCCTCTGGCTCTCACCCCGAAAGCACCTGGTCTCAGCCAAGAGCA
ATGGGCGGCTCACAGTCTTCCCTGATGGCACGCTGGAGGTGCGCTACGCCCA
GGTACAGGACAACGGCACGTACCTGTGCATCGCGGCCAACGCGGGCGGCAA
CGACTCCATGCCCGCCCACCTGCATGTGCGCAGCTACTCGCCCGACTGGCCCC
ATCAGCCCAACAAGACCTTCGCTTTCATCTCCAACCAGCCGGGCGAGGGAGA
GGCCAACAGCACCCGCGCCACTGTGCCTTTCCCCTTCGACATCAAGACCCTCA
TCATCGCCACCACCATGGGCTTCATCTCTTTCCTGGGCGTCGTCCTCTTCTGCC
TGGTGCTGCTGTTTCTCTGGAGCCGGGGCAAGGGCAACACAAAGCACAACAT
CGAGATCGAGTATGTGCCCCGAAAGTCGGACGCAGGCATCAGCTCCGCCGAC
GCGCCCGCAAGTTCAACATGAAGATGATATGAGGCCGGGGCGGGGGGCAG
GGACCCCGGGCGGCCGGGCAGGGGAAGGGGCCTGGCCGCCACCTGCTCACT
CTCCAGTCCTTCCCACCTCCTCCCTACCCTTCTACACACGTTCTCTTTCTCCCT
CCCGCCTCCGTCCCTGCTGCCCCCGCCAGCCCTCACCACCTGCCCTCCTTC
TACCAGGACCTCAGAAGCCCAGACCTGGGGACCCCACCTACACAGGGGCATT
GACAGACTGGAGTTGAAAGCCGACGAACCGACACGCGGCAGAGTCAATAAT
TCAATAAAAAAGTTACGAACTTTCTCTGTAACTTGGGTTTCAATAATTATGGA
TTTTTATGAAAACTTGAAATAATAAAAAGAGAAAAAAACTATTTCCTATAGC
TAGTCGGAATGCAAACTTTTGACGTCCTGATTGCTCCAGGGCCCTCTTCCAAC
TCAGTTTCTTGTTTTTCTCTTCNTCCTNCTCCTCTTCTTCCTCCTTTCTCTTCTCT
TCCCCCAGTGGGGAGGGATCACTCAGGAAAACAGGAAAGGAGGTTCCAGCC
CCACCCACCTGCCCACCCCGCCCCAGGCACCATCAGGAGCAGGCTAGGGGGC
AGGCCTGGGCCCAGCTCCGGGCTGGCTTTTTGCAGGGCGCAGGTGGAGGGGAC
```

FIG. 1B

AGGTCTGCCGATGGGGGTGGGAGCCTGTCTGCTGGGCTGCCAGGCGGCACC
ACTGCAAGGGGTGGGAGCCTGGCTCGGGTGTGGCTGAGACTCTGGACAGAGG
CTGGGGTCCTCCTGGGGACAGCACAGTCAGTGGAGAGAGCCAGGGGCTGG
AGGTGGGGCCCACCCCAGCCTCTGGTCCCAGCTCTGCTGCTCACTTGCTGTGT
GGCCCTCAAGCAGGTCCACTGGCCTCTCTGGGCCTCAGTCTCCACATCTGTAC
AAATGGGAACATTACCCCCTGCCCTGCCTACCTNANAGGGCTGTTNTGAGGN
ATNGATGAGATGATGTATGT

FIG. 2

MLAGGVRSMPSPLLACWQPILLLVLGSVL
SGSATGCPPRCECSAQDRAVLCHRKRFVA
VPEGIPTETRLLDLGKNRIKTLNQDEFASF
PHLEELELNENIVSAVEPGAFNNLFNLRTL
GLRSNRLKLIPLGVFTGLSNLTKLDISENKI
VILLDYMFQDLYNLKSLEVGDNDLVYISHR
AFSGLNSLEQLTLEKCNLTSIPTEALSHLH
GLIVLRLRHLNINAIRDYSFKRLYRLKVLEI
SHWPYLDTMTPNCLYGLNLTSLSITHCNLT
AVPYLAVRHLVYLRFLNLSYNPISTIEGSM
LHELLRLQEIQLVGGQLAVVEPYAFRGLNY
LRVLNVSGNQLTTLEESVFHSVGNLETLIL
DSNPLACDCRLLWVFRRRWRLNFNRQQPT
CATPEFVQGKEFKDFPDVLLPNYFTCRRA
RIRDRKAQQVFVDEGHTVQFVCRADGDPP
PAILWLSPRKHLVSAKSNGRLTVFPDGTLE
VRYAQVQDNGTYLCIAANAGGNDSMPAHL
HVRSYSPDWPHQPNKTFAFISNQPGEGEA
NSTRATVPFPFDIKTLIIATTMGFISFLGVV
LFCLVLLFLWSRGKGNTKHNIEIEYVPRKS
DAGISSADAPRKFNMKMI

FIG. 3

ATGCTGGCAGGGGGTATGAGAAGCATGCCCAGCCCCCTCCTGGCCTGCTGGCA
GCCCATCCTCCTGCTGGTACTGGGCTCAGTGCTGTCAGGCTCTGCTACAGGCTG
CCCGCCCCGCTGCGAGTGCTCAGCGCAGGACCGAGCCGTGCTCTGCCACCGCA
AACGCTTTGTGGCGGTGCCCGAGGGCATCCCCACCGAGACTCGCCTGCTGGAC
CTGGGCAAAAACCGCATCAAGACACTCAACCAGGACGAGTTTGCCAGCTTCCC
ACACCTGGAGGAGCTAGAACTCAATGAAAACATCGTGAGCGCCGTGGAGCCA
GGCGCCTTCAACAACCTCTTCAACCTGAGGACTCTGGGGCTGCGCAGCAACCG
CCTGAAGCTTATCCCGCTGGGCGTCTTCACCGGCCTCAGCAACTTGACCAAGCT
GGACATCAGTGAGAACAAGATCGTCATCCTGCTAGACTACATGTTCCAAGACC
TATACAACCTCAAGTCGCTGGAGGTCGGCGACAACGACCTCGTCTACATCTCC
CATCGAGCCTTCAGCGGCCTCAACAGCCTGGAACAGCTGACGCTGGAGAAATG
CAATCTGACCTCCATCCCCACGGAGGCGCTCTCCCACCTGCACGGCCTCATCGT
CCTGCGGCTACGACATCTCAACATCAATGCCATCAGGGACTACTCCTTCAAGA
GGCTGTACCGACTTAAGGTCTTAGAGATCTCCCACTGGCCCTACCTGGACACCA
TGACCCCCAACTGCCTCTACGGCCTCAACCTGACATCCCTATCCATCACGCACT
GCAACCTGACAGCCGTGCCCTATCTGGCAGTGCGTCACCTGGTCTATCTCCGTT
TCCTCAACCTTTCCTACAACCCAATCGGTACAATCGAGGGCTCCATGCTGCATG
AGCTGCTGCGGTTGCAGGAGATCCAGCTGGTGGGCGGGCAGCTGGCCGTGGTG
GAGCCCTATGCCTTTCGTGGGCTCAACTACCTGCGTGTGCTCAATGTCTCTGGC
AACCAGCTGACCACCCTGGAGGAGTCAGCCTTCCATTCGGTGGGCAACCTGGA
GACGCTCATCCTGGACTCCAACCCACTGGCCTGTGACTGCCGGCTGCTGTGGGT
GTTCCGGCGCCGCTGGCGGCTCAACTTCAACAGGCAGCAGCCCACCTGCGCCA
CACCTGAGTTCGTCCAGGGCAAAGAGTTCAAGGACTTTCCGGATGTACTCCTA
CCCAACTACTTCACCTGCCGCCGGGCCCACATCCGGGACCGCAAGGCACAGCA
GGTGTTTGTAGATGAGGGCCACACGGTGCAGTTTGTATGCCGGGCAGATGGCG
ACCCTCCACCAGCTATCCTTTGGCTCTCACCCCGCAAGCACTTGGTCTCGGCCA
AGAGCAATGGGCGGCTCACAGTCTTCCCTGATGGCACGCTGGAGGTGCGCTAC
GCCCAGGTACAGGACAACGGCACGTACCTGTGCATCGCAGCCAATGCTGGCGG
CAACGACTCCATGCCCGCCCACTTGCATGTGCGCAGCTACTCGCCTGACTGGCC
CCATCAACCCAACAAGACCTTCGCCTTCATCTCCAACCAGCCAGGCGAGGGAG
AGGCCAACAGCACCCGCGCCACTGTGCCTTTCCCCTTCGACATCAAGACGCTC
ATTATCGCCACCACCATGGGCTTCATCTCCTTCCTGGGCGTTGTCCTATTCTGCC
TGGTGCTGCTGTTTCTATGGAGCCGGGGCAAAGGCAACACAAAGCACAACATC
GAAATTGAGTATGTGCCCCGGAAATCGGACGCAGGCATCAGCTCAGCTGATGC
ACCCCGCAAGTTCAACATGAAGATGATATGA

TREATMENT OF CONDITIONS INVOLVING DEMYELINATION

CROSS-REFERENCE TO RELATED APPLICATIONS

The present application claims the benefit of the filing dates of U.S. Provisional Application No. 60/680,475 filed May 13, 2005 and U.S. Provisional Application No. 60/628,435, filed Nov. 15, 2004, and U.S. Provisional Application No. 60/617,297, filed Oct. 7, 2004, and U.S. Provisional Application No. 60/582,966, filed Jun. 24, 2004, all of which are incorporated herein by reference in their entireties.

REFERENCE TO A SEQUENCE LISTING SUBMITTED ON A COMPACT DISC

This application includes a "Sequence Listing," which is provided as an electronic document on a compact disc (CD-R). This compact disc contains the file "Amended Sequence Listing.txt" (37 kilobytes, created on Apr. 3, 2008), which is hereby incorporated by reference in its entirety.

BACKGROUND OF THE INVENTION

1. Field of the Invention

This invention relates to neurobiology, neurology and pharmacology. More particularly, it relates to methods of treating demyelination and dysmyelination diseases, such as multiple sclerosis, by the administration of Sp35 antagonists.

2. Background Art

Many diseases of the nervous system are associated with demyelination and dysmyelination, including multiple sclerosis (MS), progressive multifocal leukoencephalopathy (PML), encephalomyelitis (EPL), central pontine myelinolysis (CPM), Wallerian Degeneration and some inherited diseases such as adrenoleukodystrophy, Alexander's disease, and Pelizaeus Merzbacher disease (PMZ). Among these diseases, MS is the most widespread, affecting approximately 2.5 million people worldwide.

MS generally begins with a relapsing-remitting pattern of neurologic involvement, which then progresses to a chronic phase with increasing neurological damage. MS is associated with the destruction of myelin, oligodendrocytes and axons localized to chronic lesions. The demyelination observed in MS is not always permanent and remyelination has been documented in early stages of the disease. Remyelination of neurons requires oligodendrocytes.

Various disease-modifying treatments are available for MS, including the use of corticosteroids and immunomodulators such as interferon beta. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., N. Engl. J. Med. 346:165-73 (2002). However, there remains an urgent need to devise additional therapies for MS.

BRIEF SUMMARY OF THE INVENTION

The present invention is based on the discovery that Sp35 (Sp35 is also designated in the literature as LINGO-1 and LRRN6) is expressed in oligodendrocytes and negatively regulates oligodendrocyte differentiation, survival and axon myelination. Furthermore, certain antagonists of Sp35 promote survival, proliferation and differentiation of oligodendrocytes as well as myelination of neurons. Based on these discoveries, the invention relates generally to methods of treating conditions associated with demyelination and dysmyelination (e.g. multiple sclerosis) by the administration of an Sp35 antagonist.

In certain embodiments, the invention includes a method for promoting proliferation, differentiation and survival of oligodendrocytes in a mammal, comprising administering a therapeutically effective amount of an Sp35 antagonist.

In other embodiments, the invention includes a method for promoting myelination of neurons in a mammal, comprising administering a therapeutically effective amount of a Sp35 antagonist. In certain embodiments, the mammal has been diagnosed with a disease, disorder, injury or condition involving demyelination and dysmyelination. In some embodiments, the disease, disorder, injury or condition is selected from the group consisting of multiple sclerosis (MS), progressive multifocal leukoencephalopathy (PML), encephalomyelitis (EPL), central pontine myelinolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy.

Additionally, the invention includes a method of treating a disease, disorder or injury in a mammal involving the destruction of oligodendrocytes or myelin, comprising (a) providing a cultured host cell expressing a recombinant Sp35 antagonist; and (b) introducing the host cell into the mammal at or near the site of the nervous system disease, disorder or injury. In some embodiments, the disease, disorder or injury is selected from the group consisting of multiple sclerosis (MS), progressive multifocal leukoencephalopathy (PML), encephalomyelitis (EPL), central pontine myelinolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. In some embodiments, the cultured host cell is derived from the mammal to be treated.

Further embodiments of the invention include a method of treating a disease, disorder or injury involving the destruction of oligodendrocytes or myelin by in vivo gene therapy, comprising administering to a mammal, at or near the site of the disease, disorder or injury, a vector comprising a nucleotide sequence that encodes an Sp35 antagonist so that the Sp35 antagonist is expressed from the nucleotide sequence in the mammal in an amount sufficient to reduce inhibition of axonal extension by neurons at or near the site of the injury. In certain embodiments, the vector is a viral vector which is selected from the group consisting of an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, and a herpes simplex viral vector. In some embodiments, the disease, disorder or injury is selected from the group consisting of multiple sclerosis (MS), progressive multifocal leukoencephalopathy (PML), encephalomyelitis (EPL), central pontine myelinolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. In some embodiments, the vector is administered by a route selected from the group consisting of topical administration, intraocular administration, parenteral administration, intrathecal administration, subdural administration and subcutaneous administration.

In various embodiments of the above methods, the Sp35 antagonist may be any molecule which interferes with ability of Sp35 to negatively regulate survival, proliferation and differentiation of oligodendrocytes as well as myelination of neurons. In certain embodiments, the Sp 35 antagonist is selected from the group consisting of a soluble Sp35 polypeptide, an Sp35 antibody and an Sp35 antagonist polynucleotide (e.g. RNA interference).

Certain soluble Sp35 polypeptides include, but are not limited to, Sp35 polypeptides fragments, variants, or derivative thereof which lack a transmembrane domain and a cytoplasmic domain. Soluble Sp35 polypeptides include polypeptides comprising (i) an Sp35 Leucine-Rich Repeat (LRR) domain, (ii) an Sp35 basic region C-terminal to the LRR domain, and (iii) an Sp 35 immunoglobulin (Ig) domain. In some embodiments, the soluble Sp35 polypeptide lacks an Sp35 Ig domain, an Sp35 LRR domain, a transmembrane domain, and a cytoplasmic domain. In some embodiments, the soluble Sp35 polypeptide comprises an Sp35 LRR domain and lacks an Sp35 Ig domain, an Sp35 basic region, a transmembrane domain, and a cytoplasmic domain. In some embodiments, the soluble Sp35 polypeptide comprises amino acid residues 34-532 of SEQ ID NO: 2.

In some embodiments, the Sp35 antagonist is administered by bolus injection or chronic infusion. In some embodiments, the soluble Sp35 polypeptide is administered directly into the central nervous system. In some embodiments, the soluble Sp35 polypeptide is administered directly into a chronic lesion of MS.

In some embodiments, the Sp35 antagonist is a fusion polypeptide comprising a non-Sp35 moiety. In some embodiments, the non-Sp35 moiety is selected from the group consisting of an antibody Ig moiety, a serum albumin moiety, a targeting moiety, a reporter moiety, and a purification-facilitating moiety. In some embodiments, the antibody Ig moiety is a hinge and Fc moiety.

In some embodiments, the polypeptides and antibodies of the present invention are conjugated to a polymer. In some embodiments, the polymer is selected from the group consisting of a polyalkylene glycol, a sugar polymer, and a polypeptide. In some embodiments, the polyalkylene glycol is polyethylene glycol (PEG). In some embodiments, the polypeptides and antibodies of the present invention are conjugated to 1, 2, 3 or 4 polymers. In some embodiments, the total molecular weight of the polymers is from 5,000 Da to 100,000 Da.

BRIEF DESCRIPTION OF THE DRAWINGS

FIG. 1 (A and B) is the nucleotide sequence of a full-length human Sp35 (SEQ ID NO: 80).

FIG. 2 is the amino acid sequence of a full-length human Sp35 polypeptide (SEQ ID NO: 2).

FIG. 3 is the nucleotide sequence of a sequence encoding a full-length mouse Sp35 polypeptide (SEQ ID NO:3).

FIG. 4 is the amino acid sequence of a full-length mouse Sp35 polypeptide (SEQ ID NO:4).

DETAILED DESCRIPTION OF THE INVENTION

Definitions

Figure 5:
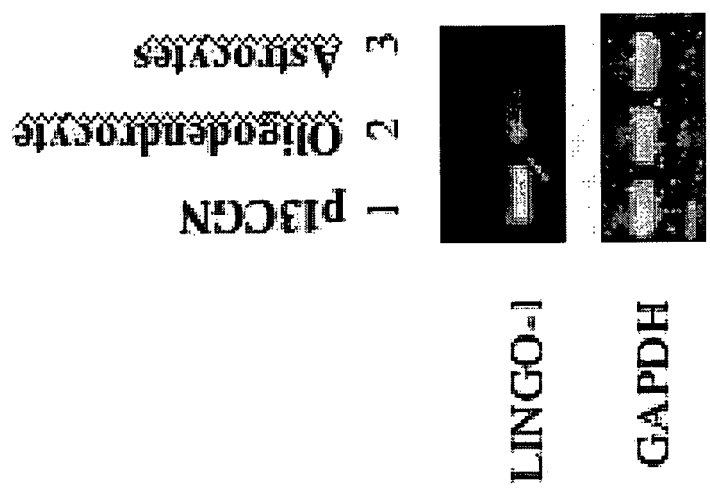
FIG. 5—Sp35 (LINGO-1) is expressed in oligodendrocytes. RT-PCR analysis of LINGO-1 mRNA expression in P13 CG neuronal (p13CGN), oligodendrocyte and astrocyte cultures. GAPDH expression was analyzed from the same samples as an internal control.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers.

As used herein, a "therapeutically effective amount" refers to an amount effective, at dosages and for periods of time necessary, to achieve a desired therapeutic result. A therapeutic result may be, e.g., lessening of symptoms, prolonged survival, improved mobility, and the like. A therapeutic result need not be a "cure".

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "polynucleotide" can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In the present invention, a polypeptide can be composed of amino acids joined to each other by peptide bonds or modified peptide bonds, i.e., peptide isosteres, and may contain amino acids other than the 20 gene-encoded amino acids (e.g. non-naturally occuring amino acids). The polypeptides of the present invention may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The terms "fragment," "variant," "derivative" and "analog" when referring to an Sp35 antagonist of the present invention include any antagonist molecules which retain at least some ability to inhibit Sp35 activity. Sp35 antagonists as described herein may include fragment, variant, or derivative molecules therein without limitation, so long as the Sp35 antagonist still serves its function. Soluble Sp35 polypeptides of the present invention may include Sp35 proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. Soluble Sp35 polypeptides of the present invention may comprise variant Sp35 regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. *Genes II*, Lewin, B., ed., John Wiley & Sons, New York (1985). Non-naturally occurring variants may be produced using art-known mutagenesis techniques. Soluble Sp35 polypeptides may comprise conservative or non-conservative amino acid substitutions, deletions or additions. Sp35 antagonists of the present invention may also include derivative molecules. For example, soluble Sp35 polypeptides of the present invention may include Sp35 regions which have been altered so as to exhibit additional features not found on the native polypeptide. Examples include fusion proteins and protein conjugates.

In the present invention, a "polypeptide fragment" refers to a short amino acid sequence of an Sp35 polypeptide. Protein fragments may be "free-standing," or comprised within a larger polypeptide of which the fragment forms a part of region. Representative examples of polypeptide fragments of the invention, include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids in length.

Antibody or Immunoglobulin.

In one embodiment, the Sp35 antagonists for use in the treatment methods disclosed herein are "antibody" or "immunoglobulin" molecules, or immunospecific fragments thereof, e.g., naturally occurring antibody or immunoglobulin molecules or engineered antibody molecules or fragments that bind antigen in a manner similar to antibody molecules. The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises five broad classes of polypeptides that can be distinguished biochemically. All five classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.,* 196: 901-917 (1987), which are incorporated herein by reference in their entireties).

In camelid species, however, the heavy chain variable region, referred to as $V_HH$, forms the entire CDR. The main differences between camelid $V_HH$ variable regions and those derived from conventional antibodies ($V_H$) include (a) more hydrophobic amino acids in the light chain contact surface of $V_H$ as compared to the corresponding region in $V_HH$, (b) a longer CDR3 in $V_HH$, and (c) the frequent occurrence of a disulfide bond between CDR1 and CDR3 in $V_HH$.

In one embodiment, an antigen binding molecule of the invention comprises at least one heavy or light chain CDR of an antibody molecule. In another embodiment, an antigen binding molecule of the invention comprises at least two CDRs from one or more antibody molecules. In another embodiment, an antigen binding molecule of the invention comprises at least three CDRs from one or more antibody molecules. In another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Exemplary antibody molecules comprising at least one CDR that can be included in the subject antigen binding molecules are known in the art and exemplary molecules are described herein.

Antibodies or immunospecific fragments thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to binding molecules disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In certain Sp35 antagonist antibodies or immunospecific fragments thereof for use in the treatment methods disclosed herein, the heavy chain portions of one polypeptide chain of a multimer are identical to those on a second polypeptide chain of the multimer. Alternatively, heavy chain portion-containing monomers for use in the methods of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a $C_H1$ domain derived from an $IgG_1$ molecule and a hinge region derived from an $IgG_3$ molecule. In another example, a heavy chain portion can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain portion" includes amino acid sequences derived from an immunoglobulin light chain. Preferably, the light chain portion comprises at least one of a $V_L$ or $C_L$ domain.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

Antibodies or immunospecific fragments thereof for use in the treatment methods disclosed herein may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Antibodies or immunospecific fragments thereof for use in the treatment methods disclosed herein act as antagonists of Sp35 as described herein. For example, an antibody for use in the methods of the present invention may function as an antagonist, blocking or inhibiting the suppressive activity of the Sp35 polypeptide.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

Sp35 (LINGO-1/LRRN6)

The invention is based on the discovery that antagonists of Sp35 increase oligodendrocyte numbers by promoting their survival, proliferation and differentiation. In addition, the inventors have discovered that antagonists of Sp35 promote myelination of neurons. Without intending to be bound by theory, it appears that the myelination-promoting activity produced by Sp35 antagonists is separate from the effects on oligodendrocyte proliferation.

Naturally occurring human Sp35 is a glycosylated nervous-system-specific protein consisting of 614 amino acids (FIG. 2; SEQ ID NO: 2). The human Sp35 polypeptide contains an LRR domain consisting of 14 leucine-rich repeats (including N- and C-terminal caps), an Ig domain, a transmembrane region, and a cytoplasmic domain (FIG. 2). The cytoplasmic domain contains a canonical tyrosine phosphorylation site. In addition, the naturally occurring Sp35 protein contains a signal sequence, a short basic region between the LRRCT and Ig domain, and a transmembrane region between the Ig domain and the cytoplasmic domain (FIG. 2). The human Sp35 gene contains alternative translation start codons, so that six additional amino acids (MQVSKR; SEQ ID NO:5) may or may not be present at the N-terminus of the Sp35 signal sequence. Table 1 lists the Sp35 domains and other regions, according to amino acid residue number, based on the sequence in FIG. 2.

TABLE 1

| Domain or Region | Beginning Residue | Ending Residue |
|---|---|---|
| Signal Sequence | 1 | 33 or 35 |
| LRRNT | 34 or 36 | 64 |
| LRR | 66 | 89 |
| LRR | 90 | 113 |
| LRR | 114 | 137 |
| LRR | 138 | 161 |
| LRR | 162 | 185 |
| LRR | 186 | 209 |
| LRR | 210 | 233 |
| LRR | 234 | 257 |
| LRR | 258 | 281 |
| LRR | 282 | 305 |
| LRR | 306 | 329 |
| LRR | 330 | 353 |
| LRRCT | 363 | 414 or 416 |
| Basic | 415 or 417 | 424 |
| Ig | 419 | 493 |
| Connecting sequence | 494 | 551 |
| Transmembrane | 552 | 576 |
| Cytoplasmic | 577 | 614 |

Tissue distribution and developmental expression of Sp35 have been studied in humans and rats. Sp35 biology has been studied in an experimental animal (rat) model. Expression of rat Sp35 is localized to nervous-system neurons and brain oligodendrocytes, as determined by northern blot and immuno-histochemical staining. Rat Sp35 mRNA expression level is regulated developmentally, peaking shortly after birth, i.e., ca. postnatal day one. In a rat spinal cord transection injury model, Sp35 is up-regulated at the injury site, as determined by RT-PCR. In addition, Sp35 has been shown to interact with Nogo66 Receptor (Nogo receptor). See, e.g., International Patent Application No. PCT/US2004/00832. However, Nogo receptor-1 is not expressed on oligodendrocytes and any impact of Sp35 on oligodendrocyte biology must occur by a Nogo-receptor-independent pathway.

Treatment Methods Using Antagonists of Sp35

One embodiment of the present invention provides methods for treating a disease, disorder or injury associated with dysmyelination or demyelination, e.g., multiple sclerosis in an animal suffering from such disease, the method comprising, consisting essentially of, or consisting of administering to the animal an effective amount of an Sp35 antagonist selected from the group consisting of a soluble Sp35 polypeptide, an Sp35 antibody and an Sp35 antagonist polynucleotide.

Additionally, the invention is directed to a method for promoting myelination of neurons in a mammal comprising, consisting essentially of, or consisting of administering a therapeutically effective amount of an Sp35 antagonist selected from the group consisting of a soluble Sp35 polypeptide, an Sp35 antibody and an Sp35 antagonist polynucleotide.

An additional embodiment of the present invention provides methods for treating a disease, disorder or injury associated with oligodendrocyte death or lack of differentiation, e.g., multiple sclerosis, Pelizaeus Merzbacher disease or globoid cell leukodystrophy (Krabbe's disease), in an animal suffering from such disease, the method comprising, consisting essentially of, or consisting of administering to the animal an effective amount of an Sp35 antagonist selected from the group consisting of a soluble Sp35 polypeptide, an Sp35 antibody and an Sp35 antagonist polynucleotide.

Another aspect of the invention includes a method for promoting proliferation, differentiation and survival of oligodendrocytes in a mammal comprising, consisting essentially of, or consisting of administering a therapeutically effective amount of an Sp35 antagonist selected from the group consisting of a soluble Sp35 polypeptide, an Sp35 antibody and an Sp35 antagonist polynucleotide.

An Sp35 antagonist, e.g., a soluble Sp35 polypeptide, an Sp35 antibody or an Sp35 antagonist polynucleotide, to be used in treatment methods disclosed herein, can be prepared and used as a therapeutic agent that stops, reduces, prevents, or inhibits the ability of Sp35 to negatively regulate myelination of neurons by oligodendrocytes. Additionally, the Sp35 antagonist to be used in treatment methods disclosed herein can be prepared and used as a therapeutic agent that stops, reduces, prevents, or inhibits the ability of Sp35 to negatively regulate oligodendrocyte differentiation, proliferation and survival.

Further embodiments of the invention include a method of inducing oligodendrocyte proliferation or survival to treat a disease, disorder or injury involving the destruction of oligodendrocytes or myelin comprising administering to a mammal, at or near the site of the disease, disorder or injury, in an amount sufficient to reduce inhibition of axonal extension and promote myelination.

In methods of the present invention, an Sp35 antagonist can be administered via direct administration of a soluble Sp35 polypeptide, Sp35 antibody or Sp35 antagonist polynucleotide to the patient. Alternatively, the Sp35 antagonist can be administered via an expression vector which produces the specific Sp35 antagonist. In certain embodiments of the invention, an Sp35 antagonist is administered in a treatment method that includes: (1) transforming or transfecting an implantable host cell with a nucleic acid, e.g., a vector, that expresses an Sp35 antagonist; and (2) implanting the transformed host cell into a mammal, at the site of a disease, disorder or injury. For example, the transformed host cell can be implanted at the site of a chronic lesion of MS. In some embodiments of the invention, the implantable host cell is removed from a mammal, temporarily cultured, transformed or transfected with an isolated nucleic acid encoding an Sp35 antagonist, and implanted back into the same mammal from which it was removed. The cell can be, but is not required to be, removed from the same site at which it is implanted. Such embodiments, sometimes known as ex vivo gene therapy, can provide a continuous supply of the Sp35 antagonist, localized at the site of action, for a limited period of time.

Diseases or disorders which may be treated or ameliorated by the methods of the present invention include diseases, disorders or injuries which relate to dysmyelination or demyelination of mammalian neurons. Specifically, diseases and disorders in which the myelin which surrounds the neuron is either absent, incomplete, not formed properly or is deteriorating. Such disease include, but are not limited to, multiple sclerosis (MS) including relapsing remitting, secondary progressive and primary progressive forms of MS; progressive multifocal leukoencephalopathy (PML), encephalomyelitis (EPL), central pontine myelinolysis (CPM), adrenoleukodystrophy, Alexander's disease, Pelizaeus Merzbacher disease (PMZ), globoid cell leukodystrophy (Krabbe's disease), Wallerian Degeneration, optic neuritis and transvere myelitis.

Diseases or disorders which may be treated or ameliorated by the methods of the present invention include diseases, disorders or injuries which relate to the death or lack of proliferation or differentiation of oligodendrocytes. Such disease include, but are not limited to, multiple sclerosis (MS), progressive multifocal leukoencephalopathy (PML), encephalomyelitis (EPL), central pontine myelinolysis (CPM), adrenoleukodystrophy, Alexander's disease, Pelizaeus Merzbacher disease (PMZ), globoid cell leukodystrophy (Krabbe's disease) and Wallerian Degeneration.

Diseases or disorders which may be treated or ameliorated by the methods of the present invention include neurodegenerate disease or disorders. Such diseases include, but are not limited to, amyotrophic lateral sclerosis, Huntington's disease, Alzheimer's disease and Parkinson's disease.

Examples of additional diseases, disorders or injuries which may be treated or ameliorated by the methods of the present invention include, but are not limited, to spinal cord injuries, chronic myelopathy or rediculopathy, tramatic brain injury, motor neuron disease, axonal shearing, contusions, paralysis, post radiation damage or other neurological complications of chemotherapy, stroke, large lacunes, medium to large vessel occlusions, leukoariaosis, acute ischemic optic neuropathy, vitamin E deficiency (isolated deficiency syndrome, AR, Bassen-Komzweig syndrome), B12, B6 (pyridoxine-pellagra), thiamine, folate, nicotinic acid deficiency, Marchiafava-Bignami syndrome, Metachromatic Leukodystrophy, Trigeminal neuralgia, Bell's palsy, or any neural injury which would require axonal regeneration, remylination or oligodendrocyte survival or differentiation/proliferation.

Soluble Sp35 Polypeptides

Sp35 antagonists of the present invention include those polypeptides which block, inhibit or interfere with the biological function of naturally occurring Sp35. Specifically, soluble Sp35 polypeptides of the present invention include fragments, variants, or derivative thereof of a soluble Sp35 polypeptide. Table 1 above describes the various domains of the Sp35 polypeptide. Soluble Sp35 polypeptides lack the intracellular and transmembrane domains of the Sp35 polypeptide. For example, certain soluble Sp35 polypeptides lack amino acids 552-576 which comprise the transmembrane domain of Sp35 and/or amino acids 577-614 which comprise the intracellular domain of Sp35. Additionally, certain soluble Sp35 polypeptides comprise the LRR domains, Ig domain, basic region and/or the entire extracellular domain (corresponding to amino acids 34 to 532 of SEQ ID NO: 2) of the Sp35 polypeptide. As one of skill in the art would appreciate, the entire extracellular domain of Sp35 may comprise additional or fewer amino acids on either the C-terminal or N-terminal end of the extracellular domain polypeptide. As such, soluble Sp35 polypeptides for use in the methods of the present invention include, but are not limited to, an Sp35 polypeptide comprising, consisting essentially of, or consisting of amino acids 41 to 525 of SEQ ID NO:2; 40 to 526 of SEQ ID NO:2; 39 to 527 of SEQ ID NO:2; 38 to 528 of SEQ ID NO:2; 37 to 529 of SEQ ID NO:2; 36 to 530 of SEQ ID NO:2; 35 to 531 of SEQ ID NO:2; 34 to 531 of SEQ ID NO:2; 46 to 520 of SEQ ID NO:2; 45 to 521 of SEQ ID NO:2; 44 to 522 of SEQ ID NO:2; 43 to 523 of SEQ ID NO:2; and 42 to 524 of SEQ ID NO:2 or fragments, variants, or derivatives of such polypeptides. Sp35 polypeptide antagonists may include any combination of domains as described in Table 1.

Additional soluble Sp35 polypeptides for use in the methods of the present invention include, but are not limited to, an Sp35 polypeptide comprising, consisting essentially of, or consisting of amino acids 1 to 33 of SEQ ID NO:2; 1 to 35 of SEQ ID NO:2; 34 to 64 of SEQ ID NO:2; 36 to 64 of SEQ ID NO:2; 66 to 89 of SEQ ID NO:2; 90 to 113 of SEQ ID NO:2; 114 to 137 of SEQ ID NO:2; 138 to 161 of SEQ ID NO:2; 162 to 185 of SEQ ID NO:2; 186 to 209 of SEQ ID NO:2; 210 to 233 of SEQ ID NO:2; 234 to 257 of SEQ ID NO:2; 258 to 281 of SEQ ID NO:2; 282 to 305 of SEQ ID NO:2; 306 to 329 of SEQ ID NO:2; 330 to 353 of SEQ ID NO:2; 363 to 416 of SEQ ID NO:2; 417 to 424 of SEQ ID NO:2; 419 to 493 of SEQ ID NO:2; and 494 to 551 of SEQ ID NO:2 or fragments, variants, or derivatives of such polypeptides.

Further soluble Sp35 polypeptides for use in the methods of the present invention include, but are not limited to, an Sp35 polypeptide comprising, consisting essentially of, or consisting of amino acids 1 to 33 of SEQ ID NO:2; 1 to 35 of SEQ ID NO:2; 1 to 64 of SEQ ID NO:2; 1 to 89 of SEQ ID NO:2; 1 to 113 of SEQ ID NO:2; 1 to 137 of SEQ ID NO:2; 1 to 161 of SEQ ID NO:2; 1 to 185 of SEQ ID NO:2; 1 to 209 of SEQ ID NO:2; 1 to 233 of SEQ ID NO:2; 1 to 257 of SEQ ID NO:2; 1 to 281 of SEQ ID NO:2; 1 to 305 of SEQ ID NO:2; 1 to 329 of SEQ ID NO:2; 1 to 353 of SEQ ID NO:2; 1 to 416 of SEQ ID NO:2; 1 to 424 of SEQ ID NO:2; 1 to 493 of SEQ ID NO:2; 1 to 551 of SEQ ID NO:2; 1 to 531 of SEQ ID NO:2 and 1 to 532 of SEQ ID NO:2 or fragments, variants, or derivatives of such polypeptides.

Still further soluble Sp35 polypeptides for use in the methods of the present invention include, but are not limited to, an Sp35 polypeptide comprising, consisting essentially of, or consisting of amino acids 34 to 64 of SEQ ID NO:2; 34 to 89 of SEQ ID NO:2; 34 to 113 of SEQ ID NO:2; 34 to 137 of SEQ ID NO:2; 34 to 161 of SEQ ID NO:2; 34 to 185 of SEQ ID NO:2; 34 to 209 of SEQ ID NO:2; 34 to 233 of SEQ ID NO:2; 34 to 257 of SEQ ID NO:2; 34 to 281 of SEQ ID NO:2; 34 to 305 of SEQ ID NO:2; 34 to 329 of SEQ ID NO:2; 34 to 353 of SEQ ID NO:2; 34 to 416 of SEQ ID NO:2; 34 to 424 of SEQ ID NO:2; 34 to 493 of SEQ ID NO:2; and 34 to 551 of SEQ ID NO:2 or fragments, variants, or derivatives of such polypeptides.

Additional soluble Sp35 polypeptides for use in the methods of the present invention include, but are not limited to, an Sp35 polypeptide comprising, consisting essentially of, or consisting of amino acids 34 to 530 of SEQ ID NO:2; 34 to 531 of SEQ ID NO:2; 34 to 532 of SEQ ID NO:2; 34 to 533 of SEQ ID NO:2; 34 to 534 of SEQ ID NO:2; 34 to 535 of SEQ ID NO:2; 34 to 536 of SEQ ID NO:2; 34 to 537 of SEQ ID NO:2; 34 to 538 of SEQ ID NO:2; 34 to 539 of SEQ ID NO:2; 30 to 532 of SEQ ID NO:2; 31 to 532 of SEQ ID NO:2; 32 to 532 of SEQ ID NO:2; 33 to 532 of SEQ ID NO:2; 34 to 532 of SEQ ID NO:2; 35 to 532 of SEQ ID NO:2; 36 to 532 of SEQ ID NO:2; 30 to 531 of SEQ ID NO:2; 31 to 531 of SEQ ID NO:2; 32 to 531 of SEQ ID NO:2; 33 to 531 of SEQ ID NO:2; 34 to 531 of SEQ ID NO:2; 35 to 531 of SEQ ID NO:2; and 36 to 531 of SEQ ID NO:2 or fragments, variants, or derivatives of such polypeptides.

Still further soluble Sp35 polypeptides for use in the methods of the present invention include, but are not limited to, an Sp35 polypeptide comprising, consisting essentially of, or consisting of amino acids 36 to 64 of SEQ ID NO:2; 36 to 89 of SEQ ID NO:2; 36 to 113 of SEQ ID NO:2; 36 to 137 of SEQ ID NO:2; 36 to 161 of SEQ ID NO:2; 36 to 185 of SEQ ID NO:2; 36 to 209 of SEQ ID NO:2; 36 to 233 of SEQ ID NO:2; 36 to 257 of SEQ ID NO:2; 36 to 281 of SEQ ID NO:2; 36 to 305 of SEQ ID NO:2; 36 to 329 of SEQ ID NO:2; 36 to 353 of SEQ ID NO:2; 36 to 416 of SEQ ID NO:2; 36 to 424 of SEQ ID NO:2; 36 to 493 of SEQ ID NO:2; and 36 to 551 of SEQ ID NO:2 or fragments, variants, or derivatives of such polypeptides.

Additional soluble Sp35 polypeptides for use in the methods of the present invention include, but are not limited to, an Sp35 polypeptide comprising, consisting essentially of, or consisting of amino acids 36 to 530 of SEQ ID NO:2; 36 to 531 of SEQ ID NO:2; 36 to 532 of SEQ ID NO:2; 36 to 533 of SEQ ID NO:2; 36 to 534 of SEQ ID NO:2; 36 to 535 of SEQ ID NO:2; 36 to 536 of SEQ ID NO:2; 36 to 537 of SEQ ID NO:2; 36 to 538 of SEQ ID NO:2; and 36 to 539 of SEQ ID NO:2; or fragments, variants, or derivatives of such polypeptides.

Additional soluble Sp35 polypeptides, fragments, variants or derivatives thereof include polypeptides comprising the Ig domain of Sp35. For example, an Sp35 polypeptide comprising, consisting essentially of, or consisting of amino acids 417 to 493 of SEQ ID NO:2; 417 to 494 of SEQ ID NO:2; 417 to 495 of SEQ ID NO:2; 417 to 496 of SEQ ID NO:2; 417 to 497 of SEQ ID NO:2; 417 to 498 of SEQ ID NO:2; 417 to 499 of SEQ ID NO:2; 417 to 500 of SEQ ID NO:2; 417 to 492 of SEQ ID NO:2; 417 to 491 of SEQ ID NO:2; 412 to 493 of SEQ ID NO:2; 413 to 493 of SEQ ID NO:2; 414 to 493 of SEQ ID NO:2; 415 to 493 of SEQ ID NO:2; 416 to 493 of SEQ ID NO:2; 411 to 493 of SEQ ID NO:2; 410 to 493 of SEQ ID NO:2; 410 to 494 of SEQ ID NO:2; 411 to 494 of SEQ ID NO:2; 412 to 494 of SEQ ID NO:2; 413 to 494 of SEQ ID NO:2; 414 to 494 of SEQ ID NO:2; 415 to 494 of SEQ ID NO:2; 416 to 494 of SEQ ID NO:2; 417 to 494 of SEQ ID NO:2; and 418 to 494 of SEQ ID NO:2 or fragments, variants, or derivatives of such polypeptides.

Additional soluble Sp35 polypeptides for use in the methods of the present invention include an Sp35 polypeptide comprising, consisting essentially of, or consisting of peptides of the Ig domain of Sp35 or fragments, variants, or derivatives of such polypeptides. Specifically, polypeptides comprising, consisting essentially of, or consisting of the following polypeptide sequences: ITX$_1$X$_2$X$_3$ (SEQ ID NO:6), ACX$_1$X$_2$X$_3$ (SEQ ID NO:7), VCX$_1$X$_2$X$_3$ (SEQ ID NO:8) and SPX$_1$X$_2$X$_3$ (SEQ ID NO:9) where X$_1$ is lysine, arginine, histidine, glutamine, or asparagine, X$_2$ is lysine, arginine, histidine, glutamine, or asparagine and X$_3$ is lysine, arginine, histidine, glutamine, or asparagine. For example, Sp35 Ig domain antagonist peptides include a polypeptide comprising, consisting essentially of, or consisting of the following polypeptide sequences: SPRKH (SEQ ID NO:10), SPRKK (SEQ ID NO:11), SPRKR (SEQ ID NO:12), SPKKH (SEQ ID NO:13), SPHKH (SEQ ID NO:14), SPRRH (SEQ ID NO:15), SPRHH (SEQ ID NO:16), SPRRR (SEQ ID NO:17), SPHHH (SEQ ID NO:18) SPKKK (SEQ ID NO:19), LSPRKH (SEQ ID NO:61), LSPRKK (SEQ ID NO: 80), LSPRKR (SEQ ID NO: 81), LSPKKH (SEQ ID NO:82), LSPHKH (SEQ ID NO:83), LSPRRH (SEQ ID NO: 84), LSPRHH (SEQ ID NO:85) LSPRRR (SEQ ID NO:86), LSPHHH (SEQ ID NO: 87), LSPKKK (SEQ ID NO:88), WLSPRKH (SEQ ID NO:89), WLSPRKK (SEQ ID NO:90), WLSPRKR (SEQ ID NO: 91), WLSPHKH (SEQ ID NO: 92), WLSPHKH (SEQ ID NO:93) WLSPRRH (SEQ ID NO:94, WLSPHHH (SEQ ID NO:95), WLSPRRR (SEQ ID NO:96), WLSPHHH (SEQ ID NO:97) WLSPKKK (SEQ ID NO:98). These soluble Sp35 polypeptides include the basic "RKH loop" (Arginine-Lysine-Histidine amino acids 456-458) in the Ig domain of Sp35. This basic tripeptide is thought to be important for soluble Sp35 antagonist polypeptide binding to the native Sp35 polypeptide. Additional soluble Sp35 peptides which include a basic tripeptide are ITPKRR (SEQ ID NO:20), ACHHK (SEQ ID NO:21) and VCHHK (SEQ ID NO:22).

Additional soluble Sp35 polypeptides for use in the methods of the present invention include an Sp35 polypeptide comprising, consisting essentially of, or consisting of peptides of the Ig domain of Sp35 or fragments, variants, or derivatives of such polypeptides. Specifically, peptide comprising, consisting essentially of, or consisting of the following polypeptide sequences: X$_4$X$_5$RKH (SEQ ID NO:23), X$_4$X$_5$RRR (SEQ ID NO:24), X$_4$X$_5$KKK (SEQ ID NO:25), X$_4$X$_5$HHH (SEQ ID NO:26), X$_4$X$_5$RKK (SEQ ID NO:27), X$_4$X$_5$RKR (SEQ ID NO:28), X$_4$X$_5$KKH (SEQ ID NO:29), X$_4$X$_5$HKH (SEQ ID NO:30), X$_4$X$_5$RRH (SEQ ID NO:31) and X$_4$X$_5$RHH (SEQ ID NO:32) where X$_4$ is any amino acid and X$_5$ is any amino acid.

In other embodiments soluble Sp35 polypeptides for use in the methods of the present invention include an Sp35 polypeptide comprising, consisting essentially of, or consisting of peptides of the Ig domain of Sp35 or fragments, variants, or derivatives of such polypeptides. Specifically, polypeptides comprising, consisting essentially of, or consisting of the following polypeptide sequences: ITX$_6$X$_7$X$_8$ (SEQ ID NO:68), ACX$_6$X$_7$X$_8$ (SEQ ID NO:69), VCX$_6$X$_7$X$_8$ (SEQ ID NO:70) and SPX$_6$X$_7$X$_8$ (SEQ ID NO:71) where X$_6$ is lysine, arginine, histidine, glutamine, or asparagine, X$_7$ is any amino acid and X$_8$ is lysine, arginine, histidine, glutamine, or asparagine. For example, Sp35 Ig domain antagonist peptides include a polypeptide comprising, consisting essentially of, or consisting of the following polypeptide sequence: SPRLH (SEQ ID NO:72).

In other embodiments of the present invention, the soluble Sp35 polypeptides for use in the methods of the present invention include an Sp35 polypeptide comprising, consisting essentially of, or consisting of peptides which contain amino acids 452-458 in the Ig domain of Sp35, or derivatives thereof, wherein amino acid 452 is a tryptophan or phenylalanine residue.

Additional soluble Sp35 polypeptides for use in the methods of the present invention include an Sp35 polypeptide comprising, consisting essentially of, or consisting of peptides of the basic domain of Sp35. Specifically, peptides comprising, consisting essentially of, or consisting of the following polypeptide sequences: RRARIRDRK (SEQ ID NO:33), KKVKVKEKR (SEQ ID NO:34), RRLRLRDRK (SEQ ID NO:35), RRGRGRDRK (SEQ ID NO:36) and RRIRARDRK (SEQ ID NO:37).

Various exemplary soluble Sp35 polypeptides and methods and materials for obtaining these molecules for practicing the present invention are described below and/or may be found, e.g., in International Patent Application No. PCT/US2004/008323, incorporated herein by reference in its entirety.

Soluble Sp35 polypeptides for use in the methods of the present invention described herein may be cyclic. Cyclization of the soluble Sp35 polypetides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two ω-thio amino acid residues (e.g. cysteine, homocysteine). Certain soluble Sp35 peptides of the present invention include modifications on the N- and C-terminus of the peptide to form a cyclic Sp35 polypeptide. Such modifications include, but are not limited, to cysteine residues, acetylated cysteine residues cystein residues with a NH$_2$ moiety and biotin. Other methods of peptide cyclization are described in Li & Roller. *Curr. Top. Med. Chem.* 3:325-341 (2002), which is incorporated by reference herein in its entirety.

Cyclic Sp35 polypeptides for use in the methods of the present invention described herein include, but are not limited to, C$_1$LSPX$_9$X$_{10}$X$_{11}$C$_2$ (SEQ ID NO:99) where X$_9$ is lysine, arginine, histidine, glutamine, or asparagine, $X_{10}$ is lysine, arginine, histidine, glutamine, or asparagine, $X_{11}$ is lysine, arginine, histidine, glutamine, or asparagine, $C_1$ optionally has a moiety to promote cyclization (e.g. an acetyl group or biotin) attached and $C_2$ optionally has a moiety to promote cyclization (e.g. an $NH_2$ moiety) attached.

Soluble Sp35 polypeptides described herein may have various alterations such as substitutions, insertions or deletions. For examples, substitutions include, but are not limited to the following substitutions: valine at position 6 of the Sp35 polypeptide of SEQ ID NO:2 to methionine; serine at position 294 of the Sp35 polypeptide of SEQ ID NO:2 to glycine; valine at positon 348 of the Sp35 polypeptide of SEQ ID NO:2 to alanine; arginine at position 419 of the Sp35 polypeptide to histidine; arginine at position 456 to glutamic acid; and histidine at position 458 of SEQ ID NO:2 to valine.

Corresponding fragments of soluble Sp35 polypeptides at least 70%, 75%, 80%, 85%, 90%, or 95% identical to polypeptides of SEQ ID NO:2 described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Soluble Sp35 polypeptides for use in the methods of the present invention may include any combination of two or more soluble Sp35 polypeptides.

Antibodies or Immunospecific Fragments Thereof

Sp35 antagonists for use in the methods of the present invention also include Sp35-specific antibodies or antigen-binding fragments, variants, or derivatives which are antagonists of Sp35 activity. For example, binding of certain Sp35 antibodies to Sp35, as expressed on oligodendrocytes, blocks inhibition of oligodendrocyte growth or differentiation, or blocks demyelination or dysmyelination of CNS neurons.

Certain antagonist antibodies for use in the methods described herein specifically or preferentially binds to a particular Sp35 polypeptide fragment or domain. Such Sp35 polypeptide fragments include, but are not limited to, an Sp35 polypeptide comprising, consisting essentially of, or consisting of amino acids 34 to 532; 34 to 417, 34 to 425, 34 to 493, 66 to 532, 66 to 417 (LRR domain), 66 to 426, 66 to 493, 66 to 532, 417 to 532, 417 to 425 (the Sp35 basic region), 417 to 424 (the Sp35 basic region), 417 to 493, 417 to 532, 419 to 493 (the Sp35 Ig region), or 425 to 532 of SEQ ID NO:2, or an Sp35 variant polypeptide at least 70%, 75%, 80%, 85%, 90%, or 95% identical to amino acids 34 to 532; 34 to 417, 34 to 425, 34 to 493, 66 to 532, 66 to 417, 66 to 426, 66 to 493, 66 to 532, 417 to 532, 417 to 425 (the Sp35 basic region), 417 to 493, 417 to 532, 419 to 493 (the Sp35 Ig region), or 425 to 532 of SEQ ID NO:2.

Additional Sp35 peptide fragments to which certain Sp35 specific antibodies, or antigen-binding fragments, variants, or derivatives thereof of the present invention bind include, but are not limited to, those fragments comprising, consisting essentially of, or consisting of one or more leucine-rich-repeats (LRR) of Sp35. Such fragments, include, for example, fragments comprising, consisting essentially of, or consisting of amino acids 66 to 89, 66 to 113, 66 to 137, 90 to 113, 114 to 137, 138 to 161, 162 to 185, 186 to 209, 210 to 233, 234 to 257, 258 to 281, 282 to 305, 306 to 329, or 330 to 353 of SEQ ID NO:2. Corresponding fragments of a variant Sp35 polypeptide at least 70%, 75%, 80%, 85%, 90%, or 95% identical to amino acids 66 to 89, 66 to 113, 90 to 113, 114 to 137, 138 to 161, 162 to 185, 186 to 209, 210 to 233, 234 to 257, 258 to 281, 282 to 305, 306 to 329, or 330 to 353 of SEQ ID NO:2 are also contemplated.

Additional Sp35 peptide fragments to which certain antibodies, or antigen-binding fragments, variants, or derivatives thereof of the present invention bind include, but are not limited to those fragments comprising, consisting essentially of, or consisting of one or more cysteine rich regions flanking the LRR of Sp35. Such fragments, include, for example, a fragment comprising, consisting essentially of, or consisting of amino acids 34 to 64 of SEQ ID NO:2 (the N-terminal LRR flanking region (LRRNT)), or a fragment comprising, consisting essentially of, or consisting of amino acids 363 to 416 of SEQ ID NO:2 (the C-terminal LRR flanking region (LRRCT)). Corresponding fragments of a variant Sp35 polypeptide at least 70%, 75%, 80%, 85%, 90%, or 95% identical to amino acids 34 to 64 and 363 to 416 of SEQ ID NO:2 are also contemplated.

In other embodiments, the present invention includes an antibody, or antigen-binding fragment, variant, or derivative thereof which specifically or preferentially binds to at least one epitope of Sp35, where the epitope comprises, consists essentially of, or consists of at least about four to five amino acids of SEQ ID NO:2, at least seven, at least nine, or between at least about 15 to about 30 amino acids of SEQ ID NO:2. The amino acids of a given epitope of SEQ ID NO:2 as described may be, but need not be contiguous or linear. In certain embodiments, the at least one epitope of Sp35 comprises, consists essentially of, or consists of a non-linear epitope formed by the extracellular domain of Sp35 as expressed on the surface of a cell or as a soluble fragment, e.g., fused to an IgG Fc region. Thus, in certain embodiments the at least one epitope of Sp35 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

In other embodiments, the present invention includes an antibody, or antigen-binding fragment, variant, or derivative thereof which specifically or preferentially binds to at least one epitope of Sp35, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the Sp35 antibody binds with higher affinity to modified target protein than it does to an unmodified version of the protein. Alternatively, the Sp35 antibody does not bind the unmodified version of the target protein at all.

In certain embodiments, an antibody, or antigen-binding fragment, variant, or derivative thereof of the invention binds specifically to at least one epitope of Sp35 or fragment or variant described above, i.e., binds to such an epitope more readily than it would bind to an unrelated, or random epitope; binds preferentially to at least one epitope of Sp35 or fragment or variant described above, i.e., binds to such an epitope more readily than it would bind to a related, similar, homologous, or analogous epitope; competitively inhibits binding of a reference antibody which itself binds specifically or preferentially to a certain epitope of Sp35 or fragment or variant described above; or binds to at least one epitope of Sp35 or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-11}$ M, about $10^{-13}$ M, about $5\times10^{-11}$ M, about $10^{-14}$ M, about $5\times10^{-15}$ M, or about $10^{-15}$ M. In a particular aspect, the antibody or fragment thereof preferentially binds to a human Sp35 polypeptide or fragment thereof, relative to a murine Sp35 polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds Sp35 polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof of the invention binds binds Sp35 polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, an antibody, or antigen-binding fragment, variant, or derivative thereof of the invention binds Sp35 polypeptides or fragments or variants thereof with an on rate (k(on)) of greater than or equal to $10^{3}$ M$^{-1}$ sec$^{-1}$, $5\times10^{3}$ M$^{-1}$ sec$^{-1}$, $10^{4}$ M$^{-1}$ sec$^{-1}$ or $5\times10^{4}$ M$^{-1}$ sect$^{-1}$. Alternatively, an antibody, or antigen-binding fragment, variant, or derivative thereof of the invention binds Sp35 polypeptides or fragments or variants thereof with an on rate (k(on)) greater than or equal to $10^{5}$ M$^{-1}$ sec$^{-1}$, $5\times10^{5}$ M$^{-1}$ sec$^{-1}$, $10^{6}$ M$^{-1}$ sec$^{-1}$, or $5\times10^{6}$ M$^{-1}$ sec$^{-1}$ or $10^{7}$ M$^{-1}$ sec$^{-1}$.

In one embodiment, a Sp35 antagonist for use in the methods of the invention is an antibody molecule, or immunospecific fragment thereof. Unless it is specifically noted, as used herein a "fragment thereof" in reference to an antibody refers to an immunospecific fragment, i.e., an antigen-specific fragment. In one embodiment, an antibody of the invention is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on Sp35. A bispecific antibody may be a tetravalent antibody that has two target binding domains specific for an epitope of Sp35 and two target binding domains specific for a second target. Thus, a tetravalent bispecific antibody may be bivalent for each specificity.

In certain embodiments of the present invention comprise administration of an Sp35 antagonist antibody, or immunospecific fragment thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain Sp35 antagonist antibodies or immunospecific fragments thereof for use in the therapeutic methods described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of antibodies or immunospecific fragments thereof for use in the diagnostic and therapeutic methods disclosed herein can be made from whole precursor or parent antibodies using techniques known in the art. Exemplary techniques are discussed in more detail herein.

In certain embodiments both the variable and constant regions of Sp35 antagonist antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human anti bodies can likewise be produced by various display technologies, e.g., phage display or other viral display systems, as described in more detail elsewhere herein.

Sp35 antagonist antibodies or immunospecific fragments thereof for use in the diagnostic and treatment methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Sp35 antagonist antibodies or immunospecific fragments thereof for use in the treatment methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In preferred embodiments, an Sp35 antagonist antibody or immunospecific fragment thereof for use in the treatment methods disclosed herein will not elicit a deleterious immune response in the animal to be treated, e.g., in a human. In one embodiment, Sp35 antagonist antibodies or immunospecific fragments thereof for use in the treatment methods disclosed herein be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., Sp35 antagonist antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Sp35 antagonist antibodies or fragments thereof for use in the methods of the present invention may be generated by any suitable method known in the art. Polyclonal antibodies can be produced by various procedures well known in the art. For example, a Sp35 immunospecific fragment can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified Sp35 antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969, 108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a Sp35 polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., *BioTechniques* 4:214 (1986); Gillies et al., *J. Immunol. Methods* 125:191-202 (1989); U.S. Pat. Nos.

5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988)). See also, U.S. Pat. No. 5,565,332.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., Sp35. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242:1038-1041 (1988)).

Sp35 antagonist antibodies may also be human or substantially human antibodies generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the therapeutic methods disclosed herein can be produced by any method known in the art for the synthesis of antibodies, in particular, by chemical synthesis or preferably, by recombinant expression techniques as described herein.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Recombinant expression of an antibody, or fragment, derivative or analog thereof, e.g., a heavy or light chain of an antibody which is an Sp35 antagonist, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli*, *B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Prolocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. 2002 0123057 A1.

In one embodiment, a binding molecule or antigen binding molecule for use in the methods of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody.

In certain embodiments, modified antibodies for use in the methods disclosed herein are minibodies. Minibodies can be made using methods described in the art (see, e.g., see e.g., U.S. Pat. No. 5,837,821 or WO 94/09817A1).

In another embodiment, modified antibodies for use in the methods disclosed herein are $C_H2$ domain deleted antibodies which are known in the art. Domain deleted constructs can be derived using a vector (e.g., from Biogen IDEC Incorporated) encoding an IgG$_1$ human constant domain (see, e.g., WO 02/060955A2 and WO02/096948A2). This exemplary vector was engineered to delete the $C_H2$ domain and provide a synthetic vector expressing a domain deleted IgG$_1$ constant region.

In one embodiment, a Sp35 antagonist antibody or fragment thereof for use in the treatment methods disclosed herein comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides the use of antibodies that comprise, consist essentially of, or consist of, variants (including derivatives) of antibody molecules (e.g., the $V_H$ regions and/or $V_L$ regions) described herein, which antibodies or fragments thereof immunospecifically bind to a Sp35 polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known in the art.

Fusion Proteins and Conjugated Polypeptides and Antibodies

Sp35 polypeptides and antibodies for use in the treatment methods disclosed herein may further be recombinantly fused to a heterologous polypeptide at the N- or C-terminus or chemically conjugated (including covalent and non-covalent conjugations) to polypeptides or other compositions. For example, Sp35 antagonist polypeptides or antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Sp35 antagonist polypeptides and antibodies for use in the treatment methods disclosed herein include derivatives that are modified, i.e., by the covalent attachment of any type of molecule such that covalent attachment does not prevent the Sp35 antagonist polypeptide or antibody from inhibiting the biological function of Sp35. For example, but not by way of limitation, the Sp35 antagonist polypeptides and antibodies of the present invention may be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Sp35 antagonist polypeptides and antibodies for use in the treatment methods disclosed herein can be composed of amino acids joined to each other by peptide bonds or modified peptide bonds, i.e., peptide isosteres, and may contain amino acids other than the 20 gene-encoded amino acids. Sp35 antagonist polypeptides and antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the Sp35 antagonist polypeptide or antibody, including the peptide backbone, the amino acid side-chains and the amino or carboxyl termini, or on moieties such as carbohydrates. It will be appreciated that the same type of modification may be present in the same or varying degrees at several sites in a given Sp35 antagonist polypeptide or antibody. Also, a given Sp35 antagonist polypeptide or antibody may contain many types of modifications. Sp35 antagonist polypeptides or antibodies may be branched, for example, as a result of ubiquitination, and they may be cyclic, with or without branching. Cyclic, branched, and branched cyclic Sp35 antagonist polypeptides and antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W.H. Freeman and Company, New York 2nd Ed., (1993); *Posttranslational Covalent Modification Of Proteins*, B. C. Johnson, Ed., Academic Press, New York, pgs. 1-12 (1983); Seifter et al., Meth Enzymol 182:626-646 (1990); Rattan et al., *Ann NY Acad Sci* 663:48-62 (1992)).

The present invention also provides for fusion proteins comprising, consisting essentially of, or consisting of a Sp35 antagonist polypeptide or antibody fusion that inhibits Sp35 function. Preferably, the heterologous polypeptide to which the Sp35 antagonist polypeptide or antibody is fused is useful for function or is useful to target the Sp35 antagonist polypeptide or antibody. In certain embodiments of the invention a soluble Sp35 antagonist polypeptide, e.g., an Sp35 polypeptide comprising the LRR domains, Ig domain, or the entire extracellular domain (corresponding to amino acids 34 to 532 of SEQ ID NO: 2), is fused to a heterologous polypeptide moiety to form a Sp35 antagonist fusion polypeptide. Sp35 antagonist fusion proteins and antibodies can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active.

Also, it can be chosen to be stably fused to the Sp35 antagonist polypeptide or antibody or to be cleavable, in vitro or in vivo. Heterologous moieties to accomplish these other objectives are known in the art.

As an alternative to expression of an Sp35 antagonist fusion polypeptide or antibody, a chosen heterologous moiety can be preformed and chemically conjugated to the Sp35 antagonist polypeptide or antibody. In most cases, a chosen heterologous moiety will function similarly, whether fused or conjugated to the Sp35 antagonist polypeptide or antibody. Therefore, in the following discussion of heterologous amino acid sequences, unless otherwise noted, it is to be understood that the heterologous sequence can be joined to the Sp35 antagonist polypeptide or antibody in the form of a fusion protein or as a chemical conjugate.

Pharmacologically active polypeptides such as Sp35 antagonist polypeptides or antibodies often exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as Sp35 antagonist polypeptides or antibodies can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA* 89:1904-08 (1992) and Syed et al., *Blood* 89:3243-52 (1997), HSA can be used to form an Sp35 antagonist fusion polypeptide or antibody or polypeptide/antibody conjugate that displays pharmacological activity by virtue of the Sp35 moiety while displaying significantly increased in vivo stability, e.g., 10-fold to 100-fold higher. The C-terminus of the HSA can be fused to the N-terminus of the soluble Sp35 moiety. Since HSA is a naturally secreted protein, the HSA signal sequence can be exploited to obtain secretion of the soluble Sp35 fusion protein into the cell culture medium when the fusion protein is produced in a eukaryotic, e.g., mammalian, expression system.

The signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et al., *J. Immunol. Meth.* 125:191-202 (1989)), antibody heavy chain signal sequences, e.g., the MOPC141 antibody heavy chain signal sequence (Sakano et al., *Nature* 286:5774 (1980)). Alternatively, other signal sequences can be used. See, e.g., Watson, *Nucl. Acids Res.* 12:5145 (1984). The signal peptide is usually cleaved in the lumen of the endoplasmic reticulum by signal peptidases. This results in the secretion of an immunofusin protein containing the Fc region and the soluble Sp35 moiety.

In some embodiments, the DNA sequence may encode a proteolytic cleavage site between the secretion cassette and the soluble Sp35 moiety. Such a cleavage site may provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes a soluble Sp35 polypeptide and used for the expression and secretion of the soluble Sp35 polypeptide. Host cells that are typically used include immortal hybridoma cells, myeloma cells, 293 cells, Chinese hamster ovary (CHO) cells, Hela cells, and COS cells.

In one embodiment, a soluble Sp35 polypeptide is fused to a hinge and Fc region, i.e., the C-terminal portion of an Ig heavy chain constant region. Potential advantages of an Sp35-Fc fusion include solubility, in vivo stability, and multivalency, e.g., dimerization. The Fc region used can be an IgA, IgD, or IgG Fc region (hinge—$C_H2$—$C_H3$). Alternatively, it can be an IgE or IgM Fc region (hinge—$C_H2$—$C_H3$—$C_H4$). An IgG Fc region is generally used, e.g., an $IgG_1$ Fc region or $IgG_4$ Fc region. In one embodiment, a sequence beginning in the hinge region just upstream of the papain cleavage site which defines IgG Fc chemically (i.e. residue 216, taking the first residue of heavy chain constant region to be 114 according to the Kabat system), or analogous sites of other immunoglobulins is used in the fusion. The precise site at which the fusion is made is not critical; particular sites are well known and may be selected in order to optimize the biological activity, secretion, or binding characteristics of the molecule. Materials and methods for constructing and expressing DNA encoding Fc fusions are known in the art and can be applied to obtain soluble Sp35 fusions without undue experimentation. Some embodiments of the invention employ an Sp35 fusion protein such as those described in Capon et al., U.S. Pat. Nos. 5,428,130 and 5,565,335.

Fully intact, wild-type Fc regions display effector functions that normally are unnecessary and undesired in an Fc fusion protein used in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the $C_H2$ domain of the Fc region of IgE, such that this site does not interfere with the efficient secretion of the immunofusin. Transmembrane domain sequences, such as those present in IgM, also are generally deleted.

The $IgG_1$ Fc region is most often used. Alternatively, the Fc region of the other subclasses of immunoglobulin gamma (gamma-2, gamma-3 and gamma-4) can be used in the secretion cassette. The $IgG_1$ Fc region of immunoglobulin gamma-1 is generally used in the secretion cassette and includes at least part of the hinge region, the $C_H2$ region, and the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., *Hum. Antibod. Hybridomas* 1:47 (1990). In some embodiments, the Fc region of one of IgA, IgD, IgE, or IgM, is used.

Sp35-Fc fusion proteins can be constructed in several different configurations. In one configuration the C-terminus of the soluble Sp35 moiety is fused directly to the N-terminus of the Fc hinge moiety. In a slightly different configuration, a short polypeptide, e.g., 2-10 amino acids, is incorporated into the fusion between the N-terminus of the soluble Sp35 moiety and the C-terminus of the Fc moiety. Such a linker provides conformational flexibility, which may improve biological activity in some circumstances. If a sufficient portion of the hinge region is retained in the Fc moiety, the Sp35-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino-reactive group and thiol-reactive group can be used to link Sp35 antagonist polypeptides to serum albumin. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, SIAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of a soluble Sp35 polypeptide or the thiol moiety on serum albumin. For example, soluble Sp35-albumin fusions can be obtained using genetic engineering techniques, wherein the soluble Sp35 moiety is fused to the serum albumin gene at its N-terminus, C-terminus, or both.

Soluble Sp35 polypeptides can be fused to heterologous peptides to facilitate purification or identification of the soluble Sp35 moiety. For example, a histidine tag can be fused to a soluble Sp35 polypeptide to facilitate purification using commercially available chromatography media.

In some embodiments of the invention, a soluble Sp35 fusion construct is used to enhance the production of a soluble Sp35 moiety in bacteria. In such constructs a bacterial protein normally expressed and/or secreted at a high level is employed as the N-terminal fusion partner of a soluble Sp35 polypeptide. See, e.g., Smith et al., *Gene* 67:31 (1988); Hopp et al., *Biotechnology* 6:1204 (1988); La Vallie et al., *Biotechnology* 11:187 (1993).

By fusing a soluble Sp35 moiety at the amino and carboxy termini of a suitable fusion partner, bivalent or tetravalent forms of a soluble Sp35 polypeptide can be obtained. For example, a soluble Sp35 moiety can be fused to the amino and carboxy termini of an Ig moiety to produce a bivalent monomeric polypeptide containing two soluble Sp35 moieties. Upon dimerization of two of these monomers, by virtue of the Ig moiety, a tetravalent form of a soluble Sp35 protein is obtained. Such multivalent forms can be used to achieve increased binding affinity for the target. Multivalent forms of soluble Sp35 also can be obtained by placing soluble Sp35 moieties in tandem to form concatamers, which can be employed alone or fused to a fusion partner such as Ig or HSA.

Conjugated Polymers (Other than Polypeptides)

Some embodiments of the invention involve a soluble Sp35 polypeptide or Sp35 antibody wherein one or more polymers are conjugated (covalently linked) to the Sp35 polypeptide or antibody. Examples of polymers suitable for such conjugation include polypeptides (discussed above), sugar polymers and polyalkylene glycol chains. Typically, but not necessarily, a polymer is conjugated to the soluble Sp35 polypeptide or Sp35 antibody for the purpose of improving one or more of the following: solubility, stability, or bioavailability.

The class of polymer generally used for conjugation to a Sp35 antagonist polypeptide or antibody is a polyalkylene glycol. Polyethylene glycol (PEG) is most frequently used. PEG moieties, e.g., 1, 2, 3, 4 or 5 PEG polymers, can be conjugated to each Sp35 antagonist polypeptide or antibody to increase serum half life, as compared to the Sp35 antagonist polypeptide or antibody alone. PEG moieties are non-antigenic and essentially biologically inert. PEG moieties used in the practice of the invention may be branched or unbranched.

The number of PEG moieties attached to the Sp35 antagonist polypeptide or antibody and the molecular weight of the individual PEG chains can vary. In general, the higher the molecular weight of the polymer, the fewer polymer chains attached to the polypeptide. Usually, the total polymer mass attached to the Sp35 antagonist polypeptide or antibody is from 20 kDa to 40 kDa. Thus, if one polymer chain is attached, the molecular weight of the chain is generally 20-40 kDa. If two chains are attached, the molecular weight of each chain is generally $10^{-20}$ kDa. If three chains are attached, the molecular weight is generally 7-14 kDa.

The polymer, e.g., PEG, can be linked to the Sp35 antagonist polypeptide or antibody through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the Sp35 antagonist polypeptide or antibody. Free carboxylic groups, suitably activated carbonyl groups, hydroxyl, guanidyl, imidazole, oxidized carbohydrate moieties and mercapto groups of the Sp35 antagonist polypeptide or antibody (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the Sp35 antagonist polypeptide or antibody. Preferably, at least 50% of the biological activity (as demonstrated, e.g., in any of the assays described herein or known in the art) of the Sp35 antagonist polypeptide or antibody is retained, and most preferably nearly 100% is retained.

The polymer can be conjugated to the Sp35 antagonist polypeptide or antibody using conventional chemistry. For example, a polyalkylene glycol moiety can be coupled to a lysine epsilon amino group of the Sp35 antagonist polypeptide or antibody. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors* 3:4-10 (1992), and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5:133-140, 1994. Reaction parameters are generally selected to avoid temperature, solvent, and pH conditions that would damage or inactivate the soluble Sp35 polypeptide.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with Sp35 antagonist polypeptide or antibody in the presence of a reducing agent. In addition, one can manipulate the reaction conditions to favor PEGylation substantially only at the N-terminal amino group of Sp35 antagonist polypeptide or antibody, i.e. a mono-PEGylated protein. In either case of mono-PEGylation or poly-PEGylation, the PEG groups are typically attached to the protein via a —$C_H2$—NH— group. With particular reference to the—$C_H2$— group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated soluble Sp35 polypeptide or antibody generally includes the steps of (a) reacting a Sp35 antagonist polypeptide or antibody with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/soluble Sp35 polypeptide or Sp35 antibody generally includes the steps of: (a) reacting a soluble Sp35 protein or polypeptide with a reactive PEG molecule under reductive alkylation conditions, at a pH suitable to pen-nit selective modification of the N-terminal amino group of the polypeptide or antibody; and (b) obtaining the reaction product(s).

For a substantially homogeneous population of mono-polymer/soluble Sp35 polypeptide or Sp35 antibody, the reductive alkylation reaction conditions are those that permit the selective attachment of the water-soluble polymer moiety to the N-terminus of the polypeptide or antibody. Such reaction conditions generally provide for pKa differences between the lysine side chain amino groups and the N-terminal amino group. For purposes of the present invention, the pH is generally in the range of 3-9, typically 3-6.

Soluble Sp35 polypeptides or antibodies can include a tag, e.g., a moiety that can be subsequently released by proteolysis. Thus, the lysine moiety can be selectively modified by first reacting a His-tag modified with a low-molecular-weight linker such as Traut's reagent (Pierce) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly one could react the protein with an amine-reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the Sp35 antagonist polypeptide or antibody. Coupling can be effected using, e.g., a maleimide group, a vinylsulfone group, a haloacetate group, or a thiol group.

Optionally, the soluble Sp35 polypeptide or antibody is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

Sp35 Polynucleotide Antagonists

Specific embodiments comprise a method of treating a demyelination or dysmyelination disorder, comprising administering an effective amount of an Sp35 polynucleotide antagonist which comprises a nucleic acid molecule which specifically binds to a polynucleotide which encodes Sp35. The Sp35 polynucleotide antagonist prevents expression of Sp35 (knockdown). Sp35 polynucleotide antagonists include, but are not limited to antisense molecules, ribozymes, siRNA, shRNA and RNAi. Typically, such binding molecules are separately administered to the animal (see, for example, O'Connor, J. Neurochem. 56:560 (1991), but such binding molecules may also be expressed in vivo from polynucleotides taken up by a host cell and expressed in vivo. See also Oligodeoxynucleotides as Antisense Inhibitors of Gene Expression, CRC Press, Boca Raton, Fla. (1988).

RNAi refers to the expression of an RNA which interferes with the expression of the targeted mRNA. Specifically, the RNAi silences a targeted gene via interacting with the specific mRNA (e.g. Sp35) through a siRNA (short interfering RNA). The ds RNA complex is then targeted for degradation by the cell. Additional RNAi molecules include Short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi.

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in *Drosophila* cell-free lysates indicates that the mediators of RNA-dependent gene silencing are 21-25 nucleotide "small interfering" RNA duplexes (siRNAs). Accordingly, siRNA molecules are advantageously used in the methods of the present invention. The siRNAs are derived from the processing of dsRNA by an RNase known as DICER (Bernstein et al., *Nature* 409:363-366, 2001). It appears that siRNA duplex products are recruited into a multi-protein siRNA complex termed RISC (RNA Induced Silencing Complex). Without wishing to be bound by any particular theory, it is believed that a RISC is guided to a target mRNA, where the siRNA duplex interacts sequence-specifically to mediate cleavage in a catalytic fashion (Bernstein et al., *Nature* 409:363-366, 2001; Boutla et al., *Curr Biol* 11:1776-1780, 2001).

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., *Nature* 418:379-380, 2002) and HIV (Capodici et al., *J Immunol* 169:5196-5201, 2002), and reducing expression of oncogenes (e.g., the bcr-abl gene; Scherr et al., *Blood* September 26 epub ahead of print, 2002). RNAi has been used to modulate gene expression in mammalian (mouse) and amphibian (*Xenopus*) embryos (respectively, Calegari et al., *Proc Natl Acad Sci USA* 99:14236-14240, 2002; and Zhou, et al., *Nucleic Acids Res* 30:1664-1669, 2002), and in postnatal mice (Lewis et al., *Nat Genet* 32:107-108, 2002), and to reduce trangsene expression in adult transgenic mice (McCaffrey et al., *Nature* 418:38-39, 2002). Methods have been described for determining the efficacy and specificity of siRNAs in cell culture and in vivo (see, e.g., Bertrand et al., *Biochem Biophys Res Commun* 296:1000-1004, 2002; Lassus et al., *Sci STKE* 2002 (147):PL13, 2002; and Leirdal et al., *Biochem Biophys Res Commun* 295:744-748, 2002).

Molecules that mediate RNAI, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules may also be formed by annealing two oligonucleotides to each other, typically have the following general structure, which includes both double-stranded and single-stranded portions:

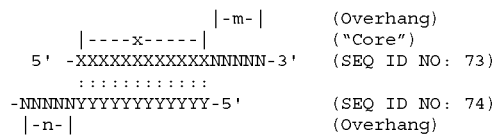

```
                    |-m-|        (Overhang)
          |----x----|             ("Core")
     5'-XXXXXXXXXXXNNNNN-3'       (SEQ ID NO: 73)
        ::::::::::::
     3'-NNNNNYYYYYYYYYYY-5'       (SEQ ID NO: 74)
        |-n-|                     (Overhang)
```

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also within the scope of the invention. Also within the scope of the invention are siRNA molecules with no overhangs (i.e., m=0 and n=0), and those having an overhang on one side of the core but not the other (e.g., m=0 and n≧1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al, *Proc. Natl. Acad. Sci. USA* 94:3279-3283, 1997). In addition, it has long been known that dsRNA activates the interferon cascade in mammalian cells, which can also lead to altered cell physiology (Colby et al, *Annu. Rev. Microbiol* 25:333, 1971; Kleinschmidt et al., *Annu. Rev. Biochem.* 41:517, 1972; Lampson et al., *Proc. Natl. Acad. Sci. USA* 58L782, 1967; Lomniczi et al., *J. Gen. Virol.* 8:55, 1970; and Younger et al., *J. Bacteriol.* 92:862, 1966). However, dsRNA-mediated activation of the PKR and interferon cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409: 363-366, 2001; Boutla et al., *Curr Biol* 11:1776-1780, 2001; Cullen, *Nat Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-

3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously used in the methods of the invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

In some embodiments of the invention, the shRNA is expressed from a lentiviral vector (pLL3.7) as described in Example 1.

Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes Sp35 may be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for the Sp35 gene are produced intracellularly by transcription from an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule, can be by any promoter known in the art to act in vertebrate, preferably human cells, such as those described elsewhere herein.

Absolute complementarity of an antisense molecule, although preferred, is not required. A sequence complementary to at least a portion of an RNA encoding Sp35, means a sequence having sufficient complementarity to be able to hybridize with the RNA, forming a stable duplex; or triplex formation may be assayed. The ability to hybridize will depend on both the degree of complementarity and the length of the antisense nucleic acid. Generally, the larger the hybridizing nucleic acid, the more base mismatches it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333-335 (1994). Thus, oligonucleotides complementary to either the 5'- or 3'-non-translated, non-coding regions could be used in an antisense approach to inhibit translation of Sp35. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Polynucleotides for use the therapeutic methods disclosed herein can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958-976 (1988)) or intercalating agents. (See, e.g., Zon, *Pharm. Res.* 5:539-549(1988)). To this end, the oligonucleotide may be conjugated to another molecule, e.g., a peptide, hybridization triggered cross-linking agent, transport agent, hybridization-triggered cleavage agent, etc.

An antisense oligonucleotide for use in the therapeutic methods disclosed herein may comprise at least one modified base moiety which is selected from the group including, but not limited to, 5fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N-2-carboxypropyl) uracil, (acp3)w, and 2,6-diaminopurine.

An antisense oligonucleotide for use in the therapeutic methods disclosed herein may also comprise at least one modified sugar moiety selected from the group including, but not limited to, arabinose, 2-fluoroarabinose, xylulose, and hexose.

In yet another embodiment, an antisense oligonucleotide for use in the therapeutic methods disclosed herein comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, an antisense oligonucleotide for use in the therapeutic methods disclosed herein is an α-anomeric oligonucleotide. An α-anomeric oligonucleotide forms specific double-stranded hybrids with complementary RNA in which, contrary to the usual situation, the strands run parallel to each other (Gautier et al., *Nucl. Acids Res.* 15:6625-6641(1987)). The oligonucleotide is a 2'-O-methyl-ribonucleotide (Inoue et al., *Nucl. Acids Res.* 15:6131-6148 (1987)), or a chimeric RNA-DNA analogue (Inoue et al., *FEBS Lett.* 215:327-330(1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. U.S.A.* 85:7448-7451(1988)), etc.

Polynucleotide compositions for use in the therapeutic methods disclosed herein further include catalytic RNA, or a ribozyme (See, e.g., PCT International Publication WO 90/11364, published Oct. 4, 1990; Sarver et al., *Science* 247: 1222-1225 (1990). The use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). Preferably, the ribozyme is engineered so that the cleavage recognition site is located near the 5' end of the target mRNA; i.e., to increase efficiency and minimize the intracellular accumulation of non-functional mRNA transcripts.

As in the antisense approach, ribozymes for use in the diagnostic and therapeutic methods disclosed herein can be composed of modified oligonucleotides (e.g. for improved stability, targeting, etc.) and may be delivered to cells which express Sp35 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous Sp35 messages and inhibit translation. Since ribozymes unlike antisense molecules, are catalytic, a lower intracellular concentration is required for efficiency.

Vectors

Vectors comprising nucleic acids encoding Sp35 antagonists may also be used to produce antagonists for use in the methods of the invention. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements may also be needed for optimal synthesis of mRNA. These elements may include signal sequences, splice signals, as well as transcriptional promoters, enhancers, and termination signals.

In one embodiment, a proprietary expression vector of Biogen IDEC, Inc., referred to as NEOSPLA (U.S. Pat. No. 6,159,730) may be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pm12d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of the antagonist is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMlP)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors encoding Sp35 antagonists can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110$^{-14}$ (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Host Cells

Host cells for expression of an Sp35 antagonist for use in a method of the invention may be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

Gene Therapy

An Sp35 antagonist can be produced in vivo in a mammal, e.g., a human patient, using a gene-therapy approach to treatment of a nervous-system disease, disorder or injury in which promoting survival, proliferation and differentiation of oligodendrocytes or promoting myelination of neurons would be therapeutically beneficial. This involves administration of a suitable Sp35 antagonist-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, adeno-associated viral vector and a herpes simplex viral vector. The viral vector can be a replication-defective viral vector. Adenoviral vectors that have a deletion in its E1 gene or E3 gene are typically used. When an adenoviral vector is used, the vector usually does not have a selectable marker gene.

Pharmaceutical Compositions

The Sp35 antagonists used in the methods of the invention may be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, Sp35 antagonists used in the methods of the invention act in the nervous system to promote survival, proliferation and differentiation of oligodendrocytes and myelination of neurons. Accordingly, in the methods of the invention, the Sp35 antagonists are administered in such a way that they cross the blood-brain barrier. This crossing can result from the physico-chemical properties inherent in the Sp35 antagonist molecule itself, from other components in a pharmaceutical formulation, or from the use of a mechanical device such as a needle, cannula or surgical instruments to breach the blood-brain barrier. Where the Sp35 antagonist is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the Sp35 antagonist is a molecule that inherently crosses the blood-brain barrier, the route of administration may be by one or more of the various routes described below.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an Sp35 antagonist that may be combined with the carrier materials to produce a single dosage form will vary depending upon the host treated, the type of antagonist used and the particular mode of administration. The composition may be administered as a single dose, multiple doses or over an established period of time in an infusion. Dosage regimens also may be adjusted to provide the optimum desired response (e.g., a therapeutic or prophylactic response).

The methods of the invention use a "therapeutically effective amount" or a "prophylactically effective amount" of an Sp35 antagonist. Such a therapeutically or prophylactically effective amount may vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular Sp35 antagonist used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods of the invention the Sp35 antagonists are generally administered directly to the nervous system, intracerebroventricularly, or intrathecally, e.g. into a chronic lesion of MS. Compositions for administration according to the methods of the invention can be formulated so that a dosage of 0.001-10 mg/kg body weight per day of the Sp35 antagonist polypeptide is administered. In some embodiments of the invention, the dosage is 0.01-1.0 mg/kg body weight per day. In some embodiments, the dosage is 0.001-0.5 mg/kg body weight per day.

For treatment with an Sp35 antagonist antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

In certain embodiments, a subject can be treated with a nucleic acid molecule encoding a Sp35 antagonist polynucleotide. Doses for nucleic acids range from about 10 ng to 1 g, 100 ng to 100 mg, 1 μg to 10 mg, or 30-300 μg DNA per patient. Doses for infectious viral vectors vary from 10-100, or more, virions per dose.

Supplementary active compounds also can be incorporated into the compositions used in the methods of the invention. For example, a soluble Sp35 polypeptide or a fusion protein may be coformulated with and/or coadministered with one or more additional therapeutic agents.

The invention encompasses any suitable delivery method for an Sp35 antagonist to a selected target tissue, including bolus injection of an aqueous solution or implantation of a controlled-release system. Use of a controlled-release implant reduces the need for repeat injections.

The Sp35 antagonists used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent 125I Implants for Recurrent Malignant Gliomas," *Int. J. Radiation Oncology Biol. Phys.* 43(5): 977-982 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise an Sp35 antagonist dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments of the invention, an Sp35 antagonist is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer an Sp35 antagonist according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of demyelination or dysmyelination disorders as described herein are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the differentiation and survival effect of the Sp35 antagonists are described herein. The effect of the Sp35 antagonists on myelination of axons can be tested in vitro as described in the Examples. Finally, in vivo tests can be performed by creating transgenic mice which express the Sp35 antagonist or by administering the Sp35 antagonist to mice or rats in models as described herein.

EXAMPLES

Example 1

Sp35 is Involved in Oligodendrocyte Biology

Oligodendrocytes mature through several developmental stages from A2B5 progenitor cells (which express A2B5), differentiating into pre-myelinating oligodendrocytes (which express O1 and O4) and finally into mature myelinating oligodendrocytes (which express O1, O4 and MBP). Thus, by monitoring the presence and absence of the A2B5, O1, O4 and MBP markers it is possible to determine a given cell's developmental stage and to evaluate the role of Sp35-Fc in oligodendrocyte biology. For a general review of oligodendrocyte biology, see, e.g., Baumann and Pham-Dinh, *Physiol. Rev.* 81: 871-927 (2001).

Monoclonal antibodies against O4, MBP and CNPase were from Stemberger Monoclonals; antibody to APC (clone CC-1; ref. 29) was from Calbiochem. Other antibodies were to βIII tubulin (Covance), Sp35 (Biogen Idec), Fyn (Santa Cruz Biotechnology) and phospho-Fyn (Biosource). Monoclonal antibodies against A2B5 are available from Chemicon.

Sp35 is Expressed in Oligodendrocytes

The expression of Sp35 in purified rat P13 CG neuron, P2 oligodendrocyte, and P4 astrocyte cultures was analyzed by polymerase chain reaction after reverse transcription (RT-PCR). A kit from Ambion, Inc. was used to extract mRNA from the rat brain cells according to the manufacturer's instructions. Semi-quantitative RT-PCR was carried out using forward primer 5' AGAGACATGCGATTGGTGA 3' (SEQ ID NO:38), and reverse primer 5' AGAGATGTAGACGAGGTCATT 3' (SEQ ID NO:39) showed high expression in neurons, lower expression in oligodendrocytes, and no expression in astrocytes. (FIG. 5).

The expression of Sp35 in oligodendrocytes was confirmed by in situ hybridization in sections derived from adult rat optic nerve. Rat optic nerve sections were prepared and processed as described in Mi et al., "Sp35 is a component of the Nogo-66 receptor/p75 signaling complex," *Nat. Neurosci.* 7: 221-28 (2004) and probed with digoxigenin-labeled Sp35 antisense or sense RNAs using the first 500 nucleotides of the Sp35 coding sequence. The sections were stained according to the manufacturers' instructions using a Tyramide Signal Amplification kit (Amersham Biosciences) and a fluorescent anti-digoxigenin conjugated antibody kit (Perkin Elmer). For combined in situ and immunofluorescence analyses, the sections were first probed with digoxigenin-labeled RNAs and then with antibodies, e.g. CC1 antibody (Calbiochem; a marker of mature oligodendrocytes) or anti-Sp35 antibody. We observed that oligodendrocytes that hybridized to an antisense Sp35 probe also co-stained with an antibody to CC1

(data not shown). No specific labeling was observed using a sense Sp35 probe. Sp35 expression in oligodendrocytes also was confirmed by immunohistochemistry studies of tissue sections from the lateral ventricle region of P7 rat cortex. A majority of cortical cells that labeled with CC1 antibody also labeled with anti-Sp35 antibody. Data not shown. The specificity of the interaction was confirmed by preadsorption of the anti-Sp35 antibody with Sp35-Fc (see Example 2), which eliminated the signal.

Sp35-Specific RNAi Knockdown of Sp35 Expression Promotes Oligodendrocyte Growth and Differentiation Sp35-specific RNAi was used to ablate Sp35 expression in oligodendrocyte precursor cells to examine how Sp35 contributes to oligodendrocyte growth and differentiation. 50,000 A2B5 oligodendrocyte precursor cells were infected with lentivirus carrying Sp35-specific RNAi sequence or control RNAi prepared as follows.

Murine and rat Sp35 DNA sequences were compared to find homologous regions to use for candidate small-hairpin RNAs (shRNA). CH324, for lentivirus expression of Sp35 RNAi, was constructed by annealing oligonucleotides LV1-035 and LV1-036 and ligating to HpaI and XhoI digested pLL3.7. The pLL3.7 vector, additional methodology and virus production were as described in Rubinson et al., *Nat. Genet.* 33, 401-06 (2003). The Sp35 RNAi oligonucleotides were purchased from MWG and have the following sequences:

```
LV1-035 (sense oligo)
                                    (SEQ ID NO: 40)
5'-TGATCGTCATCCTGCTAGACTTCAAGAGAGTCTAGCAGGATGACGA
TCTTTTTTC-3'
and LV1-036 (antisense oligo)
                                    (SEQ ID NO: 41)
5'-TCGAGAAAAAAGATCGTCATCCTGCTAGACTCTCTTGAAGTCTAGC
AGGATGACGATCA-3'.
```

Control RNAi was designed with the same oligonucleotide sequences except for the nucleotide changes indicated in lower-case letters: 5'-TGATCcTCATcCttCTAtACTTCAA-GAGAGTgTAGCAGGATGAcGATCT TTTTTCTCGA-3' (SEQ ID NO:42) and 5'-TCGAGAAAAAAGATCGTCATC-CTGCTAGACTCTCTTGAAGTaTAGaA GGATGAC-GATCA-3'. (SEQ ID NO:43).

Prior to producing the lentivirus, DNA from pLL3.7 or candidate shRNA in pLL3.7 were cotransfected with murine Sp35-HA tagged plasmid at a ratio of 5 to 1 into CHO cells in 6-well format. Knockdown was analyzed by western blot detection of Sp35-HA tag from transfected CHO cell lysates as well as by northern blot of total RNA prepared from duplicate wells. The blot was probed with a fragment of Sp35 cDNA. Assays were performed 48 hours post-transfection. As expected, there was a 10-fold reduction of Sp35 mRNA in $C_H324$ RNAi-treated CHO cells relative to control-treated cells. Data not shown. RNAi lentiviruses carrying green fluorescent protein (GFP) were generated as described in Rubinson et al. In cultures treated with either control or Sp35 RNAi, approximately 80% of the oligodendrocytes were GFP positive. Total cell number was not altered by the RNAi treatments. To quantify the effects of RNAi on differentiation, only GFP-expressing oligodendrocytes were counted.

Enriched populations of oligodendrocytes were grown from female Long Evans P2 rats as described by Conn, *Meth. Neurosci.* 2:1-4 (Academic Press; 1990) with modifications as follows. Briefly, the forebrain was dissected and placed in Hank's buffered salt solution (HBSS; Invitrogen). The tissue was cut into 1-mm fragments and was incubated at 37° C. for 15 min in 0.01% trypsin and 10 µg/ml DNase. Dissociated cells were plated on poly-L-lysine-coated T75 tissue culture flasks and were grown at 37° C. for 10 d in DMEM medium with 20% fetal calf serum (Invitrogen). Oligodendrocyte precursors (A2B5+) were collected by shaking the flask overnight at 200 rpm at 37° C., resulting in a 95% pure population. Cultures were maintained in high-glucose Dulbecco's modified Eagle's medium (DMEM) with FGF/PDGF (10 ng/ml; Peprotech) for 1 week. Removal of FGF/PDGF allowed A2B5+ cells to differentiate into O4+ premyelinating oligodendrocytes after 3-7 d, and to differentiate into O4+ and MBP+ mature oligodendrocytes after 7-10 d. These differentiation states are readily apparent from changes in morphology: A2B5+ cells are bipolar in shape, O4+ premyelinating oligodendrocytes have longer and more branched processes and MBP+ mature oligodendrocytes contain myelin sheet structures between processes.

Figure 6:
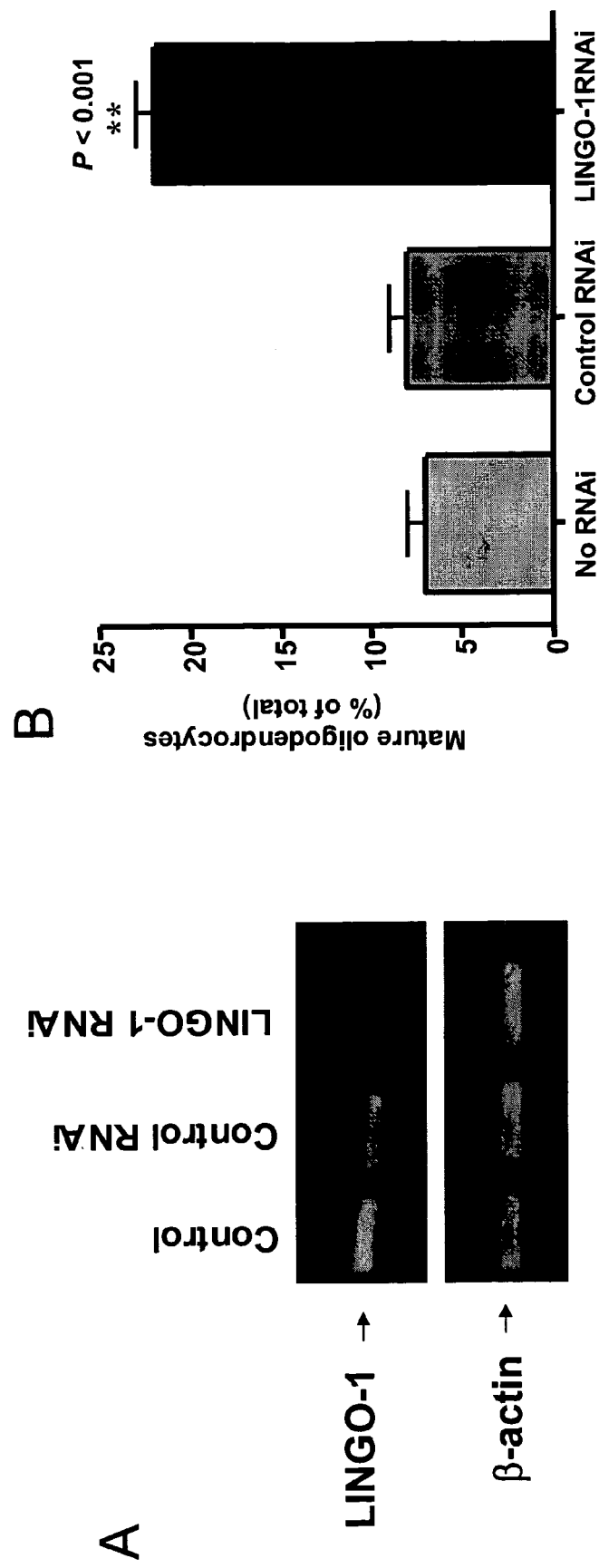
FIGS. 6A and 6B—(A) RT-PCR analysis of Sp35 (LINGO-1) mRNA expression from RNAi-infected oligodendrocytes and an uninfected control. β-actin was used as an internal standard. (B) Quantification of mature oligodendrocytes in RNAi-treated cultures.

A2B5 oligodendrocyte precursor cells were infected with the lentivirus containing the $C_H324$ RNAi. The resulting cells were cultured for 3 days and the number of O4-positive (a marker for oligodendrocyte differentiation) oligodendrocytes was counted. Endogenous Sp35 expression was reduced by infection with Sp35 RNAi lentivirus and was confirmed by RT-PCR (FIG. 6A). Reduction of Sp35 resulted in more highly differentiated, mature oligodendrocytes as compared with control infected cells, as was evident by increases in the length of cell processes and by the presence of abundant myelin sheet structures (data not shown). In cells that expressed Sp35 RNAi, there were three times as many mature (O4-positive) oligodendrocytes as in control cultures (FIG. 6B). These data indicate that Sp35 may negatively regulate oligodendrocyte differentiation.

Dominant-Negative Sp35 Promotes Oligodendrocyte Growth and Differentiation

We constructed lentiviral vectors that express wild-type and a dominant-negative form of Sp35. DNA sequence encoding mouse full length Sp35 (FL-Sp35, amino acid residues 34-614 of SEQ ID NO:2) was amplified by PCR using primers 5'-GAGGATCTCGACGCGGCCGCATGGAGA-CAGACACACTCCTG-3' (SEQ ID NO:44) and 5'-GGGGCGGAATTGGATCCTCACAGATC-CTCTTCTGAGATGAG-3' (SEQ ID NO:45) and inserted into the HRST-IRESeGFP lentiviral vector at the NotI and BamHI sites. Similarly, DNA sequence encoding dominant negative Sp35 (DN-Sp35, amino acid residues 34-581 of SEQ ID NO:2) was amplified by PCT using primers 5'-GAG-GATCTCGACGCGGCCGCATGGAGACAGA-CACACTCCTG-3' (SEQ ID NO:46) and 5'-GATACG-GATCCTCAGCCTTTGCCCCGGCTCCATAGAAACAGC-3' (SEQ ID NO:47). The FL-Sp35 and DN-Sp35 plasmids were transfected into 293 cells to produce lentivirus as described by Rubinson et al., "A lentivirus-based system to functionally silence genes in primary mammalian cells, stem cells and transgenic mice by RNA interference," *Nat. Genet.* 33: 401-06 (2003). Oligodendrocytes (prepared as described in Example 4) were infected with lentivirus at 2 MOI per cell and confirmed expression of FL-Sp35 and DN-Sp35 by western blot.

DN-Sp35 promoted oligodendrocyte differentiation, producing an increase in the number of mature oligodendrocytes. In contrast, overexpression of full-length Sp35 (FL-Sp35) had the opposite effect and inhibited differentiation, as was evident by a reduction in the number of mature oligodendrocytes as compared with the control (data not shown.

Example 2

Construction and Purification of Sp35-Fc Fusion Protein

A construct was made fusing the extra-cellular portion of human Sp35 (residues 1-532) to the hinge and Fc region of human IgG1 to study the biological function of Sp35. A partial coding sequence for human Sp35 was obtained by PCR from clone 227.2 using the forward primer 5'-CAG-CAGGTCGACGCGGCCGCATGCTGGCG GGGGGCGT-3' (SEQ ID NO:48) and reverse primer 5' CAGCAGGTC-GACCTCGCCCGGCTGGTTGGCCAACCAGCCGGGCGA GGTCGACCTCGAGG-3' (SEQ ID NO:49).

The blunt-end PCR product was subcloned into the SrfI site of the PCR SCRIPT AMP vector (Stratagene) to create PCR SCRIPT AMP-Sp35. A SalI fragment was isolated from PCR SCRIPT AMP-Sp35 and subcloned into the PCRCAMP Ig vector (derivative of Stratagene vector PCR SCRIPT AMP). In the PCRCAMP Ig vector, the hinge and Fc gamma sequence is subcloned as a SalI(5') to NotI(3') fragment. The SalI Sp35 fragment was subcloned into the SalI site of the PCRCAMP Ig vector thereby fusing the Sp35 signal sequence and extracellular domain (codons 1-532) in-frame with sequences encoding the hinge and Fc region of human Ig1. Correct isolates were identified, and a NotI fragment encompassing the Sp35 Fc fragment was subcloned into the single NotI cloning site of the CHO expression vector, PV90 (Biogen Idec). The resulting plasmid was confirmed by DNA sequencing aand designated GT123.

Stable cell lines expressing the Sp35-Fc fusion protein were generated by electroporation of CHO host cells DG44 with plasmid GT123. Transfected CHO cells were cultured in alpha minus MEM in the presence of 10% dialyzed serum and 4 mM glutamine to select for nucleoside-independent growth. Fourteen days post-transfection, cells were fed fresh media. To screen for cells expressing Sp35-Fc, CHO cells were labeled with phycoerythrin (PE)-labeled goat anti-human IgG (Jackson Labs) and subjected to high speed flow cytometry sorting in a FACS Mo-Flo (Cytomation). The cells that expressed the highest levels of Sp35-Fc were selected. These cells were expanded in culture for 7 days, then re-labeled and re-sorted. Cells expressing the highest levels of Sp35-Fc were isolated as individual clones in 96-well plates. These clones were grown for two weeks and then fed fresh media one day prior to FACS analysis to check for expression levels. Clones that expressed the highest levels of Sp35-Fc were expanded, and frozen cell banks were established. The cell lines were adapted to grow in suspension culture in the serum-free media BCM16. The titer of Sp35-Fc produced by these clones was determined by growing cell lines at 37° C. for 4-5 passages, then growing the cells to 50% maximal cell density and culturing them for 10-15 days at 28° C. until the viable cell density dropped to 75%. At this time, the culture media were harvested, cleared of cells and debris by centrifugation, and the culture supernatants titered for Sp35-Fc levels by Western blot analysis using an anti-human Ig antibody (Jackson Lab) as the probe.

Sp35-Fc fusion protein was purified from the clarified culture medium as follows: 9 ml of 1M HEPES pH 7.5 was added to 900 ml of conditioned medium. The medium was batch loaded for 3 hr at 4° C. onto 3 ml of Protein A Sepharose (Amersham Bioscience). The resin was collected in a 1.5 cm (I.D.) column, and washed four times with 3 ml PBS, two times with 4 ml of PBS containing 800 mM NaCl, and then again with 3 ml of PBS. The Sp35-Fc was eluted from the column with 25 mM $NaH_2PO_4$, pH 2.8 and 100 mM NaCl in 1.5 ml fractions and neutralized by adding 75 µl of 0.5 M $NaH_2PO_4$, pH 8.6. Peak protein-containing fractions were identified by absorbance at 280 nm, pooled, and subjected to further purification on a 1 mL Protein A column. Prior to loading, NaCl was added to 600 mM and HEPES, pH 7.5 to 50 mM. The column was washed twice with 600 µl of 10 mM HEPES pH 7.5 and 1 M NaCl, and then with 1 ml PBS. Sp35-Fc was eluted from the column with 25 mM $NaH_2PO_4$, pH 2.8 and 100 mM NaCl, collecting 0.5 mL fractions, and neutralized by adding 25 µl of 0.5 M $NaH_2PO_4$, pH 8.6. Peak protein-containing fractions were identified by absorbance at 280 nm and pooled. By reducing SDS-PAGE, the Sp35-Fc protein migrated as a single band (>95% pure) with an apparent mass of 90 kDa. Under non-reducing conditions, the protein ran as a dimer with an approximate mass of 180 kDa. The purified Sp35-Fc protein was aliquoted and stored at −70° C.

Example 3

Figure 7:
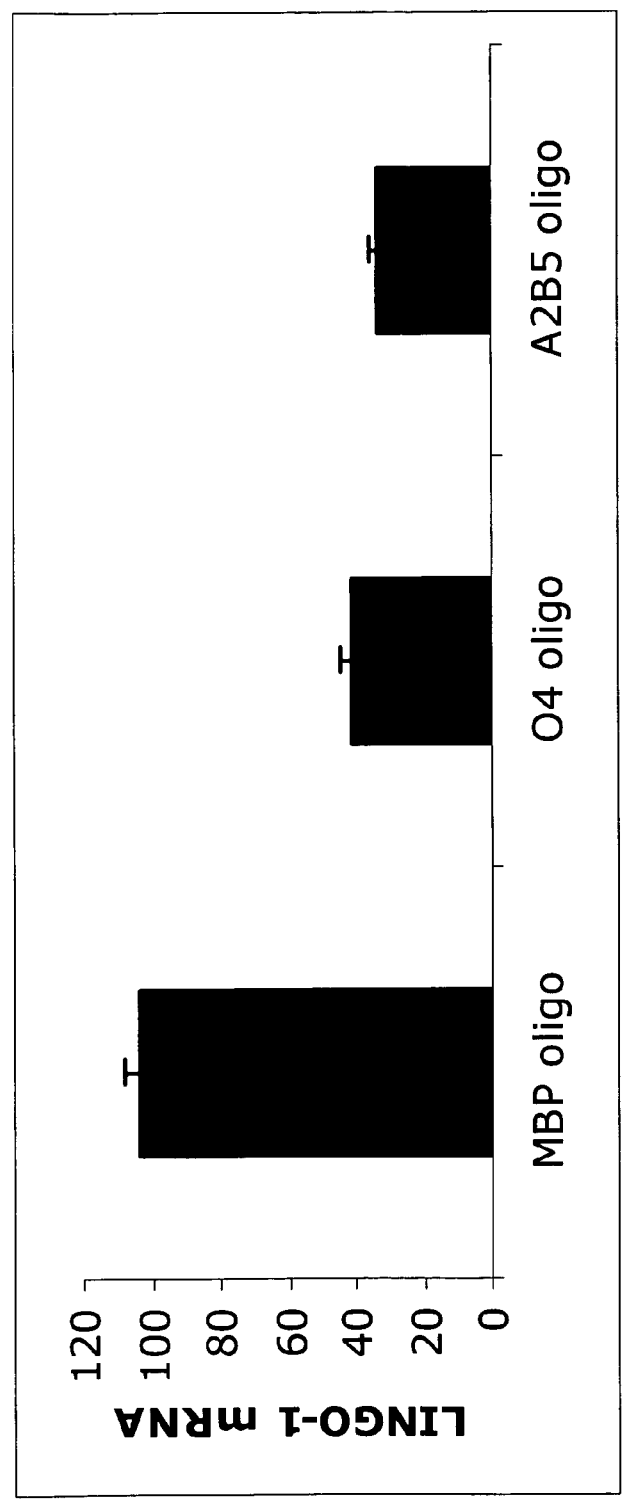
FIG. 7—Sp35 (LINGO-1) mRNA expression in oligodendrocytes at various developmental stages. Oligodendrocytes were induced to differentiate and quantitation of Sp35 was carried out by RT-PCR. Data were normalized to GAPDH levels as an internal control. Early progenitor oligodendrocytes (A2B5$^+$) and pre-myelinating oligodendrocytes (O4$^+$) showed equivalent levels of Sp35 mRNA, but the level of Sp35 mRNA more than doubled in mature oligodendrocytes (MBP$^+$).

Exogenous Sp35-Fc Promotes Survival/Proliferation/Differentiation of Oligodendrocytes We evaluated Sp35 mRNA expression in oligodendrocytes at various developmental stages by the following method. Oligodendrocytes were induced to differentiate as described in Example 1, and mRNA was isolated using the Ambion kit. Quantitation of Sp35 mRNA expression was carried out using the Taqman® RT-PCR kit (Applied Biosystems) according to manufacturer's specifications, using the following primers: 5'-CTTTCCCCTTCGACATCAAGAC-3' (forward; SEQ ID NO:50) and 5'-CAGCAGCACCAGGCAGAA-3' (reverse; SEQ ID NO:51); and a FAM-labeled probe, 5'-ATCGCCAC-CACCATGGGCTTCAT-3' (SEQ ID NO:52). Data were normalized to GAPDH levels as an internal control. Early progenitor oligodendrocytes (A2B5+) and pre-myelinating oligodendrocytes (O4+) showed equivalent levels of Sp35 mRNA, but the level of Sp35 mRNA more than doubled in mature oligodendrocytes (MBP+). FIG. 7.

Figure 8:
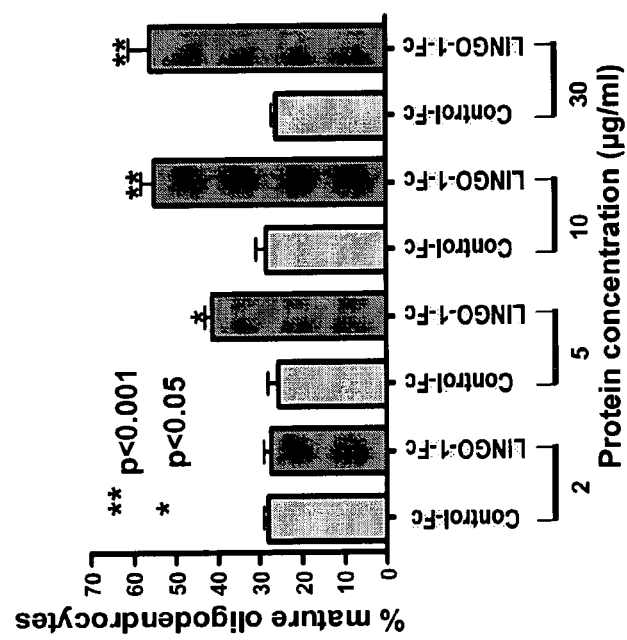
FIG. 8—Dose-dependent differentiation of oligodendrocytes after exogenous LINGO-1-Fc treatment compared to treatment with a control-Fc polypeptide. Data were quantified by counting the number of mature oligodendrocytes (identified by the presence of myelin sheets) as a percentage of total O4+ oligodendrocytes. For each sample, approximately 800 cells were counted.

A2B5+ oligodendrocytes, prepared as described in Example 1, were treated with increasing concentrations of Sp35-Fc or control-Fc for 3 days (Sp35-Fc was prepared as described in Example 2). For assessing differentiation, A2B5+ cells were plated in 4-well slide chambers in FGF/PDGF-free growth medium supplemented with 10 ng/ml CNTF and 15 nM triiodo-L-thyronine and were immediately treated with increasing concentrations of Sp35-Fc or control-Fc. After 48 h (72 h for RNAi), cultures were stained with antibody to O4, and the number of total O4+ and mature O4+ oligodendrocytes was quantified. Samples were analyzed in duplicate. Sp35-Fc promoted differentiation of A2B5+ cells into O4+ cells in a concentration dependent manner. FIG. 8.

Mature oligodendrocytes have a half-life in vitro of about 48 to 72 hours, with cells typically undergoing apoptosis after 72 hours. When oligodendrocyte cultures were treated with Sp35-Fc (10 µg/ml for 5 days), we observed a significantly increased survival rate for mature oligodendrocytes, as judged by cell viability staining as compared to control treated with control-Fc. MBP expression was monitored as a marker for mature ologodendrocytes. An approximately 3-fold increase in MBP protein expression was observed in Sp35-Fc treated cells by cell staining and Western blot using anti-MBP antibody compared to control-Fc treated cells.

Example 4

Sp35 Antagonists Regulate RhoA and Fyn

A strong candidate signaling pathway that is implicated in the control of oligodendrocyte differentiation is the Rho family of GTPases. Rho GTPases regulate cellular morphology, and reduced RhoA-GTP amounts are required for oligodendrocyte differentiation. See Liang, X, et al., *J. Neurosci.* 24:7140-7149 (2004). To determine whether Sp35 signals through the RhoA pathway, RhoAGTP levels in cell lysates of oligodendrocytes treated with Sp35-Fc were compared with levels in the corresponding control via western blotting. A significant threefold reduction in RhoA-GTP was seen after Sp35-Fc (FIG. 9A), indicating that attenuation of Sp35 function may induce oliogodendrocyte differentiation by down-regulating RhoAGTP, with a subsequent increase in MBP expression. Similar reductions in RhoA GTP amounts were seen when oligodendrocytes were treated with DN-Sp35 or with Sp35 RNAi (data not shown).

Figure 9:
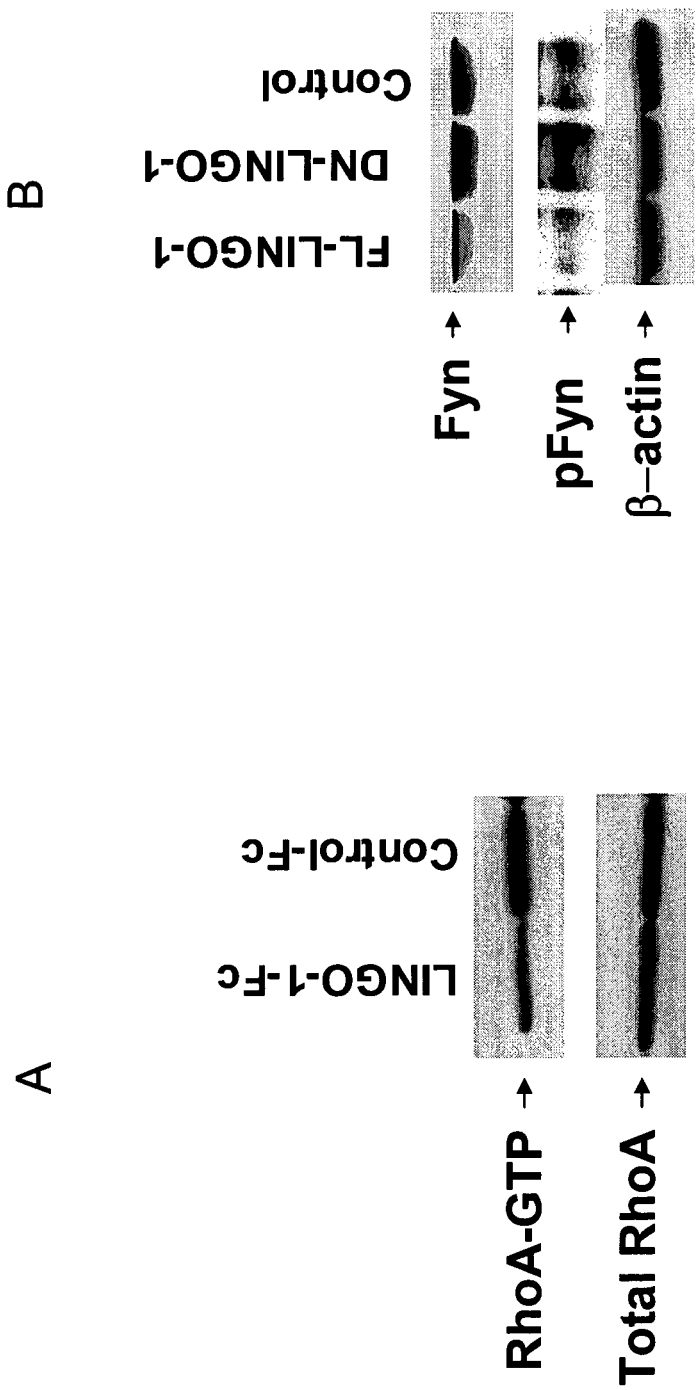
FIG. 9—LINGO-1 (Sp35) antagonists regulate RhoA and Fyn. (A) RhoA-GTP amounts in oligodendrocytes treated with LINGO-1-Fc, as detected by western blotting. (B) Fyn expression and phosphorylation (pFyn) in oligodendrocytes infected with lentivirus carrying FL-LINGO-1, DN-LINGO-1 or control plasmids, as detected by western blotting.

The activity of RhoA GTPase is regulated by Fyn kinase See Liang, X, et al., *J. Neurosci.* 24:7140-7149 (2004). Increased Fyn expression and phosphorylation correlate with oligodendrocyte differentiation. Id. See also Osterhout, D. J., et al., *J. Cell Biol.* 145:1209-1218 (1999). To test if Sp35 antagonists affect Fyn function, Fyn expression and phosphorylation were measured directly by western blotting. DN-Sp35 treatment, as described in Example 1, resulted in two-fold increases in Fyn protein and in Fyn phosphorylation (FIG. 9B). Conversely, when cells expressing FL-Sp35 were analyzed, Fyn expression and phosphorylation were reduced by twofold (FIG. 9B).

Example 5

Sp35-Fc Promotes Myelination In Vitro

The role of Sp35 in myelination was examined in vitro by treating co-cultures of dorsal root ganglion (DRG) neurons and oligodendrocytes with Sp35-Fc and testing for myelination by immunohistochemistry and electron microscopy. For these studies, it was necessary to first generate primary cultures of DRG neurons and of oligodendrocytes.

Female Long Evans rat E14-E17 embryonic dorsal root ganglia were cultured as described by Plant et al., *J. Neurosci.* 22:6083-91 (2002). Dissected DRGs were plated on poly-L-lysine-coated cover slips (100 µg/ml) for 2 weeks in the presence of fluorodeoxyuridine for days 2-6 and days 8-11 in NLA medium containing 1× B27, 100 ng/ml NGF (Invitrogen).

A2B5$^+$ oligodendrocytes were prepared as described in Example 1, and were harvested by trypsinization.

For coculture studies, A2B5$^+$ oligodendrocytes were added to DRG neuron drop cultures in the presence or absence of 10 µg/ml Sp35-Fc. The culture medium (Neurobasal medium supplemented with B27 and 100 ng/ml NGF) was changed, and fresh Sp35-Fc was added to the cells every 3 d. To identify changes in myelination, 2-week-old cultures were stained by immunohistochemical staining ("IHC") for neurofilaments with anti-βIII-tubulin antibody to identify axons, or anti-MBP antibody to identify oligodendrocytes., and 4-week-old cultures were subjected to SDS-PAGE followed by western blot analyses to quantify the MBP. In selected examples, cells were fixed for electron microscopy studies by adding 2.5% gluteraldehyde directly onto the cover slips. Myelinated axons in the 2-week-old cultures were quantified by counting the number of myelinated internode bundles that were derived from single MBP$^+$ oligodendrocytes. Samples were analyzed in duplicate. Error bars denote individual determinations. P values in all studies were determined using a one-way analysis of variance.

Figure 10A:
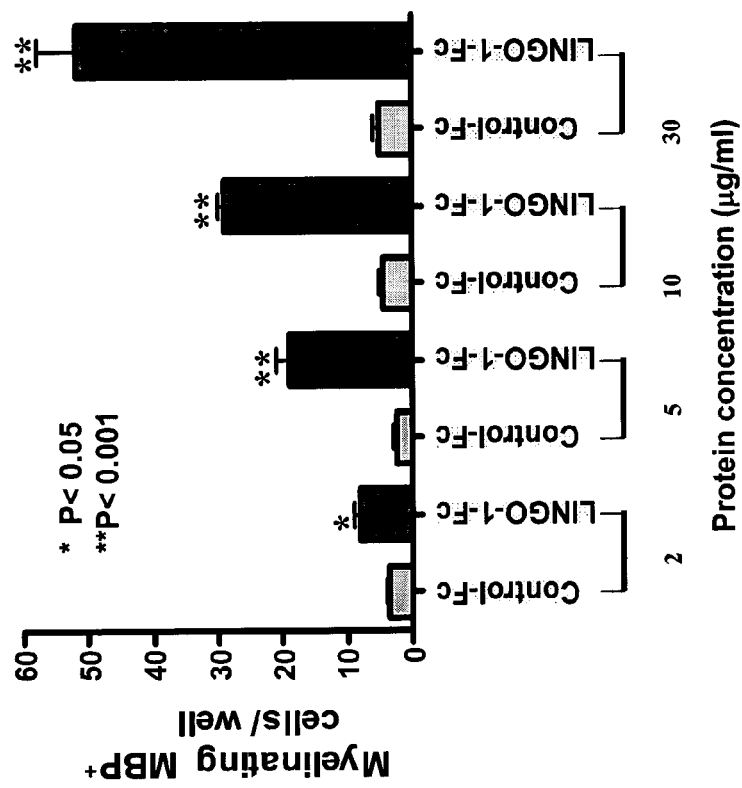
FIG. 10A—LINGO-1 antagonists promote axonal myelination by oligodendrocytes. Quantitative analysis of myelination in cocultures that were treated with LINGO-1-Fc (10 µg/ml) for 2 weeks. For each sample, ten fields of cells stained for MBP$^+$ were counted.
Figure 10B:
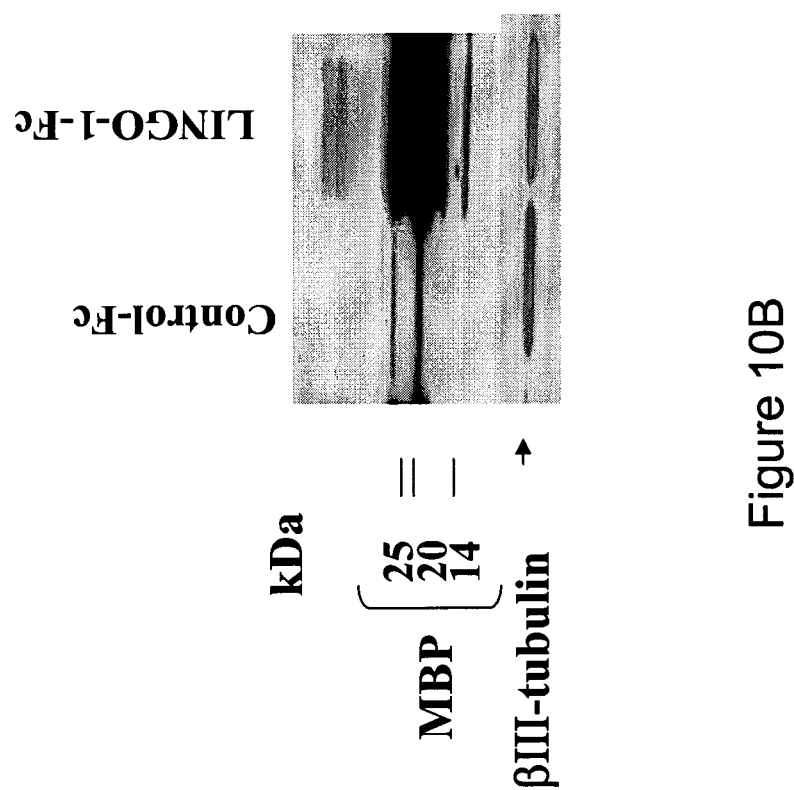
FIG. 10B—Western blots of 4-week cocultures treated with exogenous LINGO-1-Fc and a control-Fc polypeptide using anti-MBP antibody to detect the presence of the MBP protein.
Figures 10C, 10D:
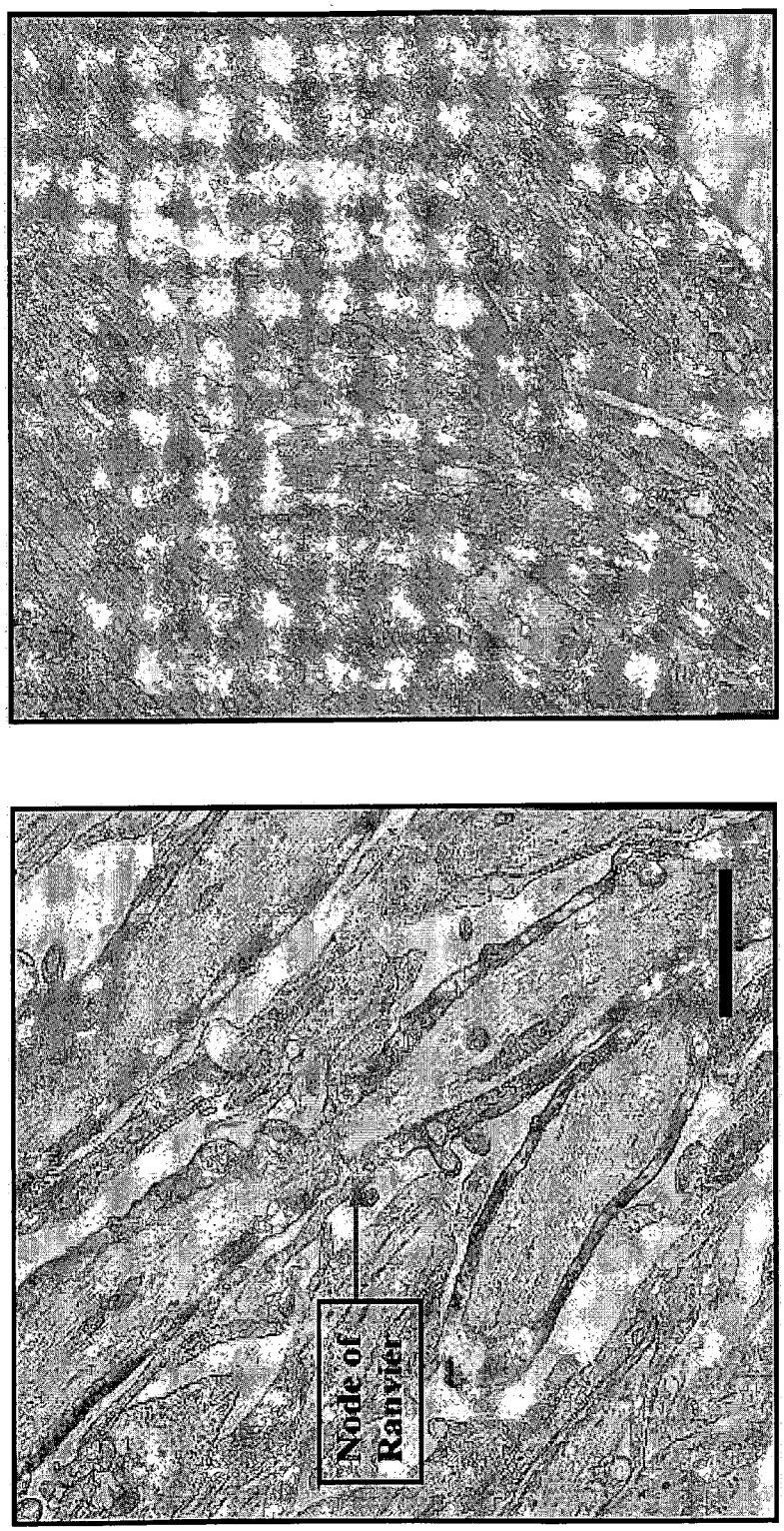
FIGS. 10C and 10D—Electron microscopy analysis of cocultures that were treated with LINGO-1-Fc (C) or control Fc (D) for 4 weeks. Node of Ranvier structure is indicated. Scale bar, 1.5 µm.

In cultures of rat primary oligodendrocytes and dorsal root ganglion (DRG) neurons, low basal amounts of myelination were observed. In contrast, treatment with Sp35-Fc for 2 weeks resulted in robust axonal myelination, as was evident by the presence of MBP$^+$ myelinated axons, which developed in Sp35-Fc treated cultures in a dose-dependent manner (FIG. 10A). Western blot analysis demonstrated that expression of MBP, the major protein component of myelin, was increased in Sp35-Fc-treated cultures (FIG. 10B). Myelination in the presence of Sp35-Fc was further confirmed by confocal microscopy, which verified that MBP had encapsulated the axons (data not shown). Multiple wellformed internodes were observed by electron microscopy in cultures treated with Sp35-Fc, as well as structures that closely resembled nodes of Ranvier (FIG. 10C). Only occasional myelinated segments and no nodes of Ranvier were detected in the control cultures (FIG. 10D).

Figure 10F:
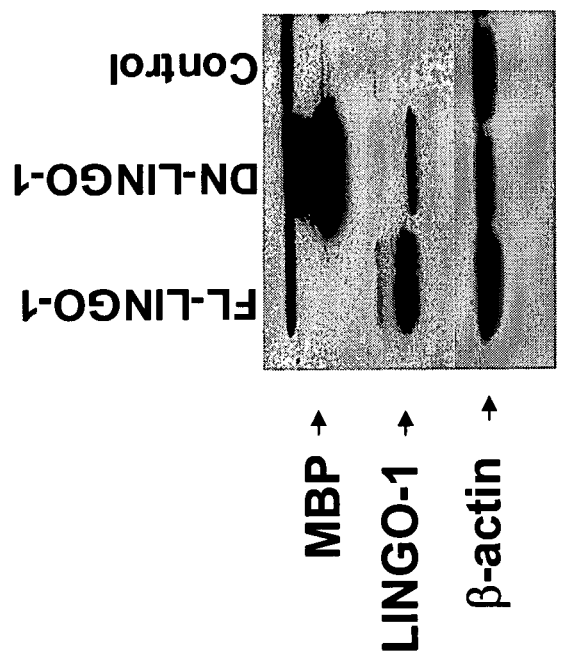
FIGS. 10E and 10F—Myelination in cocultures that were infected with FL-LINGO-1, DN-LINGO-1 and control lentivirus for two weeks. MBP$^+$ cells were counted by immunofluorescence (E). Western blots from cultures infected with FL-LINGO-1, DN-LINGO-1 and control lentivirus analyzed for MBP and for LINGO-1 using an antibody to the hemagglutinin tag (F).
Figure 10E:
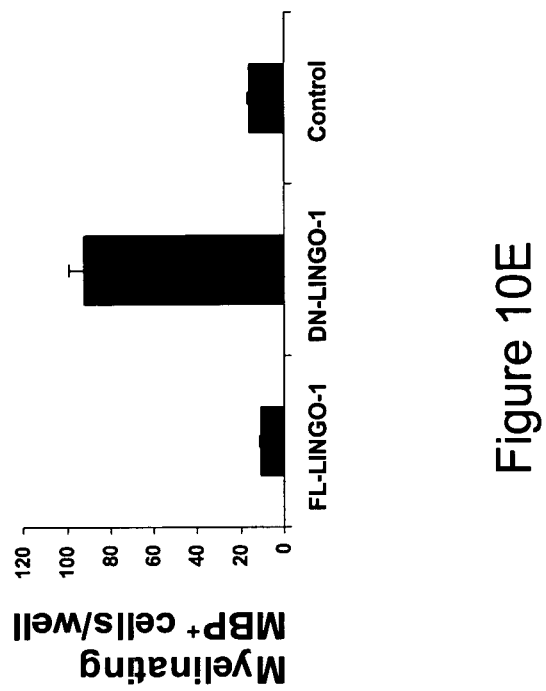

The effect of Sp35 antagonists on axonal myelination was further confirmed using DN-Sp35. Expression of DN-Sp35 increased the total number of myelinating MBP$^+$ cells five- to tenfold when compared with controls (FIG. 10E). In contrast, overexpression of FL-Sp35 decreased the number of myelinating MBP$^+$ cells twofold, as compared with controls (FIG. 10E). Western blot analysis was used to quantify MBP in the cultures. DN-Sp35 produced a tenfold increase in MBP, whereas FL-Sp35 caused a twofold reduction in MBP (FIG. 10F). Expression of FL-Sp35 and DN-Sp35 proteins in cultures was confirmed by western blotting (FIG. 10F). These studies further indicate that endogenous Sp35 inhibits myelination and that antagonism of Sp35 can reverse the inhibition.

Example 6

Ig Domain Peptides of Sp35 Promote Myelination In Vitro

Several peptides containing portions of the Ig domain of Sp35 were examined in vitro, by treating co-cultures of dorsal root ganglion (DRG) neurons and oligodendrocytes with Sp35 Ig peptides and testing for myelination as described in Example 5.

For co-culture studies, A2B5$^+$ oligodendrocytes were added to DRG neuron drop cultures in the presence or absence of 10 µg/ml Sp35-Ig-Fc (Sp35 amino acids 417-493 fused to Fc). The culture medium (Neurobasal medium supplemented with B27 and 100 ng/ml NGF) was changed, and fresh Sp35-Ig-Fc was added to the cells every 3 d. To identify changes in myelination, 2-week-old cultures were stained by immunohistochemical staining ("IHC") for neurofilaments with anti-βIII-tubulin antibody to identify axons, or anti-MBP antibody to identify oligodendrocytes and 4-week-old cultures were subjected to SDS-PAGE followed by western blot analyses to quantify the MBP.

Figure 15:
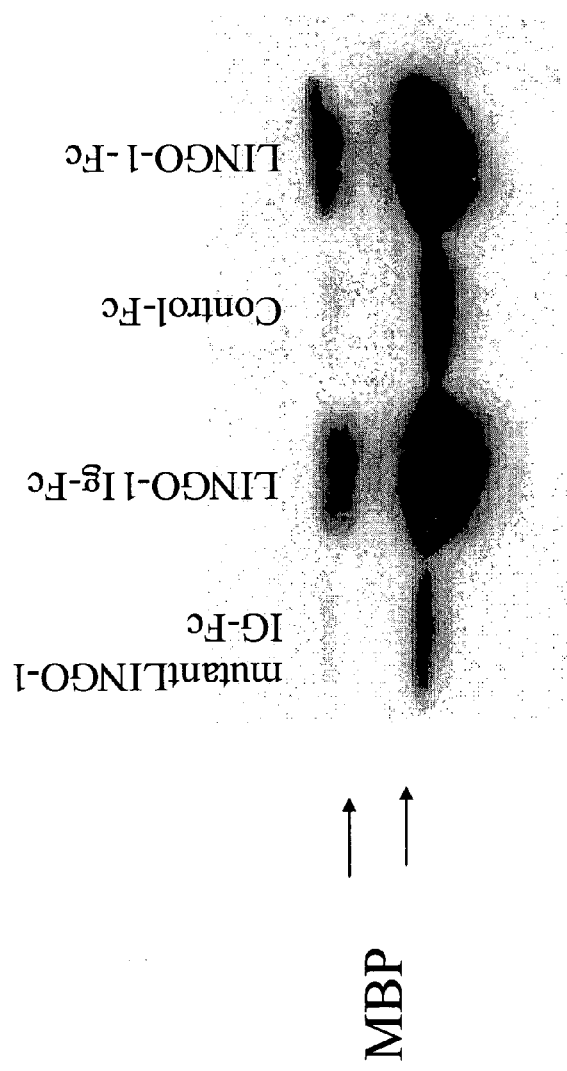
FIG. 15—Western blot of cocultures treated with exogenous LINGO-1-Ig-Fc, mutant LINGO-1-Ig-Fc (arginine at position 456 changed to histiding), LINGO-1-Fc and a control-Fc polypeptide using anti-MBP antibody to detect the presence of the MBP protein.

Western blot analysis demonstrated that expression of MBP, the major protein component of myelin, was increased in Sp35-Ig-Fc treated cultures (FIG. 15). A mutated Sp35-Ig-Fc peptide was also tested in the same assay. When the arginine at position 456 and histidine at position 458 were mutated to glutamic acid and valine respectively, the peptides did not promote myelination as compared to the Sp35-Ig-Fc peptide. (FIG. 15). The arginine at position 456 is part of the "RKH loop" (Arginine-Lysine-Histidine amino acids 456-458) in the Ig domain of Sp35 and is though to be important for Sp35 antagonist polypeptide binding. The increase in MBP protein in the presence of Sp35-Ig-Fc is comparable to the increase in MPB protein in the presence of the Sp35-Fc molecule. (FIG. 15).

Figure 16:
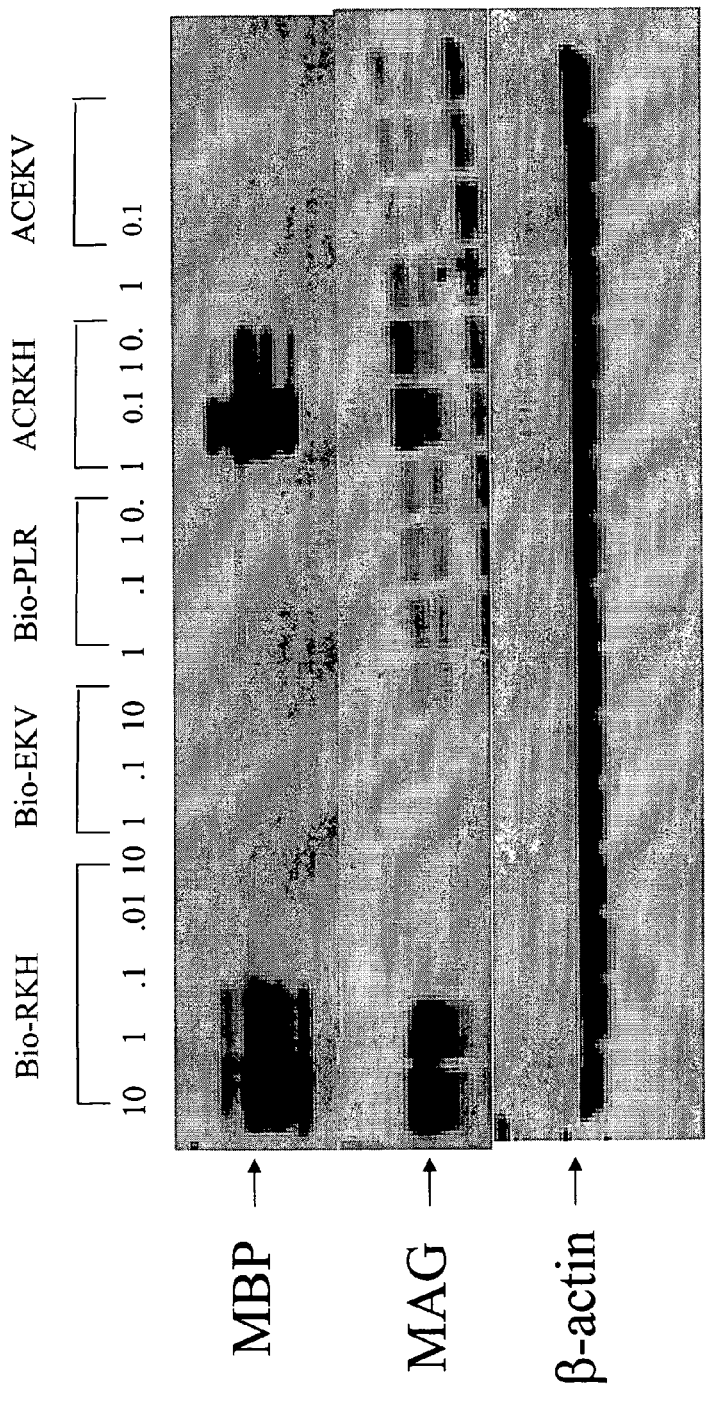
FIG. 16—Western blot of 4 cocultures treated with exogenous LINGO-1-Ig cyclic peptides and mutated LINGO-1-Ig cyclic peptides, as described in Example 6, using anti-MBP antibody to detect the presence of the MBP protein.

Cyclic peptides containing portions of the Sp35 Ig domain were also tested for their ability to promote myelination in the assay described in Example 5. The Sp35 peptide LSPRKH (amino acids 454-458) (SEQ ID NO:61) was cyclized by the addition of a cysteine on the N-terminus and a cysteine residue on the C-terminus. The peptide was capped with an acetyl (Ac) group at the N-terminus and $NH_2$ moiety at its C-terminus. Additionally, the LSPRKH (SEQ ID NO:61) peptide was also synthesized with a biotin group linked by the amino acid linker GSGC on the N-terminus and a cysteine residue-$NH_2$ on the C-terminus and is cyclized. The resulting cyclic Sp35 peptides, Ac-CLSPRKHC (SEQ ID NO:66), and Biotin-GS-GCLSPRKHC (SEQ ID NO:63) increased expression of MBP, the major protein component of myelin, in treated cultures as shown in Western blots. (FIG. 16). Other cyclic peptides were used as controls: biotin-GSGCLSPEKVC (SEQ ID NO:65), biotin-GSGCKHSPLRC (SEQ ID NO:64) and Ac-CLSPEKVC (SEQ ID NO:67). All of the control peptides showed no increase in MBP in treated co-cultures. (FIG. 16).

These studies further indicate that smaller peptides of the Ig domain of Sp35 can act as an Sp35 antagonist to releave myelination inhibition by Sp35.

Example 7

DN-Sp35 Acts in DRG Neurons and Oligodendrocytes to Promote Myelination

Figure 10G:
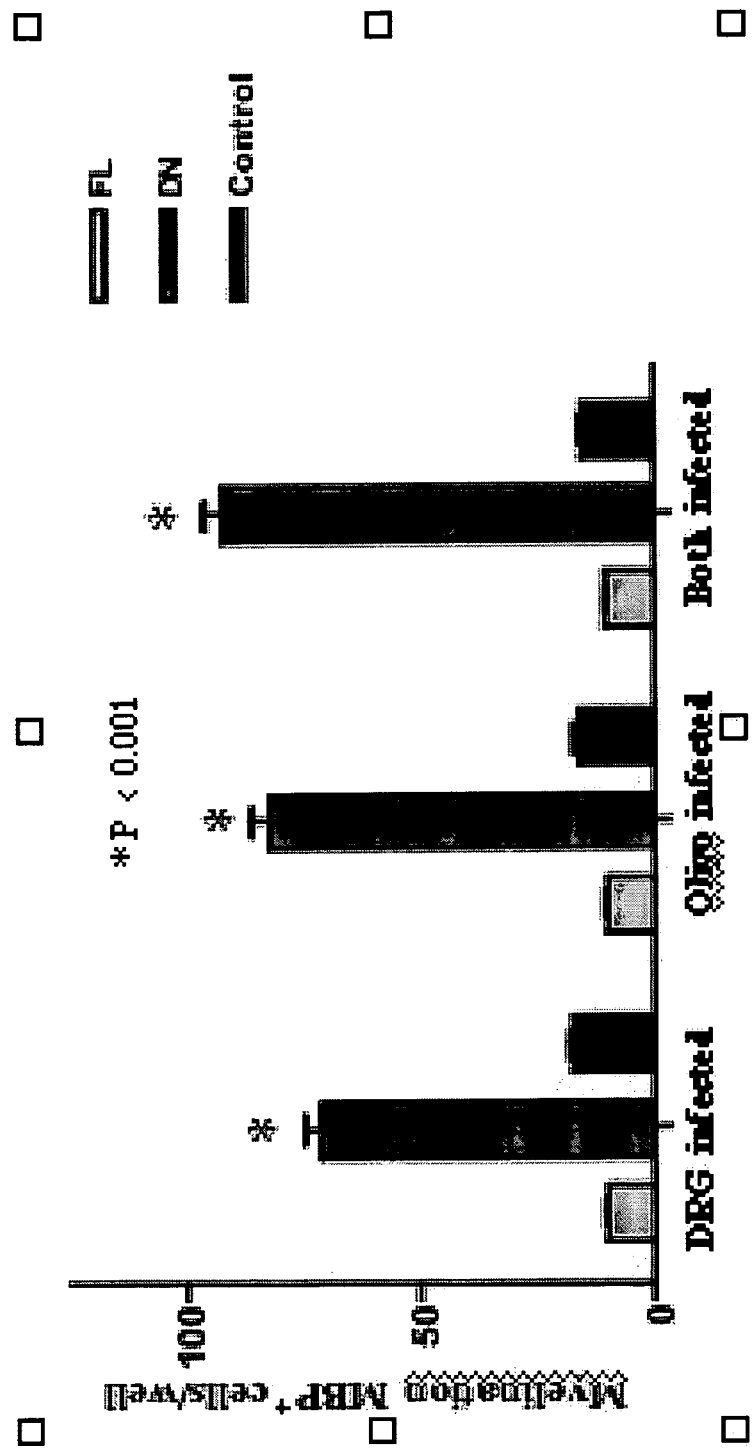
FIG. 10G—Myelination in cocultures in which only the dorsal root ganglion cells (DRG infected) or oligodendrocytes (oligo infected) or both (both infected) have been infected with FL-LINGO-1, DN-LINGO-1 and control lentivirus.

We performed experiments to address the relative contributions to the myelination process of Sp35 in DRG neurons as compared to oligodendrocytes. We infected DRG neurons, oligodendrocytes and co-cultures (prepared as described in Example 5) with the FL-Sp35 and DN-Sp35 lentiviral vectors described in Example 1 and performed immunohistochemical straining for myelinated MBP cells after two weeks. A 2-fold increase in MBP levels in co-cultures where both cells express DN-Sp35 and a 2-fold decrease in MBP levels in co-cultures where both cells express FL-Sp35 was observed (FIG. 10G).

Overexpression of FL-Sp35 in either or both cell types significantly descreased basal levels of myelination in comparison to control (empty vector). On the other hand, overexpression of DN-Sp35 in either or both cell types increased basal levels of myelination 2- to 3-fold compared to control (FIG. 10G). Exogenously added Sp35-Fc reversed the inhibition of myelination by overexpression of FL-Sp35 in either or both cell types. In addition, exogenous Sp35-Fc further enhanced myelination if either cell type overexpresses DN-Sp35 alone and had slight effects if both cell types overexpress DN-Sp35. These studies indicate that expression of a dominant negative Sp35 protein in both oligodendrocytes and in DRG neurons, or treatment with Sp35-Fc protein, contributes to effective myelination.

Example 8

Sp35-Knockout Mice Exhibit Early Onset Myelination

Sp35-knockout mice were generated with a GFP/Neo (green fluorescent protein/neomycin) replacement vector that targeted the entire, single exon coding sequence of Sp35 as described by Schiemann et al. (*Science* 293: 2111-2114 (2001). Mouse genomic 129/SvJ DNA was isolated from a lambda genomic library (Stratagene #946313). A 14.6-kb EcoRV fragment was subcloned into pBSK$^+$ and then was targeted by homologous recombination in bacteria to insert the eGFP Q40 reporter gene at the initiating ATG. The final construct deleted the entire 1-1,841 nucleotides of the single-exon coding sequence of Sp35. This construct was used to target the Sp35 locus in D3 (129/Sv) embryonic stem cells. Correctly targeted cells were identified by Southern blotting of EcoRI-digested embryonic stem cell DNA and were injected into C57Bl/6 blastocysts to generate chimeric mice. Chimeras were crossed to C57Bl/6 mice to generate heterozygous founder mice. Genotypes were determined by three-primer PCR of tail DNA. The forward primer, 5'-CTATCCAAGCACTGCCTGCTC-3' (SEQ ID NO:53), and the two reverse primers, 5'-GAGTTCTAGCTCCTC-CAGGTGTG-3' (SEQ ID NO:54) and 5'-GATGCCCT-TCAGCTCGATGCG-3' (SEQ ID NO:55), yielded 275-bp wild-type and 356-bp mutant allele products, respectively, in a 35-cycle reaction (94 1C for 20 s, 65 1C. for 30 s, 72 1C. for 30 s). See Mi, S. et al., *Nat. Neurosci.* 7: 221-228 (2004). Validation of Sp35 gene deletion was accomplished by Southern blot, RTPCR and northern blot analyses. Prominent bands were detected in northern blot and RT-PCR in wild-type mice, but a complete absence of bands was found in the knockout mice. Southern blots of the heterozygotes showed both the wild-type and modified Sp35 allele. Sp35 knockout mice appeared normal, with no obvious physical abnormalities or alterations in behavior, locomotion or fecundity. The heterozygous F1 offspring litter mates varied in size.

Figure 11:
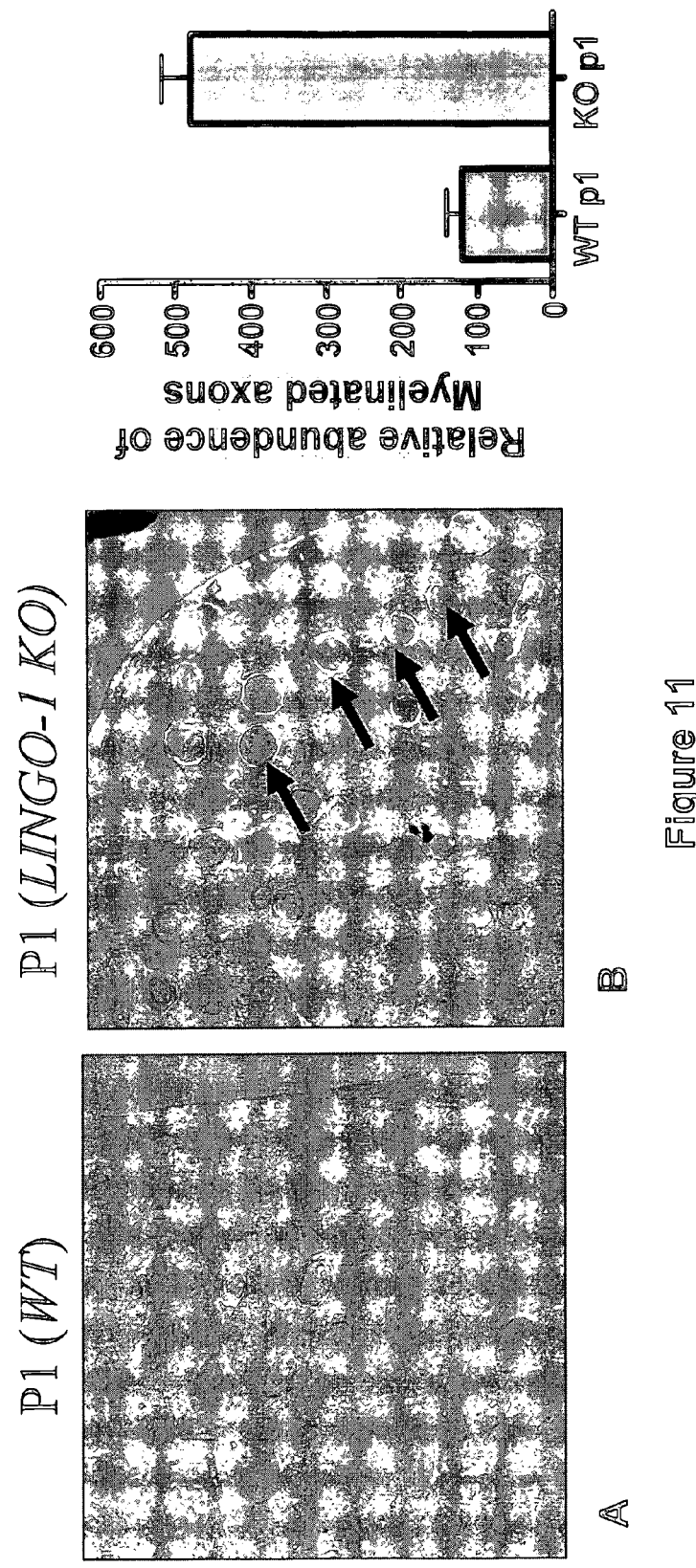
FIGS. 11A and 11B—Electron microscopy showing (A) visual and (B) quantitative analysis of myelinated axon fibers in LINGO-1 knockout and wild-type spinal cords from P1 mice. Four spinal cords were analyzed; for each sample, myelinated axon fibers from ten fields were counted. Data shown are the mean values from all the measurements.

Cultured oligodendrocytes from Sp35 knockout mice were evaluated by IHC for potential changes in differentiation. Oligodendrocytes that were more highly differentiated and a larger percentage of mature oligodendrocytes were observed in Sp35 knockout than in cultures from wild-type littermates. Because the onset of myelination in normal mouse development typically occurs on postnatal day (P) 5, we next examined myelination in P1 spinal cords from the wild-type and knockout mice by electronmicroscopy. Consistent with the in vitro cultures, spinal cords from Sp35 knockout mice contained more myelinated axon fibers than did their wild-type littermates FIG. 11. No obvious changes in peripheral nervous system sciatic nerve were detected in the knockout mice, suggesting that the myelination effects were limited to the CNS.

Co-cultured DRG and oligodendrocytes from the knock-out mice showed more DRG and oligodendrocyte interaction and myelination. Co-cultured DRG and oligodendrocytes from the Sp35 knock-out mice show more oligodendrocyte differentiation and myelination. When spinal cord tissue from the knock out mice are examined by electron microscopy, the newborn Sp35 knockout mice (postnatal day 1 (P1) and day 6 (P6)) show more myelination fiber than their wild-type litter mates.

Transgenic mice which over-express wild-type Sp35 were also generated according to the method of Hogan B., Manipulating the Mouse Embryo. A Laboratory Manual. Cold Spring Harbor Press (1986), pp. 153-183. When the transgenic mice which over-express Sp35 were examined by electron microscopy, the newborn mice (postnatal day 8 (P8)) showed less myelination fiber than their wild-type litter mates.

Example 9

Sp35-Fc Promotes Oligodendrocyte Survival and Myelination In Vivo

Adult wild-type C57Bl/6 male mice were fed cuprizone (0.2% milled with ground mouse chow by weight) for 6 weeks to induce demyelination within the corpus callosum. Sp35-Fc was stereotactically injected into the demyelinating corpus callosum at 2, 2.5, and 3 weeks of cuprizone feeding. Control mice were stereotactically injected at the same intervals with sterilized media containing no Sp35-Fc. After 6 weeks of cuprizone feeding, the mice were returned to a normal diet for 2, 4 and 6 weeks (ground mouse chow only) to allow remyelination.

The cuprizone-treated mice were anesthetized with ketamine (80 mg/kg body weight) and xylazine (10 mg/kg body weight) and positioned in an immobilization apparatus designed for stereotactic surgery (David Kopf Instruments). The scalp was opened and the sterile compounds injected (1 µM in 1 ml of HBSS) unilaterally into the acutely demyelinated corpus callosum of the wild-type recipient mice with a 10 ml Hamilton syringe using stereotactic coordinates of 0.7 mm posterior and 0.3 mm lateral to bregma at a depth of 1.7 mm (Messier et al., *Pharmacol. Biochem. Behav.* 63(2): 313-18 (1999)). Additionally, control recipient mice were stereotactically injected with HBSS containing no compounds. The opening in the skull was filled with Gelfoam, and the area was swabbed with penicillin and streptomycin (Gibco) and the wound was sutured. Post injection, mice were sacrificed every week of the experiment and their brains were removed and processed for molecular, biochemical and histological analysis.

Figure 12:
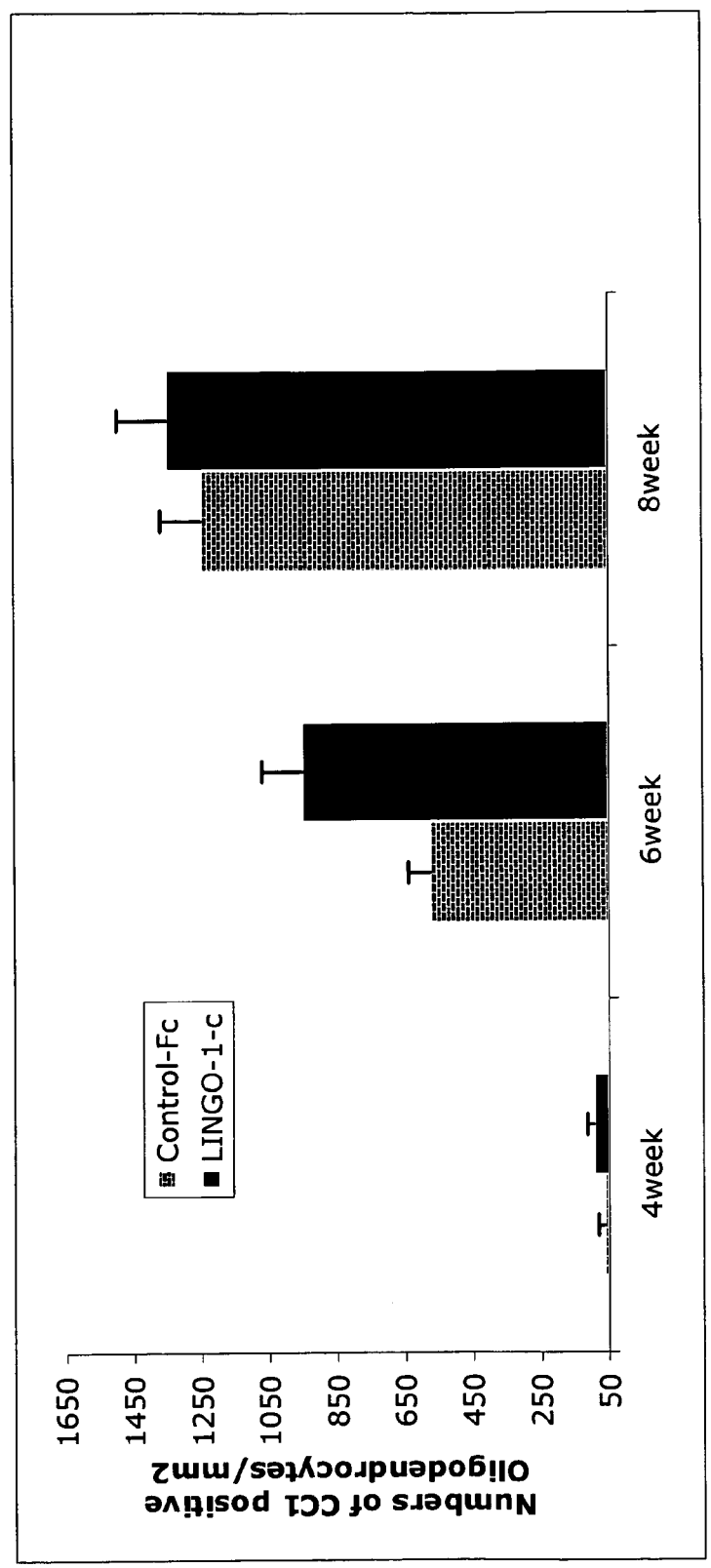
FIG. 12—Cuprizone-treated mice were surgically injected with Sp35-Fc (LINGO-1-Fc) or a control polypeptide as described herein. The animals receiving Sp35-Fc treatment showed increased mature oligodendrocyte survival (based on CC1 antibody staining).

The animals receiving Sp35-Fc treatment showed increased mature oligodendrocyte survival (based on CC1 antibody staining, FIG. 12) and axon myelination by IHC using anti-MBP protein antibody or luxol fast blue (data not shown).

Example 10

In Vivo Transplantation of Sp35-Transformed Cells

We also investigate the biological function of Sp35 in spinal cord injury. We infect cortical primary cultured cells (mixed cultures) with retrovirus expressing Sp35 or a retrovirus control, for delivery into the injured epicenter of rat spinal cords. $2 \times 10^6$ cells are introduced, and the rats are sacrificed at day 10. The spinal cords are fixed in 4% paraformaldehyde overnight, then dehydrated in 70% ethanol, followed by 95% ethanol. Tissue samples are imbedded in paraffin. Sections (10 microns thick) are used for immunohistochemical staining. We monitor oligodendrocyte survival and axon myelination in the injured rats receiving Sp35. We see more oligodendrocyte and axon myelination and less axon retraction in the animals receiving cells which express Sp35.

The Sp35 retrovirus construct for these experiments has been made as follows. The Sp35 gene was PCR amplified using primers 5'-GATTACTCGAGATGCTGGCGGGGGGCGTGAGG-3' (SEQ ID NO:56), containing an XhoI site, and 5'CGCGGGAATTCTCATATCATCTTCATGTTGAACTTG-3' (SEQ ID NO:57), containing an EcoRI site. The PCR product was digested with XhoI and EcoRI, then ligated into the Retrovirus vector pMIG (which contains IRES-GFP), which was previously cleaved with XhoI and EcoRI. The new vector was named pMMC078. All isolates of pMMC078 contained inadvertent point mutations, so two isolates of pMMC078 were ligated together. pMMC078.6 was cut with XhoI and AccI and pMMC078.7 was cut with XhoI and AccI. These two fragments were ligated together to make the final correct plasmid, pMMC089. The DNA sequence of the insert was confirmed by DNA sequencing. Sp35 retrovirus was made as described.

293G cells were split the day before transfection. 8 µg Sp35-retrovirus DNA was used to transfect $5 \times 10^6$ cells by lipofectamine (Invitrogen). The condition medium was harvested after 92 hours post-transfection. The conditioned medium was centrifuged at 5000 g for 10 minutes, and the supernatant used as a Sp35 retrovirus stock. This stock was stored at 4° C. for 1 week or −80° C. for 6 months.

Example 11

Sp35-Fc Promotes Neuronal and Oligodendrocyte Survival After Spinal Cord Injury (SCI) In Vivo Spinal cord injury was induced in adult female Long Evans rats (190-210 g; Charles River). A dorsal hemisection was performed at T6/T7, completely interrupting the main dorsomedial and the minor dorsolateral corticospinal tract (CST) components. The cord was sterotaxically transected at a depth of 1.8 mm from the surface using a microscalpel. Immediately after CST transection, an intrathecal catheter was inserted into the subarachnoid space at T7 and connected to a primed mini-osmotic pump (Alzet model 2004, Alza Corp.) inserted into the subcutaneous space. The mini-osmotic pumps delivered 0.25 µl/h of 25 µM Sp35-Fc fusion protein or either human IgG (5 mg/ml) or PBS as control. Postoperative care comprised analgesia (Buprenorphine/Buprenex, Reckitt Benckiset Healthcare Ltd., 0.05 mg/kg subcutaneously) every 8-12 hours for 3 days and antibiotic treatment (ampicillin, Bristol Myers Squibb, 100 mg/kg subcutaneously twice daily) for 7 days after surgery. Bladders were expressed manually twice a day for the duration of the study (4 weeks) or until return of function. On completion of the study, rats were anesthetized and trans-cardially perfused with heparinized saline followed by 4% paraformaldehyde (PFA). The spinal cords were removed, embedded in paraffin, and 10 µm sections were cut from for histological analysis.

To quantify apoptotic cell death after SCI, animals were euthanized 3 or 7 days after SCI and stained using anti-activated-Caspase-3 antibody (Cell Signaling Technologies) and TUNEL staining (Promega). The sections were also stained with anti-NeuN antibody (Chemicon) and anti-CC1 antibody (Calbiochem) to identify neurons and oligodendrocytes, respectively.

We observed extensive TUNEL staining both rostral and caudal to the site of transection 3 days after SCI and activated-Caspase-3 staining co-localized with both neurons and oligodendrocytes. The number of activated-Caspase-3-positive neurons and oligodendrocytes was significantly smaller in the Sp35-Fc-treated animals than in the controls 3 days after SCI. Furthermore, four weeks after SCI, more neurons and oligodendrocytes survived in the spinal cord tissue surrounding the lesion site in Sp35-Fc-treated animals that in controls base on staining with anti-βIII-tubulin antibody (neuronal survival) and anti-O4 antibody (oligodendrocyte survival).

Example 12

Sp35-Fc Reduces Caspase-3 Activation and Cell Death In Vitro

PC12 cells (Neuroscreen) were differentiated in RPMI-1640 medium supplemented with 5% fetal bovine serum, 10% horse serum, 2 mM glutamine, 100 U/ml penicillin and 100 mg/ml streptomycin containing 200 ng/ml NGF for 7 days. For experiments, the culture media was replaced with NGF-free culture media containing Sp35-Fc, human IgG as a negative control (0.1-10 µM), or zVAD as a positive control (0.1 µM). 18 hours after NGF withdrawal, activated Caspase-3 was quantified using the Caspase 3/7 Glo kit (Promega) according to the manufacturer's instructions. 42 hours after NGF withdrawal, apoptotic cell death was quantified using a cell death detection ELISA kit (Roche) according to the manufacturer's instructions.

Figure 13:
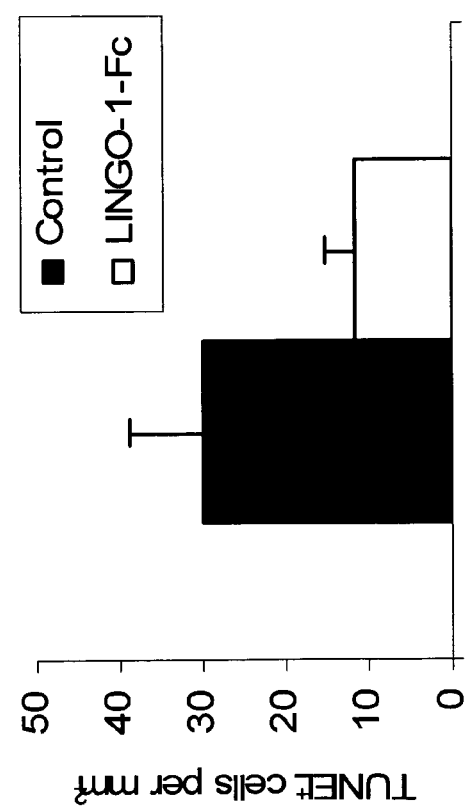
FIG. 13—TUNEL assay of differentiated PC12 cells 18 hours after NGF withdrawal treated with Sp35-Fc (LINGO-1-Fc) or a control. The Sp35-Fc treated cells had fewer cells undergoing apoptosis.
Figure 14:
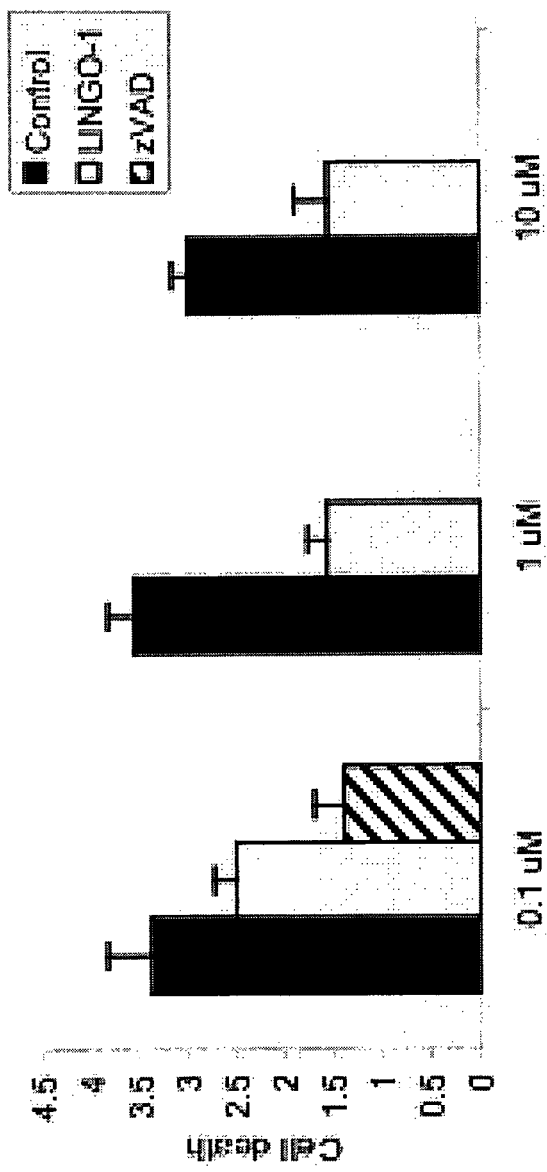
FIG. 14—Apoptosis in differentiated PC12 cells deprived of trophic support 18 hours after the removal of NGF from the culture media treated with Sp35-Fc (LINGO-1), the caspase inhibitor zVAD or a control polypeptide. Cells treated with the control polypeptide showed the most cell death.

We observed that 0.1 µM Sp35-Fc reduced Caspase-3 activation in differentiated PC12 cells deprived of trophic support 18 hours after the removal of NGF from the culture media. The effect of Sp35-Fc on Caspase-3 activation was dose-dependent and at higher doses (1 or 10 µM) it was as effective as a neuroprotective dose of the caspase inhibitor zVAD (0.1 µM) (FIG. 14). As an additional measure of cell death, we quantified apoptosis using a TUNEL ELISA method and found that Sp35-Fc significantly reduced cell death measured 42 hours after withdrawal of NGF (FIG. 13).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications mentioned in this specification are herein incorporated by reference to the same extent as if each individual publication or patent application was specifically and individually indicated to be incorporated by reference.

What is claimed is:

1. A method for promoting differentiation or survival of an oligodendrocyte, comprising contacting an oligodendrocyte with an Sp35 antagonist, wherein the Sp35 antagonist is an Sp35 antibody or fragment thereof that is capable of promoting myelination in in vitro co-cultures of oligodendrocytes and neurons.

2. The method of claim 1, wherein said Sp35 antibody or fragment thereof is selected from the group consisting of: a polyclonal antibody, a monoclonal antibody, a multispecific antibody, a human antibody, a humanized antibody, a primatized antibody, a chimeric antibody or a single chain antibody.

3. The method of claim 1, wherein said Sp35 antagonist can bind specifically to an epitope of SEQ ID NO:2.

4. The method of claim 1, wherein said oligodendrocyte is in a mammal, and wherein said contacting comprises administering said Sp35 antagonist.

5. The method of claim 4, wherein said Sp35 antagonist is administered by an administration route selected from the group consisting of: bolus injection; infusion; and direct administration into the central nervous system.

6. The method of claim 4 wherein said mammal is human.

7. The method of claim 4, wherein the Sp35 antagonist is administered parenterally.

8. The method of claim 4, wherein said mammal has been diagnosed with multiple sclerosis.

9. The method of claim 8, wherein said Sp35 antagonist is administered by an administration route selected from the group consisting of bolus injection; infusion; and direct administration into a chronic lesion of MS.

10. The method of claim 8, wherein the multiple sclerosis is relapsing remitting multiple sclerosis.

11. The method of claim 8, wherein the multiple sclerosis is secondary progressive multiple sclerosis.

12. The method of claim 8, wherein the multiple sclerosis is primary progressive multiple sclerosis.

13. The method of claim 8, wherein the Sp33 antagonist is administered parenterally.

14. A method for promoting oligodendrocyte-mediated myelination of a neuron, comprising contacting a mixture of a neuron and an oligodendrocyte with an Sp35 antagonist, wherein the Sp35 antagonist is an Sp35 antibody or fragment thereof that is capable of promoting myelination in in vitro co-cultures of oligodendrocytes and neurons.

15. The method of claim 14, wherein said Sp35 antibody or fragment thereof is selected from the group consisting of: a polyclonal antibody, a monoclonal antibody, a multispecific antibody, a human antibody, a humanized antibody, a primatized antibody, a chimeric antibody or a single chain antibody.

16. The method of claim 14, wherein said Sp35 antagonist can bind specifically to an epitope of SEQ ID NO:2.

17. The method of claim 14, wherein said oligodendrocyte is in a mammal, and wherein said contacting comprises administering said Sp35 antagonist.

18. The method of claim 17, wherein said mammal has been diagnosed with multiple sclerosis.

19. The method of claim 18, wherein said Sp35 antagonist is administered by an administration route selected from the group consisting of: bolus injection; chronic infusion; and directly into a chronic lesion of MS.

20. The method of claim 18, wherein the Sp35 antagonist is administered parenterally.

* * * * *

UNITED STATES PATENT AND TRADEMARK OFFICE
CERTIFICATE OF CORRECTION

| | | |
|---|---|---|
| PATENT NO. | : 8,486,893 B2 | Page 1 of 1 |
| APPLICATION NO. | : 11/165576 | |
| DATED | : July 16, 2013 | |
| INVENTOR(S) | : Sha Mi, R. Blake Pepinsky and John McCoy | |

It is certified that error appears in the above-identified patent and that said Letters Patent is hereby corrected as shown below:

Column 2, Title Page, Item (57) Abstract
Lines 1-2, delete "disorsers" and insert -- disorders --.

In the Claims:

Column 109, Claim 2
Line 25, delete "or" and insert -- and --.

Column 109, Claim 6
Line 35, delete "claim 4" and insert -- claim 4, --.

Column 110, Claim 13
Line 18, delete "Sp33" and insert -- Sp35 --.

Column 110, Claim 15
Line 30, delete "or" and insert -- and --.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,486,893 B2 | Page 1 of 1 |
| APPLICATION NO. | : 11/165576 | |
| DATED | : July 16, 2013 | |
| INVENTOR(S) | : Mi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 494 days.

Signed and Sealed this
Twenty-first Day of October, 2014

Michelle K. Lee
*Deputy Director of the United States Patent and Trademark Office*

SEQUENCE LISTING

```
<160> NUMBER OF SEQ ID NOS: 100

<210> SEQ ID NO 1
<211> LENGTH: 1845
<212> TYPE: DNA
<213> ORGANISM: Homo sapiens

<400> SEQUENCE: 1
atgctggcgg ggggcgtgag gagcatgccc agcccctcc tggcctgctg gcagcccatc      60
ctcctgctgg tgctgggctc agtgctgtca ggctcggcca cgggctgccc gccccgctgc     120
gagtgctccg cccaggaccg cgctgtgctg tgccaccgca agcgctttgt ggcagtcccc     180
gagggcatcc ccaccgagac gcgcctgctg gacctaggca gaaccgcat caaaacgctc      240 aaccaggacg agttcgccag cttcccgcac ctggaggagc tggagctcaa cgagaacatc     300
gtgagcgccg tggagcccgg cgccttcaac aacctcttca acctccggac gctgggtctc     360
cgcagcaacc gcctgaagct catcccgcta ggcgtcttca ctggcctcag caacctgacc     420
aagctggaca tcagcgagaa caagattgtt atcctgctgg actacatgtt tcaggacctg     480
tacaacctca agtcactgga ggttggcgac aatgacctcg tctacatctc tcaccgcgcc     540
ttcagcggcc tcaacagcct ggagcagctg acgctggaga aatgcaacct gacctccatc     600
cccaccgagg cgctgtccca cctgcacggc ctcatcgtcc tgaggctccg gcacctcaac     660
atcaatgcca tccgggacta ctccttcaag aggctctacc gactcaaggt cttggagatc     720
tcccactggc cctacttgga caccatgaca cccaactgcc tctacggcct caacctgacg     780
tccctgtcca tcacacactg caatctgacc gctgtgccct acctggccgt ccgccaccta     840
gtctatctcc gcttcctcaa cctctcctac aaccccatca gcaccattga gggctccatg     900
ttgcatgagc tgctccggct gcaggagatc cagctggtgg gcgggcagct ggccgtggtg     960
gagccctatg ccttccgcgg cctcaactac ctgcgcgtgc tcaatgtctc tggcaaccag    1020
ctgaccacac tggaggaatc agtcttccac tcggtgggca acctggagac actcatcctg    1080
gactccaacc cgctggcctg cgactgtcgg ctcctgtggg tgttccggcg ccgctggcgg    1140
ctcaacttca accggcagca gcccacgtgc gccacgcccg agtttgtcca gggcaaggag    1200
ttcaaggact ccctgatgt gctactgccc aactacttca cctgccgccg cgcccgcatc     1260
cgggaccgca aggcccagca ggtgtttgtg gacgagggcc acacggtgca gtttgtgtgc    1320
cgggccgatg gcgacccgcc gccgccatc ctctggctct caccccgaaa gcacctggtc     1380
tcagccaaga gcaatgggcg gctcacagtc ttccctgatg gcacgctgga ggtgcgctac    1440
gcccaggtac aggacaacgg cacgtacctg tgcatcgcgc ccaacgcggg cggcaacgac    1500
```

-continued

```
tccatgcccg cccacctgca tgtgcgcagc tactcgcccg actggcccca tcagcccaac    1560
aagaccttcg ctttcatctc caaccagccg ggcgagggag aggccaacag cacccgcgcc    1620
actgtgcctt tccccttcga catcaagacc ctcatcatcg ccaccaccat gggcttcatc    1680
tctttcctgg gcgtcgtcct cttctgcctg gtgctgctgt ttctctggag ccggggcaag    1740
ggcaacacaa agcacaacat cgagatcgag tatgtgcccc gaaagtcgga cgcaggcatc    1800
agctccgccg acgcgccccg caagttcaac atgaagatga tatga                   1845
```

<210> SEQ ID NO 2
<211> LENGTH: 614
<212> TYPE: PRT
<213> ORGANISM: Homo sapiens

<400> SEQUENCE: 2

```
Met Leu Ala Gly Gly Val Arg Ser Met Pro Ser Pro Leu Leu Ala Cys
1               5                   10                  15

Trp Gln Pro Ile Leu Leu Val Leu Gly Ser Val Leu Ser Gly Ser
            20                  25                  30

Ala Thr Gly Cys Pro Pro Arg Cys Glu Cys Ser Ala Gln Asp Arg Ala
        35                  40                  45

Val Leu Cys His Arg Lys Arg Phe Val Ala Val Pro Glu Gly Ile Pro
    50                  55                  60

Thr Glu Thr Arg Leu Leu Asp Leu Gly Lys Asn Arg Ile Lys Thr Leu
65                  70                  75                  80

Asn Gln Asp Glu Phe Ala Ser Phe Pro His Leu Glu Glu Leu Glu Leu
                85                  90                  95

Asn Glu Asn Ile Val Ser Ala Val Glu Pro Gly Ala Phe Asn Asn Leu
            100                 105                 110

Phe Asn Leu Arg Thr Leu Gly Leu Arg Ser Asn Arg Leu Lys Leu Ile
        115                 120                 125

Pro Leu Gly Val Phe Thr Gly Leu Ser Asn Leu Thr Lys Leu Asp Ile
    130                 135                 140

Ser Glu Asn Lys Ile Val Ile Leu Leu Asp Tyr Met Phe Gln Asp Leu
145                 150                 155                 160

Tyr Asn Leu Lys Ser Leu Glu Val Gly Asp Asn Asp Leu Val Tyr Ile
                165                 170                 175

Ser His Arg Ala Phe Ser Gly Leu Asn Ser Leu Glu Gln Leu Thr Leu
            180                 185                 190

Glu Lys Cys Asn Leu Thr Ser Ile Pro Thr Glu Ala Leu Ser His Leu
        195                 200                 205

His Gly Leu Ile Val Leu Arg Leu Arg His Leu Asn Ile Asn Ala Ile
    210                 215                 220

Arg Asp Tyr Ser Phe Lys Arg Leu Tyr Arg Leu Lys Val Leu Glu Ile
225                 230                 235                 240

Ser His Trp Pro Tyr Leu Asp Thr Met Thr Pro Asn Cys Leu Tyr Gly
                245                 250                 255

Leu Asn Leu Thr Ser Leu Ser Ile Thr His Cys Asn Leu Thr Ala Val
            260                 265                 270

Pro Tyr Leu Ala Val Arg His Leu Val Tyr Leu Arg Phe Leu Asn Leu
        275                 280                 285

Ser Tyr Asn Pro Ile Ser Thr Ile Glu Gly Ser Met Leu His Glu Leu
    290                 295                 300

Leu Arg Leu Gln Glu Ile Gln Leu Val Gly Gly Gln Leu Ala Val Val
305                 310                 315                 320
```

```
Glu Pro Tyr Ala Phe Arg Gly Leu Asn Tyr Leu Arg Val Leu Asn Val
                325                 330                 335

Ser Gly Asn Gln Leu Thr Thr Leu Glu Ser Val Phe His Ser Val
            340                 345                 350

Gly Asn Leu Glu Thr Leu Ile Leu Asp Ser Asn Pro Leu Ala Cys Asp
                355                 360                 365

Cys Arg Leu Leu Trp Val Phe Arg Arg Trp Arg Leu Asn Phe Asn
    370                 375                 380

Arg Gln Gln Pro Thr Cys Ala Thr Pro Glu Phe Val Gln Gly Lys Glu
385                 390                 395                 400

Phe Lys Asp Phe Pro Asp Val Leu Leu Pro Asn Tyr Phe Thr Cys Arg
                405                 410                 415

Arg Ala Arg Ile Arg Asp Arg Lys Ala Gln Gln Val Phe Val Asp Glu
                420                 425                 430

Gly His Thr Val Gln Phe Val Cys Arg Ala Asp Gly Asp Pro Pro
                435                 440                 445

Ala Ile Leu Trp Leu Ser Pro Arg Lys His Leu Val Ser Ala Lys Ser
    450                 455                 460

Asn Gly Arg Leu Thr Val Phe Pro Asp Gly Thr Leu Glu Val Arg Tyr
465                 470                 475                 480

Ala Gln Val Gln Asp Asn Gly Thr Tyr Leu Cys Ile Ala Ala Asn Ala
                485                 490                 495

Gly Gly Asn Asp Ser Met Pro Ala His Leu His Val Arg Ser Tyr Ser
                500                 505                 510

Pro Asp Trp Pro His Gln Pro Asn Lys Thr Phe Ala Phe Ile Ser Asn
    515                 520                 525

Gln Pro Gly Glu Gly Glu Ala Asn Ser Thr Arg Ala Thr Val Pro Phe
    530                 535                 540

Pro Phe Asp Ile Lys Thr Leu Ile Ile Ala Thr Thr Met Gly Phe Ile
545                 550                 555                 560

Ser Phe Leu Gly Val Val Leu Phe Cys Leu Val Leu Leu Phe Leu Trp
                565                 570                 575

Ser Arg Gly Lys Gly Asn Thr Lys His Asn Ile Glu Ile Glu Tyr Val
                580                 585                 590

Pro Arg Lys Ser Asp Ala Gly Ile Ser Ser Ala Asp Ala Pro Arg Lys
            595                 600                 605

Phe Asn Met Lys Met Ile
            610

<210> SEQ ID NO 3
<211> LENGTH: 1845
<212> TYPE: DNA
<213> ORGANISM: Mus sp.

<400> SEQUENCE: 3
atgctggcag ggggtatgag aagcatgccc agccccctcc tggcctgctg gcagcccatc     60
ctcctgctgg tactgggctc agtgctgtca ggctctgcta caggctgccc gccccgctgc    120
gagtgctcag cgcaggaccg agccgtgctc tgccaccgca acgctttgt ggcggtgccc     180 gagggcatcc ccaccgagac tcgcctgctg acctgggca aaaccgcat caagacactc     240 aaccaggacg agtttgccag cttcccacac ctggaggagc tagaactcaa tgaaaacatc    300
gtgagcgccg tggagccagg cgccttcaac aacctcttca acctgaggac tctggggctg    360
cgcagcaacc gcctgaagct tatcccgctg ggcgtcttca ccggcctcag caacttgacc    420
aagctggaca tcagtgagaa caagatcgtc atcctgctag actacatgtt ccaagaccta    480
```

```
tacaacctca agtcgctgga ggtcggcgac aacgacctcg tctacatctc ccatcgagcc    540
ttcagcggcc tcaacagcct ggaacagctg acgctggaga atgcaatct gacctccatc    600
cccacggagg cgctctccca cctgcacggc tcatcgtcc tgcggctacg acatctcaac    660
atcaatgcca tcagggacta ctccttcaag aggctgtacc gacttaaggt cttagagatc    720
tcccactggc cctacctgga caccatgacc cccaactgcc tctacggcct caacctgaca    780
tccctatcca tcacgcactg caacctgaca gccgtgccct atctggcagt gcgtcacctg    840
gtctatctcc gtttcctcaa ccttttcctac aacccaatcg gtacaatcga gggctccatg    900
ctgcatgagc tgctgcggtt gcaggagatc cagctggtgg gcgggcagct ggccgtggtg    960
gagccctatg cctttcgtgg gctcaactac ctgcgtgtgc tcaatgtctc tggcaaccag   1020
ctgaccaccc tggaggagtc agccttccat tcggtgggca acctggagac gctcatcctg   1080
gactccaacc cactggcctg tgactgccgg ctgctgtggg tgttccggcg ccgctggcgg   1140
ctcaacttca caggcagca gcccacctgc gccacacctg agttcgtcca gggcaaagag   1200
ttcaaggact ttccggatgt actcctaccc aactacttca cctgccgccg ggcccacatc   1260
cgggaccgca aggcacagca ggtgtttgta gatgagggcc acacggtgca gtttgtatgc   1320
cgggcagatg gcgaccctcc accagctatc ctttggctct caccccgcaa gcacttggtc   1380
tcggccaaga gcaatgggcg gctcacagtc ttccctgatg gcacgctgga ggtgcgctac   1440
gcccaggtac aggacaacgg cacgtacctg tgcatcgcag ccaatgctgg cggcaacgac   1500
tccatgcccg cccacttgca tgtgcgcagc tactcgcctg actggcccca tcaacccaac   1560
aagaccttcg ccttcatctc caaccagcca ggcgagggag aggccaacag cacccgcgcc   1620
actgtgcctt tccccttcga catcaagacg ctcattatcg ccaccaccat gggcttcatc   1680
tccttcctgg gcgttgtcct attctgcctg gtgctgctgt ttctatggag ccggggcaaa   1740
ggcaacacaa agcacaacat cgaaattgag tatgtgcccc ggaaatcgga cgcaggcatc   1800
agctcagctg atgcaccccg caagttcaac atgaagatga tatga              1845
```

<210> SEQ ID NO 4
<211> LENGTH: 614
<212> TYPE: PRT
<213> ORGANISM: Mus sp.

<400> SEQUENCE: 4

```
Met Leu Ala Gly Gly Met Arg Ser Met Pro Ser Pro Leu Leu Ala Cys
1               5                   10                  15

Trp Gln Pro Ile Leu Leu Val Leu Gly Ser Val Leu Ser Gly Ser
            20                  25                  30

Ala Thr Gly Cys Pro Pro Arg Cys Glu Cys Ser Ala Gln Asp Arg Ala
        35                  40                  45

Val Leu Cys His Arg Lys Arg Phe Val Ala Val Pro Glu Gly Ile Pro
    50                  55                  60

Thr Glu Thr Arg Leu Leu Asp Leu Gly Lys Asn Arg Ile Lys Thr Leu
65                  70                  75                  80

Asn Gln Asp Glu Phe Ala Ser Phe Pro His Leu Glu Glu Leu Glu Leu
                85                  90                  95

Asn Glu Asn Ile Val Ser Ala Val Glu Pro Gly Ala Phe Asn Asn Leu
                100                 105                 110

Phe Asn Leu Arg Thr Leu Gly Leu Arg Ser Asn Arg Leu Lys Leu Ile
            115                 120                 125

Pro Leu Gly Val Phe Thr Gly Leu Ser Asn Leu Thr Lys Leu Asp Ile
```

```
                130                 135                 140
Ser Glu Asn Lys Ile Val Ile Leu Leu Asp Tyr Met Phe Gln Asp Leu
145                 150                 155                 160

Tyr Asn Leu Lys Ser Leu Glu Val Gly Asp Asn Asp Leu Val Tyr Ile
                165                 170                 175

Ser His Arg Ala Phe Ser Gly Leu Asn Ser Leu Glu Gln Leu Thr Leu
                180                 185                 190

Glu Lys Cys Asn Leu Thr Ser Ile Pro Thr Glu Ala Leu Ser His Leu
                195                 200                 205

His Gly Leu Ile Val Leu Arg Leu Arg His Leu Asn Ile Asn Ala Ile
                210                 215                 220

Arg Asp Tyr Ser Phe Lys Arg Leu Tyr Arg Leu Lys Val Leu Glu Ile
225                 230                 235                 240

Ser His Trp Pro Tyr Leu Asp Thr Met Thr Pro Asn Cys Leu Tyr Gly
                245                 250                 255

Leu Asn Leu Thr Ser Leu Ser Ile Thr His Cys Asn Leu Thr Ala Val
                260                 265                 270

Pro Tyr Leu Ala Val Arg His Leu Val Tyr Leu Arg Phe Leu Asn Leu
                275                 280                 285

Ser Tyr Asn Pro Ile Gly Thr Ile Glu Gly Ser Met Leu His Glu Leu
290                 295                 300

Leu Arg Leu Gln Glu Ile Gln Leu Val Gly Gln Leu Ala Val Val
305                 310                 315                 320

Glu Pro Tyr Ala Phe Arg Gly Leu Asn Tyr Leu Arg Val Leu Asn Val
                325                 330                 335

Ser Gly Asn Gln Leu Thr Thr Leu Glu Glu Ser Ala Phe His Ser Val
                340                 345                 350

Gly Asn Leu Glu Thr Leu Ile Leu Asp Ser Asn Pro Leu Ala Cys Asp
                355                 360                 365

Cys Arg Leu Leu Trp Val Phe Arg Arg Trp Arg Leu Asn Phe Asn
                370                 375                 380

Arg Gln Gln Pro Thr Cys Ala Thr Pro Glu Phe Val Gln Gly Lys Glu
385                 390                 395                 400

Phe Lys Asp Phe Pro Asp Val Leu Leu Pro Asn Tyr Phe Thr Cys Arg
                405                 410                 415

Arg Ala His Ile Arg Asp Arg Lys Ala Gln Gln Val Phe Val Asp Glu
                420                 425                 430

Gly His Thr Val Gln Phe Val Cys Arg Ala Asp Gly Asp Pro Pro Pro
                435                 440                 445

Ala Ile Leu Trp Leu Ser Pro Arg Lys His Leu Val Ser Ala Lys Ser
450                 455                 460

Asn Gly Arg Leu Thr Val Phe Pro Asp Gly Thr Leu Glu Val Arg Tyr
465                 470                 475                 480

Ala Gln Val Gln Asp Asn Gly Thr Tyr Leu Cys Ile Ala Ala Asn Ala
                485                 490                 495

Gly Gly Asn Asp Ser Met Pro Ala His Leu His Val Arg Ser Tyr Ser
                500                 505                 510

Pro Asp Trp Pro His Gln Pro Asn Lys Thr Phe Ala Phe Ile Ser Asn
                515                 520                 525

Gln Pro Gly Glu Gly Glu Ala Asn Ser Thr Arg Ala Thr Val Pro Phe
                530                 535                 540

Pro Phe Asp Ile Lys Thr Leu Ile Ile Ala Thr Thr Met Gly Phe Ile
545                 550                 555                 560
```

-continued

```
Ser Phe Leu Gly Val Val Leu Phe Cys Leu Val Leu Leu Phe Leu Trp
            565                 570                 575
Ser Arg Gly Lys Gly Asn Thr Lys His Asn Ile Glu Ile Glu Tyr Val
        580                 585                 590
Pro Arg Lys Ser Asp Ala Gly Ile Ser Ser Ala Asp Ala Pro Arg Lys
    595                 600                 605
Phe Asn Met Lys Met Ile
    610

<210> SEQ ID NO 5
<211> LENGTH: 6
<212> TYPE: PRT
<213> ORGANISM: Homo sapiens

<400> SEQUENCE: 5

Met Gln Val Ser Lys Arg
1               5

<210> SEQ ID NO 6
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is any Basic Amino Acid

<400> SEQUENCE: 6

Ile Thr Xaa Xaa Xaa
1               5

<210> SEQ ID NO 7
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is any Basic Amino Acid

<400> SEQUENCE: 7

Ala Cys Xaa Xaa Xaa
1               5

<210> SEQ ID NO 8
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is any Basic Amino Acid

<400> SEQUENCE: 8

Val Cys Xaa Xaa Xaa
1               5

<210> SEQ ID NO 9
<211> LENGTH: 5
<212> TYPE: PRT
<213> ORGANISM: Homo sapiens
<220> FEATURE:
<221> NAME/KEY: MISC_FEATURE
<222> LOCATION: (3)..(5)
<223> OTHER INFORMATION: Xaa is any Basic Amino Acid

<400> SEQUENCE: 9
```

```
Ser Pro Xaa Xaa Xaa
1               5

<210> SEQ ID NO 10
<211> LENGTH: 5
<212> TYPE: PRT
<213> ORGANISM: Homo sapiens

<400> SEQUENCE: 10

Ser Pro Arg Lys His
1               5

<210> SEQ ID NO 11
<211> LENGTH: 5
<212> TYPE: PRT
<213> ORGANISM: Homo sapiens

<400> SEQUENCE: 11

Ser Pro Arg Lys Lys
1               5

<210> SEQ ID NO 12
<211> LENGTH: 5
<212> TYPE: PRT
<213> ORGANISM: Homo sapiens

<400> SEQUENCE: 12

Ser Pro Arg Lys Arg
1               5

<210> SEQ ID NO 13
<211> LENGTH: 5
<212> TYPE: PRT
<213> ORGANISM: Homo sapiens

<400> SEQUENCE: 13

Ser Pro Lys Lys His
1               5

<210> SEQ ID NO 14
<211> LENGTH: 5
<212> TYPE: PRT
<213> ORGANISM: Homo sapiens

<400> SEQUENCE: 14

Ser Pro His Lys His
1               5

<210> SEQ ID NO 15
<211> LENGTH: 5
<212> TYPE: PRT
<213> ORGANISM: Homo sapiens

<400> SEQUENCE: 15

Ser Pro Arg Arg His
1               5

<210> SEQ ID NO 16
<211> LENGTH: 5
<212> TYPE: PRT
<213> ORGANISM: Homo sapiens

<400> SEQUENCE: 16

Ser Pro Arg His His
1               5
```

```
<210> SEQ ID NO 17
<211> LENGTH: 5
<212> TYPE: PRT
<213> ORGANISM: Homo sapiens

<400> SEQUENCE: 17

Ser Pro Arg Arg Arg
1               5

<210> SEQ ID NO 18
<211> LENGTH: 5
<212> TYPE: PRT
<213> ORGANISM: Homo sapiens

<400> SEQUENCE: 18

Ser Pro His His His
1               5

<210> SEQ ID NO 19
<211> LENGTH: 5
<212> TYPE: PRT
<213> ORGANISM: Homo sapiens

<400> SEQUENCE: 19

Ser Pro Lys Lys Lys
1               5

<210> SEQ ID NO 20
<211> LENGTH: 6
<212> TYPE: PRT
<213> ORGANISM: Homo sapiens

<400> SEQUENCE: 20

Ile Thr Pro Lys Arg Arg
1               5

<210> SEQ ID NO 21
<211> LENGTH: 5
<212> TYPE: PRT
<213> ORGANISM: Homo sapiens

<400> SEQUENCE: 21

Ala Cys His His Lys
1               5

<210> SEQ ID NO 22
<211> LENGTH: 5
<212> TYPE: PRT
<213> ORGANISM: Homo sapiens

<400> SEQUENCE: 22

Val Cys His His Lys
1               5

<210> SEQ ID NO 23
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 23

Xaa Xaa Arg Lys His
1               5
```

```
<210> SEQ ID NO 24
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 24

Xaa Xaa Arg Arg Arg
1               5

<210> SEQ ID NO 25
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 25

Xaa Xaa Lys Lys Lys
1               5

<210> SEQ ID NO 26
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 26

Xaa Xaa His His His
1               5

<210> SEQ ID NO 27
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 27

Xaa Xaa Arg Lys Lys
1               5

<210> SEQ ID NO 28
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 28

Xaa Xaa Arg Lys Arg
1               5

<210> SEQ ID NO 29
<211> LENGTH: 5
<212> TYPE: PRT
```

```
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 29

Xaa Xaa Lys Lys His
1               5

<210> SEQ ID NO 30
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 30

Xaa Xaa His Lys His
1               5

<210> SEQ ID NO 31
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 31

Xaa Xaa Arg Arg His
1               5

<210> SEQ ID NO 32
<211> LENGTH: 5
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 32

Xaa Xaa Arg His His
1               5

<210> SEQ ID NO 33
<211> LENGTH: 9
<212> TYPE: PRT
<213> ORGANISM: Homo sapiens

<400> SEQUENCE: 33

Arg Arg Ala Arg Ile Arg Asp Arg Lys
1               5

<210> SEQ ID NO 34
<211> LENGTH: 9
<212> TYPE: PRT
<213> ORGANISM: Homo sapiens

<400> SEQUENCE: 34

Lys Lys Val Lys Val Lys Glu Lys Arg
1               5

<210> SEQ ID NO 35
```

```
<211> LENGTH: 9
<212> TYPE: PRT
<213> ORGANISM: Homo sapiens

<400> SEQUENCE: 35

Arg Arg Leu Arg Leu Arg Asp Arg Lys
1               5

<210> SEQ ID NO 36
<211> LENGTH: 9
<212> TYPE: PRT
<213> ORGANISM: Homo sapiens

<400> SEQUENCE: 36

Arg Arg Gly Arg Gly Arg Asp Arg Lys
1               5

<210> SEQ ID NO 37
<211> LENGTH: 9
<212> TYPE: PRT
<213> ORGANISM: Homo sapiens

<400> SEQUENCE: 37

Arg Arg Ile Arg Ala Arg Asp Arg Lys
1               5

<210> SEQ ID NO 38
<211> LENGTH: 19
<212> TYPE: DNA
<213> ORGANISM: Artificial Sequence
<220> FEATURE:
<223> OTHER INFORMATION: Rat RT-PCR Forward Primer

<400> SEQUENCE: 38
agagacatgc gattggtga                                          19

<210> SEQ ID NO 39
<211> LENGTH: 21
<212> TYPE: DNA
<213> ORGANISM: Artificial Sequence
<220> FEATURE:
<223> OTHER INFORMATION: Rat RT-PCR Reverse Primer

<400> SEQUENCE: 39
agagatgtag acgaggtcat t                                       21

<210> SEQ ID NO 40
<211> LENGTH: 55
<212> TYPE: DNA
<213> ORGANISM: Artificial Sequence
<220> FEATURE:
<223> OTHER INFORMATION: LV1-035 (sense oligo)

<400> SEQUENCE: 40
tgatcgtcat cctgctagac ttcaagagag tctagcagga tgacgatctt ttttc  55

<210> SEQ ID NO 41
<211> LENGTH: 59
<212> TYPE: DNA
<213> ORGANISM: Artificial Sequence
<220> FEATURE:
<223> OTHER INFORMATION: LV1-036 (antisense oligo)

<400> SEQUENCE: 41
tcgagaaaaa agatcgtcat cctgctagac tctcttgaag tctagcagga tgacgatca  59
```

<210> SEQ ID NO 42
<211> LENGTH: 59
<212> TYPE: DNA
<213> ORGANISM: Artificial Sequence
<220> FEATURE:
<223> OTHER INFORMATION: LV1-035 Control

<400> SEQUENCE: 42
tgatcctcat ccttctatac ttcaagagag tgtagcagga tgacgatctt ttttctcga    59

<210> SEQ ID NO 43
<211> LENGTH: 59
<212> TYPE: DNA
<213> ORGANISM: Artificial Sequence
<220> FEATURE:
<223> OTHER INFORMATION: LV1-036 Control

<400> SEQUENCE: 43
tcgagaaaaa agatcgtcat cctgctagac tctcttgaag tatagaagga tgacgatca    59

<210> SEQ ID NO 44
<211> LENGTH: 41
<212> TYPE: DNA
<213> ORGANISM: Artificial Sequence
<220> FEATURE:
<223> OTHER INFORMATION: FL-Sp35 Primer

<400> SEQUENCE: 44
gaggatctcg acgcggccgc atggagacag acacactcct g    41

<210> SEQ ID NO 45
<211> LENGTH: 41
<212> TYPE: DNA
<213> ORGANISM: Artificial Sequence
<220> FEATURE:
<223> OTHER INFORMATION: FL-Sp35 Primer

<400> SEQUENCE: 45
ggggcggaat tggatcctca cagatcctct tctgagatga g    41

<210> SEQ ID NO 46
<211> LENGTH: 41
<212> TYPE: DNA
<213> ORGANISM: Artificial Sequence
<220> FEATURE:
<223> OTHER INFORMATION: DN-Sp35 Primer

<400> SEQUENCE: 46
gaggatctcg acgcggccgc atggagacag acacactcct g    41

<210> SEQ ID NO 47
<211> LENGTH: 42
<212> TYPE: DNA
<213> ORGANISM: Artificial Sequence
<220> FEATURE:
<223> OTHER INFORMATION: DN-Sp35 Primer

<400> SEQUENCE: 47
gatacggatc ctcagccttt gccccggctc catagaaaca gc    42

<210> SEQ ID NO 48
<211> LENGTH: 37
<212> TYPE: DNA
<213> ORGANISM: Artificial Sequence
<220> FEATURE:
<223> OTHER INFORMATION: Human Sp35 Forward Primer

<400> SEQUENCE: 48

-continued cagcaggtcg acgcggccgc atgctggcgg ggggcgt    37

<210> SEQ ID NO 49
<211> LENGTH: 59
<212> TYPE: DNA
<213> ORGANISM: Artificial Sequence
<220> FEATURE:
<223> OTHER INFORMATION: Human Sp35 Reverse Primer

<400> SEQUENCE: 49
cagcaggtcg acctcgcccg gctggttggc caaccagccg ggcgaggtcg acctcgagg    59

<210> SEQ ID NO 50
<211> LENGTH: 22
<212> TYPE: DNA
<213> ORGANISM: Artificial Sequence
<220> FEATURE:
<223> OTHER INFORMATION: Sp35 Forward Primer

<400> SEQUENCE: 50 ctttccccctt cgacatcaag ac    22

<210> SEQ ID NO 51
<211> LENGTH: 18
<212> TYPE: DNA
<213> ORGANISM: Artificial Sequence
<220> FEATURE:
<223> OTHER INFORMATION: Sp35 Reverse Primer

<400> SEQUENCE: 51
cagcagcacc aggcagaa    18

<210> SEQ ID NO 52
<211> LENGTH: 23
<212> TYPE: DNA
<213> ORGANISM: Artificial Sequence
<220> FEATURE:
<223> OTHER INFORMATION: FAM Labeled Probe

<400> SEQUENCE: 52
atcgccacca ccatgggctt cat    23

<210> SEQ ID NO 53
<211> LENGTH: 21
<212> TYPE: DNA
<213> ORGANISM: Artificial Sequence
<220> FEATURE:
<223> OTHER INFORMATION: Mouse Forward Primer

<400> SEQUENCE: 53
ctatccaagc actgcctgct c    21

<210> SEQ ID NO 54
<211> LENGTH: 23
<212> TYPE: DNA
<213> ORGANISM: Artificial Sequence
<220> FEATURE:
<223> OTHER INFORMATION: Mouse Reverse Primer

<400> SEQUENCE: 54
gagttctagc tcctccaggt gtg    23

<210> SEQ ID NO 55
<211> LENGTH: 21
<212> TYPE: DNA
<213> ORGANISM: Artificial Sequence

```
<220> FEATURE:
<223> OTHER INFORMATION: Mouse Reverse Primer

<400> SEQUENCE: 55
gatgcccttc agctcgatgc g                                              21

<210> SEQ ID NO 56
<211> LENGTH: 32
<212> TYPE: DNA
<213> ORGANISM: Artificial Sequence
<220> FEATURE:
<223> OTHER INFORMATION: Sp35 Primer

<400> SEQUENCE: 56
gattactcga gatgctggcg gggggcgtga gg                                  32

<210> SEQ ID NO 57
<211> LENGTH: 36
<212> TYPE: DNA
<213> ORGANISM: Artificial Sequence
<220> FEATURE:
<223> OTHER INFORMATION: Sp35 Primer

<400> SEQUENCE: 57
cgcgggaatt ctcatatcat cttcatgttg aacttg                              36

<210> SEQ ID NO 58
<211> LENGTH: 10
<212> TYPE: PRT
<213> ORGANISM: Homo sapiens

<400> SEQUENCE: 58

Gly Ser Gly Cys Leu Ser Pro Arg Lys His
1               5                   10

<210> SEQ ID NO 59
<211> LENGTH: 10
<212> TYPE: PRT
<213> ORGANISM: Homo sapiens

<400> SEQUENCE: 59

Gly Ser Gly Cys Leu Ser Pro Arg Ile His
1               5                   10

<210> SEQ ID NO 60
<211> LENGTH: 8
<212> TYPE: PRT
<213> ORGANISM: Homo sapiens

<400> SEQUENCE: 60

Gly Ser Gly Cys Ile Pro Gln Ser
1               5

<210> SEQ ID NO 61
<211> LENGTH: 6
<212> TYPE: PRT
<213> ORGANISM: Homo sapiens

<400> SEQUENCE: 61

Leu Ser Pro Arg Lys His
1               5

<210> SEQ ID NO 62
<211> LENGTH: 6
<212> TYPE: PRT
<213> ORGANISM: Homo sapiens
```

```
<400> SEQUENCE: 62

Leu Ser Pro Glu Lys Val
1               5

<210> SEQ ID NO 63
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Position 1 is Biotinylated-Gly

<400> SEQUENCE: 63

Gly Ser Gly Cys Leu Ser Pro Arg Lys His Cys
1               5                   10

<210> SEQ ID NO 64
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Position 1 is Biotinylated-Gly

<400> SEQUENCE: 64

Gly Ser Gly Cys Lys His Ser Pro Leu Arg Cys
1               5                   10

<210> SEQ ID NO 65
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Position 1 is Biotinylated-Gly

<400> SEQUENCE: 65

Gly Ser Gly Cys Leu Ser Pro Glu Lys Val Cys
1               5                   10

<210> SEQ ID NO 66
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Position 1 is Acetylated-Cys

<400> SEQUENCE: 66

Cys Leu Ser Pro Arg Lys His Cys
1               5

<210> SEQ ID NO 67
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Position 1 is Acetylated-Cys

<400> SEQUENCE: 67

Cys Leu Ser Pro Glu Lys Val Cys
1               5
```

```
<210> SEQ ID NO 68
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any Basic Amino Acid
<220> FEATURE:
<221> NAME/KEY: MISC_FEATURE
<222> LOCATION: (4)..(4)
<223> OTHER INFORMATION: Xaa is any Amino Acid
<220> FEATURE:
<221> NAME/KEY: MISC_FEATURE
<222> LOCATION: (5)..(5)
<223> OTHER INFORMATION: Xaa is any Basic Amino Acid

<400> SEQUENCE: 68

Ile Thr Xaa Xaa Xaa
1               5

<210> SEQ ID NO 69
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any Basic Amino Acid
<220> FEATURE:
<221> NAME/KEY: MISC_FEATURE
<222> LOCATION: (4)..(4)
<223> OTHER INFORMATION: Xaa is any Amino Acid
<220> FEATURE:
<221> NAME/KEY: MISC_FEATURE
<222> LOCATION: (5)..(5)
<223> OTHER INFORMATION: Xaa is any Basic Amino Acid

<400> SEQUENCE: 69

Ala Cys Xaa Xaa Xaa
1               5

<210> SEQ ID NO 70
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any Basic Amino Acid
<220> FEATURE:
<221> NAME/KEY: MISC_FEATURE
<222> LOCATION: (4)..(4)
<223> OTHER INFORMATION: Xaa is any Amino Acid
<220> FEATURE:
<221> NAME/KEY: MISC_FEATURE
<222> LOCATION: (5)..(5)
<223> OTHER INFORMATION: Xaa is any Basic Amino Acid

<400> SEQUENCE: 70

Val Cys Xaa Xaa Xaa
1               5

<210> SEQ ID NO 71
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any Basic Amino Acid
<220> FEATURE:
```

```
<221> NAME/KEY: MISC_FEATURE
<222> LOCATION: (4)..(4)
<223> OTHER INFORMATION: Xaa is any Amino Acid
<220> FEATURE:
<221> NAME/KEY: MISC_FEATURE
<222> LOCATION: (5)..(5)
<223> OTHER INFORMATION: Xaa is any Basic Amino Acid

<400> SEQUENCE: 71

Ser Pro Xaa Xaa Xaa
1               5

<210> SEQ ID NO 72
<211> LENGTH: 5
<212> TYPE: PRT
<213> ORGANISM: Homo sapiens

<400> SEQUENCE: 72

Ser Pro Arg Leu His
1               5

<210> SEQ ID NO 73
<211> LENGTH: 200
<212> TYPE: DNA
<213> ORGANISM: Artificial Sequence
<220> FEATURE:
<223> OTHER INFORMATION: General Structure for an Oligonucleotide used
      in Preparation of an siRNA Molecule
<220> FEATURE:
<221> NAME/KEY: misc_feature
<222> LOCATION: (1)..(200)
<223> OTHER INFORMATION: n is a, c, g, t or u
<220> FEATURE:
<221> NAME/KEY: misc_feature
<222> LOCATION: (2)..(200)
<223> OTHER INFORMATION: nucleotide may be missing

<400> SEQUENCE: 73
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn                                                200

<210> SEQ ID NO 74
<211> LENGTH: 200
<212> TYPE: DNA
<213> ORGANISM: Artificial Sequence
<220> FEATURE:
<223> OTHER INFORMATION: General Structure for an Oligonucleotide used
      in Preparation of an siRNA Molecule
<220> FEATURE:
<221> NAME/KEY: misc_feature
<222> LOCATION: (1)..(200)
<223> OTHER INFORMATION: n is a, c, g, t or u
<220> FEATURE:
<221> NAME/KEY: misc_feature
<222> LOCATION: (2)..(200)
<223> OTHER INFORMATION: nucleotide may be missing

<400> SEQUENCE: 74
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn                                                200

<210> SEQ ID NO 75
```

```
<211> LENGTH: 11
<212> TYPE: PRT
<213> ORGANISM: Homo sapiens

<400> SEQUENCE: 75

Gly Ser Gly Cys Leu Ser Pro Arg Lys His Cys
1               5                   10

<210> SEQ ID NO 76
<211> LENGTH: 11
<212> TYPE: PRT
<213> ORGANISM: Homo sapiens

<400> SEQUENCE: 76

Gly Ser Gly Cys Lys His Ser Pro Leu Arg Cys
1               5                   10

<210> SEQ ID NO 77
<211> LENGTH: 11
<212> TYPE: PRT
<213> ORGANISM: Homo sapiens

<400> SEQUENCE: 77

Gly Ser Gly Cys Leu Ser Pro Glu Lys Val Cys
1               5                   10

<210> SEQ ID NO 78
<211> LENGTH: 8
<212> TYPE: PRT
<213> ORGANISM: Homo sapiens

<400> SEQUENCE: 78

Cys Leu Ser Pro Arg Lys His Cys
1               5

<210> SEQ ID NO 79
<211> LENGTH: 8
<212> TYPE: PRT
<213> ORGANISM: Homo sapiens

<400> SEQUENCE: 79

Cys Leu Ser Pro Glu Lys Val Cys
1               5

<210> SEQ ID NO 80
<211> LENGTH: 6
<212> TYPE: PRT
<213> ORGANISM: Homo sapiens

<400> SEQUENCE: 80

Leu Ser Pro Arg Lys Lys
1               5

<210> SEQ ID NO 81
<211> LENGTH: 6
<212> TYPE: PRT
<213> ORGANISM: Homo sapiens

<400> SEQUENCE: 81

Leu Ser Pro Arg Lys Arg
1               5

<210> SEQ ID NO 82
<211> LENGTH: 6
<212> TYPE: PRT
<213> ORGANISM: Homo sapiens
```

<400> SEQUENCE: 82

Leu Ser Pro Lys Lys His
1               5

<210> SEQ ID NO 83
<211> LENGTH: 6
<212> TYPE: PRT
<213> ORGANISM: Homo sapiens

<400> SEQUENCE: 83

Leu Ser Pro His Lys His
1               5

<210> SEQ ID NO 84
<211> LENGTH: 6
<212> TYPE: PRT
<213> ORGANISM: Homo sapiens

<400> SEQUENCE: 84

Leu Ser Pro Arg Arg His
1               5

<210> SEQ ID NO 85
<211> LENGTH: 6
<212> TYPE: PRT
<213> ORGANISM: Homo sapiens

<400> SEQUENCE: 85

Leu Ser Pro Arg His His
1               5

<210> SEQ ID NO 86
<211> LENGTH: 6
<212> TYPE: PRT
<213> ORGANISM: Homo sapiens

<400> SEQUENCE: 86

Leu Ser Pro Arg Arg Arg
1               5

<210> SEQ ID NO 87
<211> LENGTH: 6
<212> TYPE: PRT
<213> ORGANISM: Homo sapiens

<400> SEQUENCE: 87

Leu Ser Pro His His His
1               5

<210> SEQ ID NO 88
<211> LENGTH: 6
<212> TYPE: PRT
<213> ORGANISM: Homo sapiens

<400> SEQUENCE: 88

Leu Ser Pro Lys Lys Lys
1               5

<210> SEQ ID NO 89
<211> LENGTH: 7
<212> TYPE: PRT
<213> ORGANISM: Homo sapiens

<400> SEQUENCE: 89

```
Trp Leu Ser Pro Arg Lys His
1               5

<210> SEQ ID NO 90
<211> LENGTH: 7
<212> TYPE: PRT
<213> ORGANISM: Homo sapiens

<400> SEQUENCE: 90

Trp Leu Ser Pro Arg Lys Lys
1               5

<210> SEQ ID NO 91
<211> LENGTH: 7
<212> TYPE: PRT
<213> ORGANISM: Homo sapiens

<400> SEQUENCE: 91

Trp Leu Ser Pro Arg Lys Arg
1               5

<210> SEQ ID NO 92
<211> LENGTH: 7
<212> TYPE: PRT
<213> ORGANISM: Homo sapiens

<400> SEQUENCE: 92

Trp Leu Ser Pro Lys Lys His
1               5

<210> SEQ ID NO 93
<211> LENGTH: 7
<212> TYPE: PRT
<213> ORGANISM: Homo sapiens

<400> SEQUENCE: 93

Trp Leu Ser Pro His Lys His
1               5

<210> SEQ ID NO 94
<211> LENGTH: 7
<212> TYPE: PRT
<213> ORGANISM: Homo sapiens

<400> SEQUENCE: 94

Trp Leu Ser Pro Arg Arg His
1               5

<210> SEQ ID NO 95
<211> LENGTH: 7
<212> TYPE: PRT
<213> ORGANISM: Homo sapiens

<400> SEQUENCE: 95

Trp Leu Ser Pro Arg His His
1               5

<210> SEQ ID NO 96
<211> LENGTH: 7
<212> TYPE: PRT
<213> ORGANISM: Homo sapiens

<400> SEQUENCE: 96

Trp Leu Ser Pro Arg Arg Arg
1               5
```

```
<210> SEQ ID NO 97
<211> LENGTH: 7
<212> TYPE: PRT
<213> ORGANISM: Homo sapiens

<400> SEQUENCE: 97

Trp Leu Ser Pro His His His
1               5

<210> SEQ ID NO 98
<211> LENGTH: 7
<212> TYPE: PRT
<213> ORGANISM: Homo sapiens

<400> SEQUENCE: 98

Trp Leu Ser Pro Lys Lys Lys
1               5

<210> SEQ ID NO 99
<211> LENGTH: 8
<212> TYPE: PRT
<213> ORGANISM: Homo sapiens
<220> FEATURE:
<221> NAME/KEY: MISC_FEATURE
<222> LOCATION: (5)..(7)
<223> OTHER INFORMATION: Xaa is either lysine, arginine, histidine,
      glutamine, or asparagine

<400> SEQUENCE: 99

Cys Leu Ser Pro Xaa Xaa Xaa Cys
1               5

<210> SEQ ID NO 100
<211> LENGTH: 2897
<212> TYPE: DNA
<213> ORGANISM: Homo sapiens
<220> FEATURE:
<221> NAME/KEY: misc_feature
<222> LOCATION: (2376)..(2376)
<223> OTHER INFORMATION: n = a, t, c or g
<220> FEATURE:
<221> NAME/KEY: misc_feature
<222> LOCATION: (2381)..(2381)
<223> OTHER INFORMATION: n = a, t, c or g
<220> FEATURE:
<221> NAME/KEY: misc_feature
<222> LOCATION: (2859)..(2859)
<223> OTHER INFORMATION: n = a, t, c or g
<220> FEATURE:
<221> NAME/KEY: misc_feature
<222> LOCATION: (2861)..(2861)
<223> OTHER INFORMATION: n = a, t, c or g
<220> FEATURE:
<221> NAME/KEY: misc_feature
<222> LOCATION: (2871)..(2871)
<223> OTHER INFORMATION: n = a, t, c or g
<220> FEATURE:
<221> NAME/KEY: misc_feature
<222> LOCATION: (2877)..(2877)
<223> OTHER INFORMATION: n = a, t, c or g
<220> FEATURE:
<221> NAME/KEY: misc_feature
<222> LOCATION: (2880)..(2880)
<223> OTHER INFORMATION: n = a, t, c or g

<400> SEQUENCE: 100
ggagagacat gcgattggtg accgagccga gcggaccgaa ggcgcgcccg agatgcaggt      60
gagcaagagg atgctggcgg ggggcgtgag gagcatgccc agcccctcc tggcctgctg     120 gcagcccatc ctcctgctgg tgctgggctc agtgctgtca ggctcggcca cgggctgccc     180
```

-continued

```
gccccgctgc gagtgctccg cccaggaccg cgctgtgctg tgccaccgca agcgctttgt    240
ggcagtcccc gagggcatcc ccaccgagac gcgcctgctg gacctaggca agaaccgcat    300
caaaacgctc aaccaggacg agttcgccag cttcccgcac ctggaggagc tggagctcaa    360
cgagaacatc gtgagcgccg tggagcccgg cgccttcaac aacctcttca acctccggac    420
gctgggtctc cgcagcaacc gcctgaagct catcccgcta ggcgtcttca ctggcctcag    480
caacctgacc aagctggaca tcagcgagaa caagattgtt atcctactgg actacatgtt    540
tcaggacctg tacaacctca agtcactgga ggttggcgac aatgacctcg tctacatctc    600
tcaccgcgcc ttcagcggcc tcaacagcct ggagcagctg acgctggaga aatgcaacct    660
gacctccatc cccaccgagg cgctgtccca cctgcacggc tcatcgtcc tgaggctccg    720 gcacctcaac atcaatgcca tccgggacta ctccttcaag aggctctacc gactcaaggt    780
cttggagatc tcccactggc cctacttgga caccatgaca cccaactgcc tctacggcct    840
caacctgacg tccctgtcca tcacacactg caatctgacc gctgtgccct acctggccgt    900
ccgccaccta gtctatctcc gcttcctcaa cctctcctac aaccccatca gcaccattga    960
gggctccatg ttgcatgagc tgctccggct gcaggagatc cagctggtgg gcgggcagct   1020
ggccgtggtg gagccctatg ccttccgcgg cctcaactac ctgcgcgtgc tcaatgtctc   1080
tggcaaccag ctgaccacac tggaggaatc agtcttccac tcggtgggca acctggagac   1140
actcatcctg gactccaacc gcctggcctg cgactgtcgg ctcctgtggg tgttccggcg   1200
ccgctggcgg ctcaacttca accggcagca gcccacgtgc gccacgcccg agtttgtcca   1260
gggcaaggag ttcaaggact ccctgatgt gctactgccc aactacttca cctgccgccg   1320
cgcccgcatc cggaccgca aggcccagca ggtgtttgtg gacgagggcc acacggtgca   1380
gtttgtgtgc cgggccgatg cgacccgcc gcccgccatc ctctggctct cacccgaaa   1440 gcacctggtc tcagccaaga gcaatgggcg gctcacagtc ttccctgatg gcacgctgga   1500
ggtgcgctac gcccaggtac aggacaacgg cacgtacctg tgcatcgcgg ccaacgcggg   1560
cggcaacgac tccatgcccg cccacctgca tgtgcgcagc tactcgcccg actggcccca   1620
tcagcccaac aagaccttcg cttttcatctc caaccagccg ggcgagggag aggccaacag   1680
cacccgcgcc actgtgcctt tccccttcga catcaagacc ctcatcatcg ccaccaccat   1740
gggcttcatc tctttcctgg gcgtcgtcct cttctgcctg tgctgctgt ttctctggag   1800 ccggggcaag ggcaacacaa agcacaacat cgagatcgag tatgtgcccc gaaagtcgga   1860
cgcaggcatc agctccgccg acgcgccccg caagttcaac atgaagatga tatgaggccg   1920
gggcgggggg cagggacccc cgggcggccg ggcagggaaa ggggcctggc cgccacctgc   1980
tcactctcca gtccttccca cctcctccct acccttctac acacgttctc tttctcctc   2040 ccgcctccgt cccctgctgc ccccgccag ccctcaccac ctgccctcct tctaccagga   2100
cctcagaagc ccagacctgg ggaccccacc tacacagggg cattgacaga ctggagttga   2160
aagccgacga accgacacgc ggcagagtca ataattcaat aaaaaagtta cgaactttct   2220
ctgtaacttg ggtttcaata attatggatt tttatgaaaa cttgaaataa taaaagaga   2280 aaaaaactat ttcctatagc tagtcggaat gcaaactttt gacgtcctga ttgctccagg   2340
gccctcttcc aactcagttt cttgttttc tcttcntcct nctcctcttc ttcctccttt   2400
ctcttctctt ccccagtgg ggagggatca ctcaggaaaa caggaaagga ggttccagcc   2460
ccacccacct gccacccccg ccccaggcac catcaggagc aggctagggg gcaggcctgg   2520
gcccagctcc gggctggctt tttgcagggc gcaggtggag gggacaggtc tgccgatggg   2580
```

```
ggtgggagcc tgtctgctgg gctgccaggc ggcaccactg caagggtgg gagcctggct    2640 cgggtgtggc tgagactctg gacagaggct ggggtcctcc tgggggacag cacagtcagt    2700
ggagagagcc aggggctgga ggtggggccc accccagcct ctggtcccag ctctgctgct    2760
cacttgctgt gtggccctca agcaggtcca ctggcctctc tgggcctcag tctccacatc    2820
tgtacaaatg ggaacattac cccctgccct gcctacctna nagggctgtt ntgaggnatn    2880
gatgagatga tgtatgt                                                   2897
```